US012264180B2

(12) United States Patent
Albertini et al.

(10) Patent No.: US 12,264,180 B2
(45) Date of Patent: *Apr. 1, 2025

(54) MUTATED GLYCOPROTEIN OF VESICULAR STOMATITIS VIRUS

(71) Applicants: Centre National de la Recherche Scientifique (CNRS), Paris (FR); Université Paris-Saclay, Gif sur Yvette (FR)

(72) Inventors: Aurélie Albertini, Gometz le Chatel (FR); Yves Gaudin, Paris (FR); Hélène Raux, Antony (FR); Laura Belot, Maurepas (FR); Jovan Nikolic, Paris (FR)

(73) Assignees: Centre National de la Recherche Scientifique (CNRS), Paris (FR); Université Paris-Saclay, Gif sur Yvette (FR)

(*) Notice: Subject to any disclaimer, the term of this patent is extended or adjusted under 35 U.S.C. 154(b) by 0 days.

This patent is subject to a terminal disclaimer.

(21) Appl. No.: 18/629,504

(22) Filed: Apr. 8, 2024

(65) Prior Publication Data

US 2024/0327467 A1    Oct. 3, 2024

Related U.S. Application Data

(63) Continuation of application No. 18/473,720, filed on Sep. 25, 2023, now Pat. No. 12,030,915, which is a continuation of application No. 16/649,271, filed as application No. PCT/EP2018/075824 on Sep. 24, 2018, now Pat. No. 12,091,434.

(30) Foreign Application Priority Data

Sep. 22, 2017   (EP) .................................... 17306255

(51) Int. Cl.
*C07K 14/05*   (2006.01)
*C07K 14/005*  (2006.01)
*C12N 7/00*    (2006.01)

(52) U.S. Cl.
CPC .............. *C07K 14/005* (2013.01); *C12N 7/00* (2013.01); *C12N 2760/20222* (2013.01); *C12N 2760/20232* (2013.01); *C12N 2760/20245* (2013.01); *C12N 2760/20262* (2013.01)

(58) Field of Classification Search
None
See application file for complete search history.

(56) References Cited

U.S. PATENT DOCUMENTS 12,030,915 B2 *  7/2024  Albertini .............. C07K 14/005
2008/0124357 A1    5/2008  Yao et al.

FOREIGN PATENT DOCUMENTS

| EP | 2020444 A1    | 2/2009  |
| JP | 2005-516607 A | 6/2005  |
| JP | 2005-247757 A | 9/2005  |
| JP | 2010-535495 A | 11/2010 |
| JP | 2016-501528 A | 1/2016  |
| WO | 01/19380 A2   | 3/2001  |

OTHER PUBLICATIONS

Finkelstein et all., PNAS vol. 110, #18, pp. 7306-7311 (Year: 2013).*
Albertini et al.(2012). Molecular and Cellular Aspects of Rhabdovirus Entry. Viruses 4, 117-139.
Amirache et al. (2014). Mystery solved: VSV-G-LVs do not allow efficient gene transfer into unstimulated T cells, B cells, and HSCs because they lack the LDL receptor. Blood 123, 1422-1424.
Ammayappan et al. (2013). Characteristics of oncolytic vesicular stomatitis virus displaying tumor-targeting ligands. J Virol 87, 13543-13555.
Barber, G.N. (2005). VSV-tumor selective replication and protein translation. Oncogene 24, 7710-7719.
Ferlin et al. (2014). Characterization of pH-sensitive molecular switches that trigger the structural transition of vesicular stomatitis virus glycoprotein from the postfusion state toward the prefusion state. J Virol 88, 13396-13409.
Finkelshtein et al. ( 2013) . L DL receptor and its family members serve as the cellular receptors for vesicular stomatitis virus. Proceedings of the National Academy of Sciences of the United States of America 110, 7306-7311.
Roche et al. (2006). Crystal structure of the low-pH form of the vesicular stomatitis virus glycoprotein G. Science 313, 187-191.
Roche et al. (2007). Structure of the prefusion form of the vesicular stomatitis virus glycoprotein g. Science 315, 843-848.
Nikolic et al. Structural basis for the recognition of LDL-receptor family members by VSV glycoprotein. Nature communications, 9(1), 2018, 1-12.
Ammayappan et al. "Characteristics of Oncolytic Vesicular Stomatitis Virus Displaying Tumor-Targeting Ligands" Journal of Virology vol. 87 No. 24 p. 13543-13555 (Year: 2013).
He et al., Can immunotherapy reinforce chemotherapy efficacy? a new perspective on colorectal cancer treatment. Front. Immunol. 14: 1237764 (Year: 2023).
Messer et al. "Optimizing intracellular antibodies (intrabodies/nanobodies) to treat neurodegenerative disorders" Neurobiology of Disease 134 (2020) 104619.
Rose et al. "Glycoprotein Exchange Vectors Based on Vesicular Stomatitis Virus Allow Effective Boosting and Generation of Neutralizing Antibodies to a Primary Isolate of Human Immunodeficiency Virus Type 1" Journal of Virology, Dec. 2000, vol. 74, No. 23, p. 10903-10910.

(Continued)

*Primary Examiner* — Shanon A. Foley
*Assistant Examiner* — Myron G Hill
(74) *Attorney, Agent, or Firm* — Banner & Witcoff, Ltd.

(57) ABSTRACT

The invention relates to an isolated non-naturally occurring protein comprising the amino acid sequence as set forth in SEQ ID NO: 1, and wherein the amino acid in position 8, 47, 209 and/or 354 is substituted by any amino acid different from the amino acid indicated at that position in said sequence SEQ ID NO: 1.

25 Claims, 11 Drawing Sheets

Specification includes a Sequence Listing.

(56) References Cited

OTHER PUBLICATIONS

Brown et al. "A Receptor Mediated Pathway for Cholesterol Homeostasis" Science, vol. 232, Apr. 4, 1986 p. 34-47.

Hastie et al. Oncolytic Vesicular Stomatitis Virus in an Immunocompetent Model of MUC1-Positive or MUC1-Null Pancreatic Ductal Adenocarcinoma Journal of Virology p. 10283-10294, Sep. 2013 vol. 87 No. 18.

Harper et al. "Purification of proteins fused to glutathione S-tranferase" Methods Mol Biol. 2011 ; 681: 259-280. doi:10.1007/978-1-60761-913-0_14.

Fernandez et al.. "Genetically Engineered Vesicular Stomatitis Virus in Gene Therapy: Application for Treatment of Malignant Disease" Journal of Virology, vol. 76, No. 2, Jan. 2002, p. 895-904.

Apr. 25, 2023 (JP) Decision of Refusal Application No. 2020-516534.

Aug. 30, 2022 (JP) Decision of Refusal Application No. 2020-516534.

\* cited by examiner

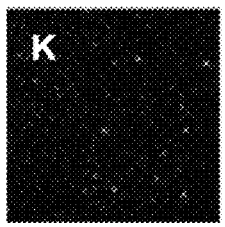 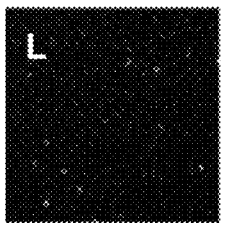 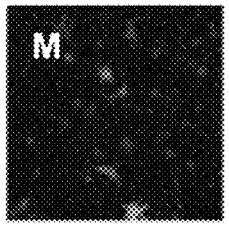 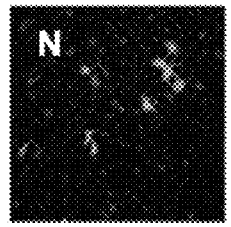 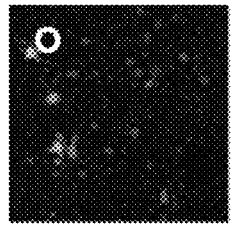
Fig. 13K  Fig. 13L  Fig. 13M  Fig. 13N  Fig. 13O
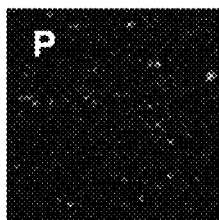 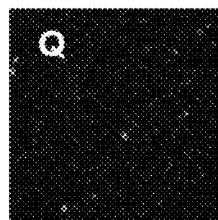 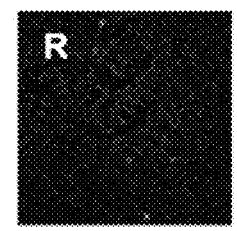 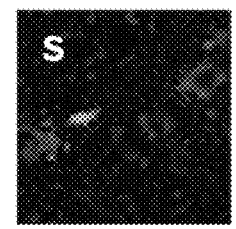 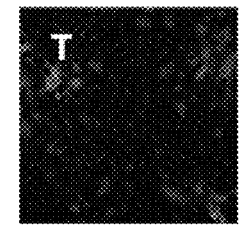
Fig. 13P  Fig. 13Q  Fig. 13R  Fig. 13S  Fig. 13T
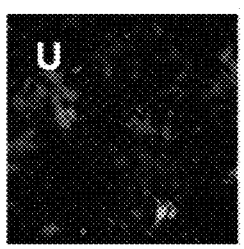 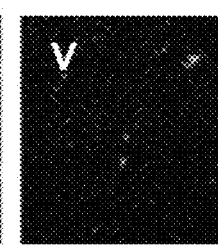 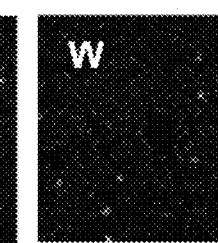 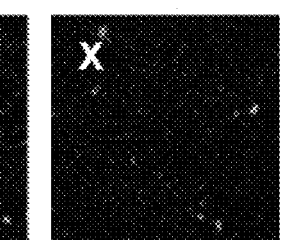
Fig. 13U  Fig. 13V  Fig. 13W  Fig. 13X

MUTATED GLYCOPROTEIN OF VESICULAR STOMATITIS VIRUS

RELATED APPLICATIONS

This application is a continuation application which claims priority to U.S. patent application Ser. No. 18/473,720, filed on Sep. 25, 2023 which is a continuation application which claims priority to U.S. patent application Ser. No. 16/649,271, filed on Mar. 20, 2020, which is a National Stage Application under 35 U.S.C. 371 of expired PCT application number PCT/EP2018/075824 designating the United States and filed Sep. 24, 2018; which claims the benefit of EP application Ser. No. 17/306,255.5 and filed Sep. 22, 2017 each of which are hereby incorporated by reference in their entireties.

SEQUENCE LISTING

The instant application contains a Sequence Listing which has been submitted electronically in XML format and is hereby incorporated by reference in its entirety. Said XML copy, created on Sep. 25, 2023, is named "Sequence_Listing_009782.00003_ST26" and is 584 KB in size.

FIELD OF THE INVENTION

The invention relates to a mutated viral protein, in particular a muted protein originating from an oncolytic virus.

BACKGROUND OF THE INVENTION

Vesicular stomatitis virus (VSV) is an enveloped, negative-strand RNA virus that belongs to the Vesiculovirus genus of the Rhabdovirus family. It is an arbovirus which can infect insects, cattle, horses and pigs. In mammals, its ability to infect and kill tumor cells while sparing normal cells makes it a promising oncolytic virus for the treatment of cancer (Barber, 2005; Fernandez et al., 2002; Hastie et al., 2013).

VSV genome encodes five structural proteins among which a single transmembrane glycoprotein (G). The glycoprotein is a classic type I membrane glycoprotein with an amino-terminal signal peptide, an ectodomain of about 450 amino acids, a single alpha helical transmembrane segment and a small intraviral carboxy-terminal domain. The signal peptide is cleaved in the lumen of the endoplasmic reticulum and the native glycoprotein consists in the ectodomain, the transmembrane domain and the intraviral domain.

G plays a critical role during the initial steps of virus infection (Albertini et al., 2012b). First, it is responsible for virus attachment to specific receptors. After binding, virions enter the cell by a clathrin-mediated endocytic pathway. In the acidic environment of the endocytic vesicle, G triggers the fusion between the viral and endosomal membranes, which releases the genome in the cytosol for the subsequent steps of infection. Fusion is catalyzed by a low-pH-induced large structural transition from a pre-toward a post-fusion conformation which are both trimeric (Roche et al., 2006; Roche et al., 2007).

The polypeptide chain of G ectodomain folds into three distinct domains which are the fusion domain (FD), the pleckstrin homology domain (PHD), and the trimerization domain (TrD). During the structural transition, the FD, the PHD and the TrD retain their tertiary structure. Nevertheless, they undergo large rearrangements in their relative orientation due to secondary changes in hinge segments (S1 to S5) which refold during the low-pH induced conformational change (Roche et al., 2006; Roche et al., 2007).

Recently, it has been shown that low-density lipoprotein receptor (LDL-R) and other members of this receptor family serve as VSV receptors (Finkelshtein et al., 2013).

The LDL-R is a type I transmembrane protein which regulates cholesterol homeostasis in mammalian cells (Brown and Goldstein, 1986). LDL-R removes cholesterol carrying lipoproteins from plasma circulation. Ligands bound extracellularly by LDL-R at neutral pH are internalized and then released in the acidic environment of the endosomes leading to their subsequent lysosomal degradation. The receptor then recycles back to the cell surface. LDL-R ectodomain is composed of a ligand-binding domain, an epidermal growth factor (EGF) precursor homology domain and a C-terminal domain enriched in O-linked oligosaccharides. The ligand binding domain is made of 7 cysteine-rich repeats (CR1 to CR7, FIG. 1). Each repeat is made of approximately 40 amino acids and contains 6 cysteine residues, engaged in 3 disulfide bridges, and an acidic residues cluster that coordinates a $Ca^{2+}$ ion. The intracellular release of the cargo is driven by a low-pH-induced conformational change of LDL-R from an open to a closed conformation.

The LDL-R gene family consists of trans-membrane receptors that reside on the cell-surface, are involved in endocytic uptake of lipoproteins, and require $Ca^{2+}$ for ligand binding. All these receptors have in common several CR repeats (up to several tens), EGF precursor-like repeats, a membrane-spanning region and an intracellular domain containing at least one internalization signal sequence. They are found ubiquitously in all animals including insects.

VSV-G has been widely used for pseudotyping other viruses and VSV-G-pseudotyped lentiviruses (VSV-G-LVs) exhibit the same broad tropism as VSV.

On the other hand, VSV-G-LVs do not allow efficient gene transfer into unstimulated T cells, B cells, and hematopoietic stem cells, as they have a very low expression level of LDL-R (Amirache et al., 2014).

The broad tropism of VSV and VSV-G LVs, due to the ubiquitous distribution of the LDL-R receptor family members, is a limitation of their therapeutic use. This is particularly the case in oncotherapy when one wants to target specifically tumor cells.

OBJECT OF THE INVENTION

One aim of the invention is to obviate this drawback.

One aim of the invention is to provide a new mutated VSV-G protein deficient in one of its properties in order to specifically target this protein.

Another aim of the invention is to provide a new VSV expressing such a protein and its use in oncotherapy.

SUMMARY OF THE INVENTION

The invention relates to an isolated non-naturally occurring protein comprising, consisting essentially of or consisting of the amino acid sequence as set forth in SEQ ID NO: 1, which corresponds to (which is) the amino acid sequence of the ectodomain of VSV Indiana strain, wherein at least one of the amino acids at positions 8, 47, 209 and 354, said numbering being made from the position of the first amino acid in the sequence SEQ ID NO:1, is substituted by an amino acid different from the amino acid indicated at that position in said sequence SEQ ID NO: 1, or any homologous protein derived from said protein as set forth in SEQ ID NO:1 by substitution, addition or deletion of at least one amino acid, provided that the derived protein retains at least 70% of identity with the amino acid sequence as set forth in SEQ ID NO: 1, and said derived protein retaining the ability to induce membrane fusion and retaining the ability to interact with LDL membrane receptor, wherein at least one amino acid, of said homologous protein located at a position equivalent to the positions 8, 47, 209 and 354 of said sequence SEQ ID NO: 1, is substituted by an amino acid distinct from the amino acid indicated at that position in the sequence SEQ ID NO:1, said isolated non-naturally occurring protein retaining the ability to induce membrane fusion and being unable to interact with LDL membrane receptor.

In a preferred embodiment, the amino acid at position 8 in SEQ ID NO: 1 of the isolated non-naturally occurring protein of invention (said numbering being made from the position of the first amino acid in the sequence SEQ ID NO: 1), or at the position equivalent in the homologous protein derived from said protein as set forth in SEQ ID NO:1 of the invention, cannot be a Y residue.

DETAILED DESCRIPTION

In a preferred embodiment, the amino acid at position 209 in SEQ ID NO: 1 of the isolated non-naturally occurring protein of invention (said numbering being made from the position of the first amino acid in the sequence SEQ ID NO: 1), or at the position equivalent in the homologous protein derived from said protein as set forth in SEQ ID NO:1 of the invention, cannot be a H residue.

Thus, in other words, the invention relates to an isolated non-naturally occurring protein comprising the amino acid sequence as set forth in SEQ ID NO: 1, which corresponds to (which is) the amino acid sequence of the ectodomain of VSV Indiana strain, wherein at least one of the amino acids at positions 8, 47, 209 and 354, said numbering being made from the position of the first amino acid in the sequence SEQ ID NO: 1, is substituted by an amino acid different from the amino acid indicated at that position in said sequence SEQ ID NO: 1, wherein the substitution at position 8 is by any amino acid different from the amino acid indicated at that position in said sequence SEQ ID NO: 1, except Y, and wherein the substitution at position 209 is by any amino acid different from the amino acid indicated at that position in said sequence SEQ ID NO: 1, except H, or any homologous protein derived from said protein as set forth in SEQ ID NO: 1 by substitution, addition or deletion of at least one amino acid, provided that the derived protein retains at least 70% of identity with the amino acid sequence as set forth in SEQ ID NO: 1, and said derived protein retaining the ability to induce membrane fusion and retaining the ability to interact with LDL membrane receptor, wherein at least one amino acid, of said homologous protein located at a position equivalent to the positions 8, 47, 209 and 354 of said sequence SEQ ID NO: 1, is substituted by an amino acid distinct from the amino acid indicated at that position in the sequence SEQ ID N° 1, wherein the substitution of the amino acid located at a position equivalent to the position 8 is by any amino acid distinct from the amino acid indicated at that position in the sequence SEQ ID N° 1, except Y, and wherein the substitution of the amino acid located at a position equivalent to the position 209 is by any amino acid distinct from the amino acid indicated at that position in the sequence SEQ ID N° 1, except H, said isolated non-naturally occurring protein retaining the ability to induce membrane fusion and being unable to interact with LDL membrane receptor.

Advantageously, the invention relates to an isolated non-naturally occurring protein comprising, consisting essentially of or consisting of the amino acid sequence as set forth in SEQ ID NO: 1, which corresponds to (which is) the amino acid sequence of the ectodomain of VSV Indiana strain, wherein the amino acid at position 8, or at position 47, or at position 209, or at position 354, or at both positions 8 and 47, or at both positions 8 and 209, or at both positions 8 and 354, or at both positions 47 and 209, or at both positions 47 and 354, or at both positions 209 and 354, or at the positions 8 and 47 and 209, or at the positions 8 and 47 and 354, or at the positions 8 and 209 and 354, or at the positions 47 and 209 and 354, or at the position 8 and 47 and 209 and 354, said numbering being made from the position of the first amino acid in the sequence SEQ ID NO:1, are substituted by any amino acid different from the amino acid found in SEQ ID NO: 1, or any homologous protein derived from said protein as set forth in SEQ ID NO:1 by substitution, addition or deletion of at least one amino acid, provided that the derived protein retains at least 70% of identity with the amino acid sequence as set forth in SEQ ID NO: 1, and said derived protein retaining the ability to induce membrane fusion and retaining the ability to interact with LDL membrane receptor, wherein the amino acid, of said homologous protein, located at a position equivalent to position 8, or to position 47, or to position 209, or to position 354, or to both positions 8 and 47, or to both positions 8 and 209, or to both positions 8 and 354, or to both positions 47 and 209, or to both positions 47 and 354, or to both positions 209 and 354, or to the positions 8 and 47 and 209, or to the positions 8 and 47 and 354, or at the positions 8 and 209 and 354, or to the positions 47 and 209 and 354, or to the position 8 and 47 and 209 and 354, are substituted by any amino acid different from the amino acid found in SEQ ID NO: 1, in particular the amino acid at position 8 is substituted by any amino acid except H, and preferably except Y, the amino acid at position 47 is substituted by any amino acid except K, the amino acid at position 209 is substituted by any amino acid except Y and preferably except H, the amino acid at position 354 is substituted by any amino acid except R, the numbering being made from the position of the first amino acid in the sequence SEQ ID NO: 1, said isolated non-naturally occurring protein retaining the ability to induce membrane fusion and being unable to interact with LDL membrane receptor.

Advantageously, the invention relates to an isolated non-naturally occurring protein comprising or consisting essentially of or consisting of the amino acid sequence as set forth in SEQ ID NO: 1,

KFTLVFPHNQKGNWKNVPSNYHYCPSSSDLNWHNDLIGTAIQVKMPKSHKAIQADGW

MCHASKWVTTCDFRWYGPKYITQSIRSFTPSVEQCKESLEQTKQGTWLNPGFPPQSC

GYATVTDAEAVIVQVTPHHVLVDEYTGHWVDSQFINGKCSNYICPTVHNSTTWHSDY

KVKGLCDSNLISMDITFFSEDGELSSLGKEGTGFRSNYFAYETGGKACKMQYCKHWGV

RLPSGVWFEMADKDLFAAARFPECPEGSSTSAPSQTSVDVSLIQDVERILDYSLCQET

WSKIRAGLPISPVDLSYLAPKNPGIGPAFTILNGILKYFETRYIRVDIAAPILSRMV

GMISGTTTERELWDDWAPYEDVBIGPNGVLRISSGVKFPLYMIGHGMLDSDLHLSSK

AQVFEHPHIQDAASQLPDDEDLFFGDTGLSKNPIELVEGWFSSWKSSIASFFFILGLI

IGLFLVLRVGIHCIKLKHTKKRQIYTDIEMNRLGK or any protein derived from said protein as set forth in SEQ ID NO: 1 by substitution, addition or deletion of at least one amino acid, provided that said protein derived protein derived from said protein as set forth in SEQ ID NO: 1 retains the boxed amino acids as shown above, wherein the amino acid at position 8, or at position 47, or at position 209, or at position 354, or at both positions 8 and 47, or at both positions 8 and 209, or at both positions 8 and 354, or at both positions 47 and 209, or at both positions 47 and 354, or at both positions 209 and 354, or at the positions 8 and 47 and 209, or at the positions 8 and 47 and 354, or at the positions 8 and 209 and 354, or at the positions 47 and 209 and 354, or at the position 8 and 47 and 209 and 354, or the corresponding positions in the protein derived from said protein as set forth in SEQ ID NO: 1, are substituted by any amino acid different from the amino acid found in SEQ ID NO: 1, in particular the amino acid at position 8 is substituted by any amino acid except H, and preferably except Y, the amino acid at position 47 is substituted by any amino acid except K, the amino acid at position 209 is substituted by any amino acid except Y and preferably except H, the amino acid at position 354 is substituted by any amino acid except R, the numbering being made from the position of the first amino acid in the sequence SEQ ID NO: 1, said isolated non-naturally occurring protein retaining the ability to induce membrane fusion and is unable to interact with LDL membrane receptor.

Advantageously, the invention relates to an isolated non-naturally occurring protein comprising, consisting essentially of or consisting of the amino acid sequence as set forth in SEQ ID NO: 1, which corresponds to (which is) the amino acid sequence of the ectodomain of VSV Indiana strain, wherein the amino acid at position 47 or at position 354, or at both positions 47 and 354, said numbering being made from the position of the first amino acid in the sequence SEQ ID NO:1, are substituted by any amino acid, in particular by any amino acid except K or R, or any homologous protein derived from said protein as set forth in SEQ ID NO:1 by substitution, addition or deletion of at least one amino acid, provided that the derived protein retains at least 70% of identity with the amino acid sequence as set forth in SEQ ID NO: 1, and said derived protein retaining the ability to induce membrane fusion and retaining the ability to interact with LDL membrane receptor, wherein the amino acid, of said homologous protein, located at a position equivalent to position 47 or to position 354, or to both positions 47 and 354, are substituted by any amino acid, in particular any amino acid except K or R, the numbering being made from the position of the first amino acid in the sequence SEQ ID NO: 1, said isolated non-naturally occurring protein retaining the ability to induce membrane fusion and being unable to interact with LDL membrane receptor.

In one embodiment, said isolated non-naturally occurring protein further comprises a substitution of the amino acid at position 8, or at position 209, or at both positions 8 and 209, by any amino acid, said numbering being made from the position of the first amino acid in the sequence SEQ ID NO:1, preferably wherein the amino acid at position 8 is substituted by any amino acid except H or Y, and preferably wherein the amino acid at position 209 is substituted by any amino acid except H or Y.

Advantageously, the invention relates to an isolated non-naturally occurring protein as defined above comprising, consisting essentially of or consisting of the amino acid sequence as set forth in SEQ ID NO: 1.

KFTLVFPHNQKGNWKNVPSNYHYCPSSSDLNWHNDLIGTAIQVKMPKSHKAIQADGW

MCHASKWVTTCDFRWYGPKYITQSIRSFTPSVEQCKESLEQTKQGTWLNPGFPPQSC

-continued

```
GYATVIDAEAVIVQVLPHHVLVDEYTGHWVDSQFINGKCSNYICHTVHNSTIWHSDY

KVKGLCDSNLISMDITFFSEDGELSSLGKEGTGFRSNYEAYETGGKACKMQYCKHWGV

RLPSGVWFEMADKDLFAAARFPECPEGSSISAPSQTSVDVSLIQDVERILDYSLCQHT

WSKIRAGLPISPVDLSYLAPKNPGIGPAFTIINGILKYFETRYIRVDIAAPILSRMV

GMISGTTTERELWDDWAPYEDVBIGPNGVLRISSGYKFPLYMIGHGMLDSDLHLSSK

AQVFEHPHIQDAASQLPDDEDLFFGDTGLSKNPIELVEGWFSSWKSSIASFFFILGLI

IGLFLVLRVGIHCIKLKHTKKRQIYTDIEMNRLGK
``` or any protein derived from said protein as set forth in SEQ ID NO: 1 by substitution, addition or deletion of at least one amino acid, provided that said protein derived protein derived from said protein as set forth in SEQ ID NO: 1 retains the boxed amino acids as shown above, wherein the amino acid at position 47 or at position 354, or at both positions 47 and 354, or the corresponding positions in the protein derived from said protein as set forth in SEQ ID NO: 1, are substituted by any amino acid, in particular by any amino acid except K or R, the numbering being made from the position of the first amino acid in the sequence SEQ ID NO: 1, said isolated non-naturally occurring protein retaining the ability to induce membrane fusion and is unable to interact with LDL membrane receptor.

In one embodiment, said isolated non-naturally occurring protein further comprises a substitution of the amino acid at position 8, or at position 209, or at both positions 8 and 209, by any amino acid distinct from the amino acid indicated at that position in the sequence SEQ ID N° 1 or at the position equivalent in said homologous protein, said numbering being made from the position of the first amino acid in the sequence SEQ ID NO:1, preferably wherein the amino acid at position 8 is substituted by any amino acid except H or Y, and preferably wherein the amino acid at position 209 is substituted by any amino acid except H or Y.

The invention is based on the unexpected observation made by the inventors that a substitution of at least one amino acid residues at positions 8, 47, 209 or 354, or the combination of two or three or the four amino acids, affects the ability of VSV G protein to interact with its receptor (LDL membrane receptor) but retain its property to induce membrane fusion, in particular at low pH.

The invention encompasses proteins containing the amino acid sequence SEQ ID NO: 1, which corresponds to the native form of the Indiana strain of VSV, and which lacks the signal peptide. The invention also encompasses any G protein from VSV strains provided that said protein retains the amino acids that are represented with a box in SEQ ID NO: 1.

The G proteins form VSV strains may differ by addition, substitution or insertion of at least one amino acid which are not the amino acid represented with a bow in SEQ ID NO: 1.

Regarding the numbering of the amino acid, this numbering is in the invention conventionally based on the numbering of the amino acids of the native form of the G protein of VSV G Indiana as set forth in SEQ ID NO: 1. The skilled person knows the sequence alignment algorithms and programs (ClustalW for instance) and could easily compare the sequences of different G proteins and recalculate the exact position for a determined G protein compared to the numbering obtain in SEQ ID NO: 1. For sake of clarity, the amino acid at positions 8, 47, 209 and 354 are indicated in bold in the above SEQ ID NO: 1.

The invention encompasses proteins containing the amino acid sequence SEQ ID NO: 1. The invention also encompasses any homologous G protein from VSV strains provided that said protein retains at least 70% of identity with the amino acid sequence SEQ ID NO: 1.

By "at least 70% of identity", it is meant in the invention 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% of identity with the sequence SEQ ID NO: 1.

Regarding the percentage of identity, it is defined by the percentage of amino acid residues of SEQ ID NO: 1 which align with the same amino acid in the sequence of the homologous protein. The sequence alignment is performed using dedicated algorithms and programs (such as ClustalW, for instance).

Therefore, the protein according to the invention may derive from the following amino acid sequences:

SEQ ID NO: 2, the full length VSV G protein from Indiana strain, by substitution of the amino acids at position 63, or at position 370, or both by any amino acid except K or R, SEQ ID NO: 3, the ectodomain of the VSV G protein from Marraba strain, by substitution of the amino acids at position 47, or at position 354, or both by any amino acid except K or R, SEQ ID NO: 4, the full length VSV G protein from Marraba strain, by substitution of the amino acids at position 63, or at position 370, or both by any amino acid except K or R, SEQ ID NO: 5, the ectodomain of the VSV G protein from New Jersey strain, by substitution of the amino acids at position 47, or at position 358, or both by any amino acid except K or R, SEQ ID NO: 6, the full length VSV G protein from New Jersey strain, by substitution of the amino acids at position 63, or at position 374, or both by any amino acid except K or R, SEQ ID NO: 7, the ectodomain of the VSV G protein from Carajas strain, by substitution of the amino acids at position 47, or at position 358, or both by any amino acid except K or R, SEQ ID NO: 8, the full length VSV G protein from Carajas strain, by substitution of the amino acids at position 63, or at position 374, or both by any amino acid except K or R, SEQ ID NO: 9, the ectodomain of the VSV G protein from Alagoa strain, by substitution of the amino acids at position 47, or at position 354, or both by any amino acid except K or R, SEQ ID NO: 10, the full length VSV G protein from Alagoa strain, by substitution of the amino acids at position 64, or at position 371, or both by any amino acid except K or R, SEQ ID NO: 11, the ectodomain of the VSV G protein from Cocal strain, by substitution of the amino acids at position 47, or at position 354, or both by any amino acid except K or R, and SEQ ID NO: 12, the full length VSV G protein from Cocal strain, by substitution of the amino acids at position 64, or at position 371, or both by any amino acid except K or R.

SEQ ID NO: 13, the ectodomain of the VSV G protein from Morreton strain, by substitution of the amino acids at position 47, or at position 354, or both by any amino acid except K or R, and SEQ ID NO: 14, the full length VSV G protein from Morreton strain, by substitution of the amino acids at position 64, or at position 371, or both by any amino acid except K or R.

Via the crystallographic characterization of the G protein, the inventors showed that residues K47 and R354 are highly critical for the interaction with the LDL derived receptor. When one or both residues are substituted by another amino acid residue have physical and chemical different properties, the resulting G protein loses its capacity to interact with cellular receptor. By contrast, the same resulting protein, in appropriate condition of pH retains its fusogenic property.

In the invention, the protein is isolated, which means that the protein has been isolated from its natural context. The protein is non-naturally occurring, which means that the only way to obtain this protein is to carry out a substitution, in a laboratory, by using technological methods man-made, well known in the art.

More advantageously, the invention relates to the isolated non-naturally occurring protein previously disclosed, wherein said protein comprises, or consists essentially of or consists of one of the following amino acid sequence:

SEQ ID NO: 15-20;
SEQ ID NO: 21-26;
SEQ ID NO: 27-32;
SEQ ID NO: 33-38;
SEQ ID NO: 39-44;
SEQ ID NO: 45-50; and
SEQ ID NO: 51-56, wherein the amino acid at position 47 or at position 354, or at both positions 47 and 354, or the corresponding positions in the protein derived from said protein as set forth in SEQ ID NO: 1, are any amino acid except K or R. In other words, in the invention the amino acids Xaa corresponds to any amino acid except R or K.

SEQ ID NO: 15 corresponds to the ectodomain of the VSV G protein from Indiana strain having a substitution at position 47, by any amino acid except K or R.

SEQ ID NO: 16 corresponds to the ectodomain of the VSV G protein from Indiana strain having a substitution at position 354, by any amino acid except K or R.

SEQ ID NO: 17 corresponds to the ectodomain of the VSV G protein from Indiana strain having a substitution at positions 47 and 354, by any amino acid except K or R.

SEQ ID NO: 18 corresponds to the full length VSV G protein from Indiana strain having a substitution at position 63, by any amino acid except K or R.

SEQ ID NO: 19 corresponds to the full length VSV G protein from Indiana strain having a substitution at position 370, by any amino acid except K or R.

SEQ ID NO: 20 corresponds to the full length VSV G protein from Indiana strain having a substitution at positions 63 and 370, by any amino acid except K or R.

SEQ ID NO: 21 corresponds to the ectodomain of the VSV G protein from Marraba strain
having a substitution at position 47, by any amino acid except K or R.

SEQ ID NO: 22 corresponds to the ectodomain of the VSV G protein from Marraba strain
having a substitution at position 354, by any amino acid except K or R.

SEQ ID NO: 23 corresponds to the ectodomain of the VSV G protein from Marraba strain having a substitution at positions 47 and 354, by any amino acid except K or R.

SEQ ID NO: 24 corresponds to the full length VSV G protein from Marraba strain having a substitution at position 63, by any amino acid except K or R.

SEQ ID NO: 25 corresponds to the full length VSV G protein from Marraba strain having a substitution at position 370, by any amino acid except K or R.

SEQ ID NO: 26 corresponds to the full length VSV G protein from Marraba strain having a substitution at positions 63 and 370, by any amino acid except K or R.

SEQ ID NO: 27 corresponds to the ectodomain of the VSV G protein from New Jersey strain having a substitution at position 47, by any amino acid except K or R.

SEQ ID NO: 28 corresponds to the ectodomain of the VSV G protein from New Jersey strain having a substitution at position 358, by any amino acid except K or R.

SEQ ID NO: 29 corresponds to the ectodomain of the VSV G protein from New Jersey strain having a substitution at positions 47 and 358, by any amino acid except K or R.

SEQ ID NO: 30 corresponds to the full length VSV G protein from New Jersey strain having a substitution at position 63, by any amino acid except K or R.

SEQ ID NO: 31 corresponds to the full length VSV G protein from New Jersey strain having a substitution at position 374, by any amino acid except K or R.

SEQ ID NO: 32 corresponds to the full length VSV G protein from New Jersey strain having a substitution at positions 63 and 374, by any amino acid except K or R.

SEQ ID NO: 33 corresponds to the ectodomain of the VSV G protein from Carajas strain having a substitution at position 47, by any amino acid except K or R.

SEQ ID NO: 34 corresponds to the ectodomain of the VSV G protein from Carajas strain having a substitution at position 358, by any amino acid except K or R.

SEQ ID NO: 35 corresponds to the ectodomain of the VSV G protein from Carajas strain having a substitution at positions 47 and 358, by any amino acid except K or R.

SEQ ID NO: 36 corresponds to the full length VSV G protein from Carajas strain having a substitution at position 68, by any amino acid except K or R.

SEQ ID NO: 37 corresponds to the full length VSV G protein from Carajas strain having a substitution at position 379, by any amino acid except K or R.

SEQ ID NO: 38 corresponds to the full length VSV G protein from Carajas strain having a substitution at positions 68 and 379, by any amino acid except K or R.

SEQ ID NO: 39 corresponds to the ectodomain of the VSV G protein from Alagoa strain having a substitution at position 47, by any amino acid except K or R.

SEQ ID NO: 40 corresponds to the ectodomain of the VSV G protein from Alagoa strain having a substitution at position 354, by any amino acid except K or R.

SEQ ID NO: 41 corresponds to the ectodomain of the VSV G protein from Alagoa strain having a substitution at positions 47 and 354, by any amino acid except K or R.

SEQ ID NO: 42 corresponds to the full length VSV G protein from Alagoa strain having a substitution at position 64, by any amino acid except K or R.

SEQ ID NO: 43 corresponds to the full length VSV G protein from Alagoa strain having a substitution at position 371, by any amino acid except K or R.

SEQ ID NO: 44 corresponds to the full length VSV G protein from Alagoa strain having a substitution at positions 64 and 371, by any amino acid except K or R.

SEQ ID NO: 45 corresponds to the ectodomain of the VSV G protein from Cocal strain having a substitution at position 47, by any amino acid except K or R.

SEQ ID NO: 46 corresponds to the ectodomain of the VSV G protein from Cocal strain having a substitution at position 354, by any amino acid except K or R.

SEQ ID NO: 47 corresponds to the ectodomain of the VSV G protein from Cocal strain having a substitution at positions 47 and 354, by any amino acid except K or R.

SEQ ID NO: 48 corresponds to the full length VSV G protein from Cocal strain having a substitution at position 64, by any amino acid except K or R.

SEQ ID NO: 49 corresponds to the full length VSV G protein from Cocal strain having a substitution at position 371, by any amino acid except K or R.

SEQ ID NO: 50 corresponds to the full length VSV G protein from Cocal strain having a substitution at positions 64 and 371, by any amino acid except K or R.

SEQ ID NO: 51 corresponds to the ectodomain of the VSV G protein from Morreton strain having a substitution at position 47, by any amino acid except K or R.

SEQ ID NO: 52 corresponds to the ectodomain of the VSV G protein from Morreton strain having a substitution at position 354, by any amino acid except K or R.

SEQ ID NO: 53 corresponds to the ectodomain of the VSV G protein from Morreton strain having a substitution at positions 47 and 354, by any amino acid except K or R.

SEQ ID NO: 54 corresponds to the full length VSV G protein from Morreton strain having a substitution at position 64, by any amino acid except K or R.

SEQ ID NO: 55 corresponds to the full length VSV G protein from Morreton strain having a substitution at position 371, by any amino acid except K or R.

SEQ ID NO: 56 corresponds to the full length VSV G protein from Morreton strain having a substitution at positions 64 and 371, by any amino acid except K or R.

In other word, the invention relates advantageously to an isolated non-naturally occurring protein comprising or consisting of one the following sequences SEQ ID NO: 15-56, wherein Xaa corresponds to any amino acid expect R or K.

Advantageously, the invention relates to the isolated non-naturally occurring protein as defined above, wherein the amino acid at position 47 or at position 354, or at both positions 47 and 354 are substituted by A, G, F or Q, preferably A or Q.

In other word, the invention relates advantageously to an isolated non-naturally occurring protein comprising or consisting of one the following sequences: SEQ ID NO: 15-56, wherein Xaa corresponds to any amino acid expect R or K.

Advantageously, the invention relates to an isolated protein comprising, consisting essentially of, or consisting of one of the following sequences SEQ ID NO: 155-322. In other words, the invention relates advantageously to an isolated protein as defined above comprising, consisting essentially of, or consisting of one of the following sequences SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO:

315, SEQ ID NO: 316, SEQ ID NO: 317, SEQ ID NO: 318, SEQ ID NO: 319, SEQ ID NO: 320, SEQ ID NO: 321 and SEQ ID NO: 322.

More advantageously, the invention relates to the isolated non-naturally occurring protein as defined above, wherein the amino acid at position 8 of SEQ ID NO: 1 or the corresponding positions in the protein derived from said protein as set forth in SEQ ID NO: 1, is substituted by any amino acid except H or Q or Y.

More advantageously, the invention relates to the isolated non-naturally occurring protein as defined above, wherein the amino acid at position 209 of SEQ ID NO: 1 or the corresponding positions in the protein derived from said protein as set forth in SEQ ID NO: 1, is substituted by any amino acid except Y or H.

More advantageously, the invention relates to the isolated non-naturally occurring protein as defined above, wherein said protein comprises or consists essentially of one of the following amino acid sequence: SEQ ID NO 57-154.

SEQ ID NO 57-154 represent proteins wherein the amino acid at position 47 or at position 354, or at both positions 47 and 354, or the corresponding positions in the protein derived from said protein as set forth in SEQ ID NO: 1, are substituted by any amino acid except K or R, and wherein the amino acid at position 8 of SEQ ID NO: 1 or the corresponding positions in the protein derived from said protein as set forth in SEQ ID NO: 1, is substituted by any amino acid except H or Q or preferably except Y the amino acid at position 209 of SEQ ID NO: 1 or the corresponding positions in the protein derived from said protein as set forth in SEQ ID NO: 1, is substituted by any amino acid except Y or H, or the amino acid at position 8 of SEQ ID NO: 1 or the corresponding positions in the protein derived from said protein as set forth in SEQ ID NO: 1, is substituted by any amino acid except H or Q or preferably except Y and the amino acid at position 209 of SEQ ID NO: 1 or the corresponding positions in the protein derived from said protein as set forth in SEQ ID NO: 1, is substituted by any amino acid except Y or H.

More advantageously, the invention relates to the isolated non-naturally occurring protein as defined above, further comprising an insertion of a peptide between the amino acids at positions 192 to 202, or
240 to 257, or
347 to 353, or
364 to 366, or
376 to 379, said peptide originating from a protein different from the protein as set forth in SEQ ID NO: 1. The inventors identified that an insertion of a peptide, said peptide originating from a protein different from the G protein of VSV, within the above mentioned region does not alter the fusion property of the protein according to the invention.

In the invention, an insertion "between the amino acids positions 192 to 202, 240 to 257, 347 to 353, 364 to 366, or 376 to 379" means that the peptide is inserted either between two consecutive amino acids, for instance between the amino acids at positions 192 and 193, 193 and 194, 194 and 195, 195 and 196, 196 and 197, 197 and 198, 198 and 199, 199 and 200, 200 and 201, 201 and 202, 240 and 241, 241 and 242, 242 and 243, 243 and 244, 244 and 245, 245 and 246, 246 and 247, 247 and 248, 248 and 249, 249 and 250, 250 and 251, 251 and 252, 252 and 253, 253 and 254, 254 and 255, 255 and 256, 256 and 257, 347 and 348, 348 and 349, 349 and 350, 350 and 351, 351 and 352, 352 and 353, 364 and 365, 365 and 366, 376 and 377, 377 and 378, and 378 and 379, or between two non-consecutive numbered amino acids due to a deletion of one or more amino acid; for instance a peptide can be inserted between the amino acids at positions 192 and 194, because the amino acid at position 193 was deleted or replaced by the inserted peptide (etc.).

With the above explanations, the skilled person will be able to determine the positions of the insertion encompassed by the invention.

More advantageously, the invention relates to the isolated non-naturally occurring protein as defined above, further comprising an insertion of a peptide between the amino acids at position 351 and 352, said peptide originating from a protein different from the protein as set forth in SEQ ID NO: 1. Advantageously, the invention relates to the isolated non-naturally occurring protein as defined above, further comprising an insertion of a peptide in position 1 (in other words, at the N-terminal extremity, i.e. upstream of the amino acid at position 1), said peptide originating from a protein different from the protein as set forth in SEQ ID NO: 1. In the invention, an insertion of a peptide in position 1 means an insertion of said peptide at the N-terminal extremity of the non-naturally occurring protein as defined above. Thus, in this embodiment, the first amino acid residue of the sequence of said non-naturally occurring protein as defined above is preserved (maintained). In other words, said first amino acid residue at position 1 of the sequence of said non-naturally occurring protein as defined above is not deleted. In an alternative embodiment, the invention relates to the isolated non-naturally occurring protein as defined above, further comprising an insertion of a peptide in replacement of the amino acid residue at position 1, said peptide originating from a protein different from the protein as set forth in SEQ ID NO: 1. Thus, in this alternative embodiment, the first amino acid residue of the sequence of said non-naturally occurring protein as defined above is deleted and replaced (i.e. substituted) with the sequence of said peptide.

Advantageously, the inventors identified that an insertion in position 1 (in other words, at the N-terminal extremity) or between the amino acids 351 and 352 of SEQ ID NO: 1, or the corresponding position in SEQ ID NO: 2-14, and having a mutation at the position 47, or 354 or both, or the corresponding position in SEQ ID NO: 2-14 does not modify the fusion properties of the mutated protein.

Therefore, the inventors propose to insert in the VSV G protein enable to interact with its receptor, between these two amino acids, a tag peptide, a luminescent, a nanobody or any peptide that recognize specifically a membrane protein.

In other words, and with a specific advantage, the inventors therefore propose to provide a mutated VSV G protein, in which is inserted, between the two above mentioned amino acids, any peptide that would allow a specific targeting of cells of interest.

More advantageously, the invention relates to the isolated non-naturally occurring protein as defined above, wherein said peptide is at least a part of a ligand of a cellular receptor.

With the mutated protein according to the invention, in which it is inserted a peptide or a nanobody, it become possible to produce a VSV that specifically target a cell of interest, in particular a tumoral cell, and therefore specifically kill this determined cell by using the oncolytic properties of the virus.

Indeed, in this case, the G protein according to the invention would not interact with its natural receptor (LDL-R) but will recognize a receptor which is a target to the peptide inserted between the amino acids at position 351 and 352 of SEQ ID NO: 1, or the corresponding positions in SEQ ID NO: 2-14. As the protein according to the invention retains its fusogenic properties, the protein would allow the virus entry, and the virus could therefore kill the targeted cell.

For instance, the inserted peptide could be an anti-HER2 nanobody, an anti-MUC18 nanobody or an anti-PD-1 nanobody.

The invention also relates to a nucleic acid molecule coding for an isolated non-naturally occurring protein as defined above.

In other words, the invention relates to a nucleic acid molecule coding for any protein as set forth in SEQ ID NO: 15-322, as defined above.

In another aspect, the invention relates to a recombinant virus expressing an isolated non-naturally occurring protein as defined above. An advantageous virus is a VSV expressing all the viral protein in their wild type form except the G protein which corresponds to the mutated protein according to the invention.

Advantageously, the invention relates to a recombinant virus comprising a nucleic acid molecule as defined above.

The invention also relates to a eukaryotic cell containing or expressing a non-naturally occurring protein as defined above, or containing a nucleic acid molecule as defined above. Advantageously, the invention relates to a eukaryotic cell infected by a virus as defined above.

The invention also relates to a composition comprising one at least of the followings:
a protein according as defined above; or
a nucleic acid molecule as defined above;
a virus as defined above; or,
a eukaryotic cell as defined above.

In particular, the invention relates to a composition comprising a virus coding for a G protein comprising or consisting of one of the following sequences SEQ ID NO: 15-322.

The invention also relates to a composition comprising one at least of the followings:
a protein according as defined above; or
a nucleic acid molecule as defined above;
a virus as defined above; or,
a eukaryotic cell as defined above,
for its use as drug.

In particular, the invention relates to a composition comprising a virus coding for a G protein comprising or consisting of one of the following sequences SEQ ID NO: 15-322, for its use as drug.

Advantageously, the invention relates to the composition as defined above, for its use for treating cancer.

As mentioned above, a virus expressing a mutated protein according to the invention can be used to specifically target a determined cell and therefore to specifically kill them.

The invention relates to the in vitro use of a protein as defined above, anchored in surface, advantageously, a lipid membrane for targeting said surface, advantageously a lipid membrane, to a specific target, for instance a cell, in particular a cell to be killed, such as a cancer cell.

In the invention, it is proposed to use in vitro a protein according to the invention which is anchored to a membrane to specifically address such membrane to a target destination. For instance, the mutated protein according to the invention can be anchored in the membrane of a liposome, of a vesicle, of an exosome, on a capsule, on a nanoparticle . . . such that the protein according to the invention can specifically target this liposome, vesicle, capsule or nanoparticle to a specific target, for instance a cell, in particular a cell to be killed, such as a cancer cell.

This use is particularly advantageous in a drug-delivery targeting purpose, wherein the protein according to the invention allow a specific target of a drug.

The drug can be a therapeutic molecule, a protein, and a nucleic acid.

The invention relates to a protein as defined above, anchored in a surface, advantageously, a lipid membrane, for use for targeting said surface, advantageously a lipid membrane, to a specific target, for instance a cell, in particular a cell to be killed, such as a cancer cell.

In the invention, it is proposed a protein according to the invention which is anchored to a membrane for use to specifically address such membrane to a target destination. For instance, the mutated protein according to the invention can be anchored in the membrane of a liposome, of a vesicle, of an exosome, on a capsule, on a nanoparticle . . . such that the protein according to the invention can specifically target this liposome, vesicle, capsule or nanoparticle to a specific target, for instance a cell, in particular a cell to be killed, such as a cancer cell.

This use is particularly advantageous in a drug-delivery targeting purpose, wherein the protein according to the invention allows to specifically target a drug to a specific target, for instance a cell, in particular a cell to be killed, such as a cancer cell.

Thus, the invention relates to a mutated protein according to the invention for use as a drug delivery-system, wherein said mutated protein is anchored in the membrane of a liposome, or of a vesicle, or of an exosome, or on a capsule, or on a nanoparticle.

The drug can be a therapeutic molecule, a protein, and a nucleic acid.

BRIEF DESCRIPTION OF THE FIGURES

The invention will be better understood from the following figures and examples.

Legend to the Figures

Figure 4A:
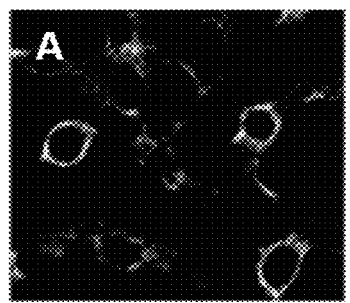
FIGS. 4A-4I are photographs of labelling of G at the surface of BSR cells infected with VSV using fluorescent GST-CR1ATTO550, GST-CR2ATTO550 and GST-CR3ATTO550. At 4 h post infection, cells were incubated with the appropriate GST-CRATTO550 at 4° C. during 30 minutes prior fixation and permeabilization and then immuno-labelled using an anti-VSV N antibody to visualize the infection. DAPI was used to stain the nuclei. Scale bars 20 µm.

FIG. 4A represents the labelling of cells using anti-VSV N antibody.

Figure 4B:
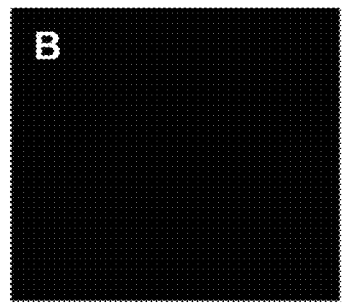

FIG. 4B represents the labelling of cells using the fluorescent GST-CR1ATTO550.

Figure 4C:
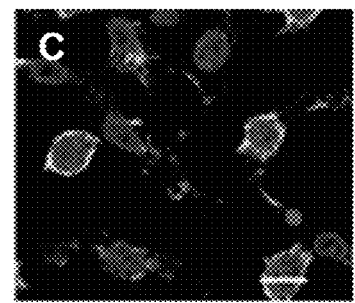
Figure 6A:
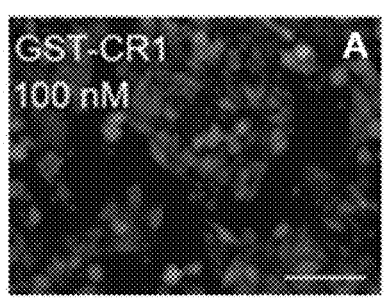
Figure 6B:

FIG. 4C represent the superposition of the fluorescence in FIG. 6A and FIG. 6B.

Figure 4D:
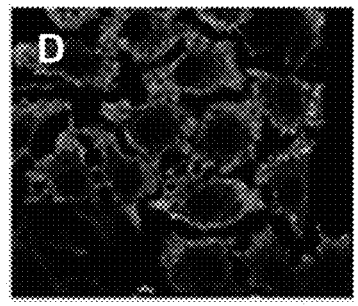

FIG. 4D represents the labelling of cells using anti-VSV N antibody.

Figure 4E:
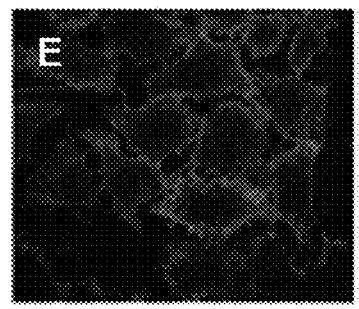

FIG. 4E represents the labelling of cells using the fluorescent GST-CR2ATTO550.

Figure 4F:
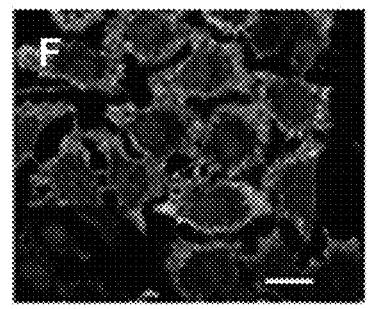
Figure 6C:
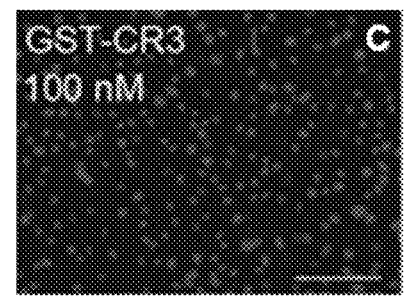
Figure 6D:
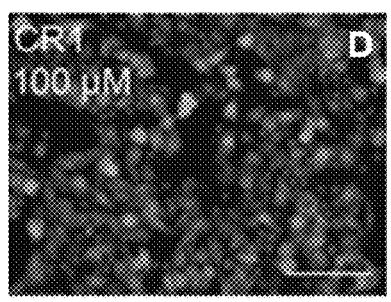
Figure 6E:
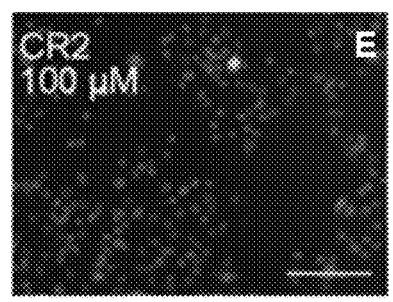

FIG. 4F represent the superposition of the fluorescence in FIG. 6D and FIG. 6E.

Figure 4G:
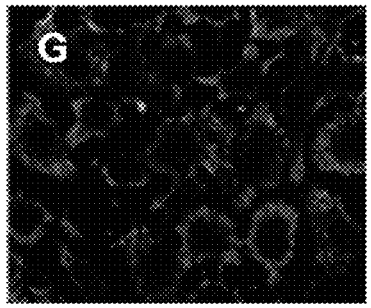

FIG. 4G represents the labelling of cells using anti-VSV N antibody.

Figure 4H:
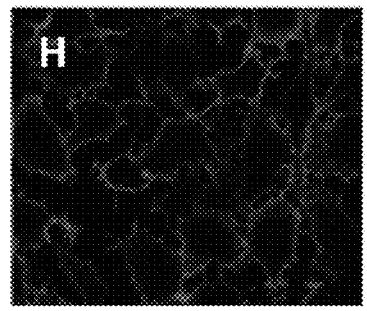

FIG. 4H represents the labelling of cells using the fluorescent GST-CR3ATTO550.

Figure 4I:
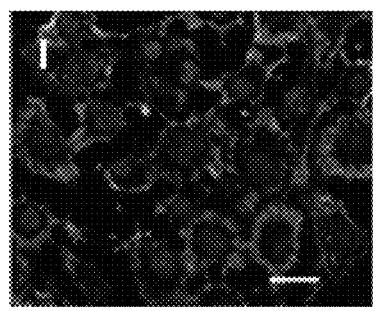

FIG. 4I represent the superposition of the fluorescence in FIG. 6G and FIG. 6H.

Figure 5:
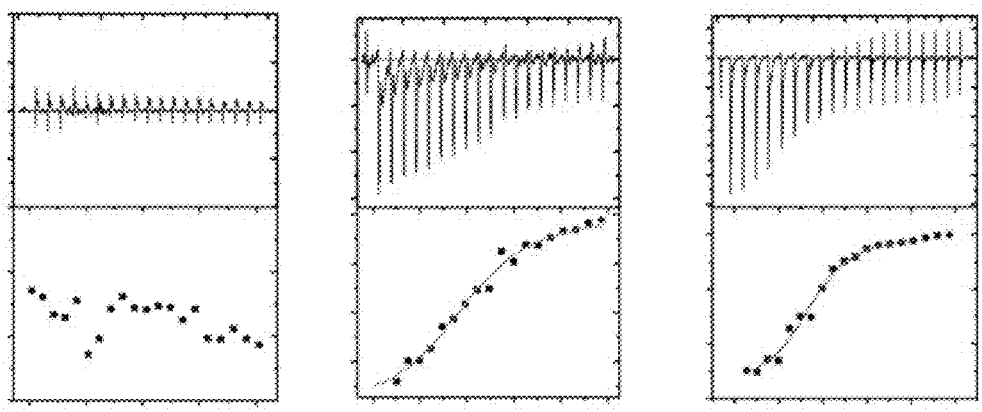

FIG. 5 represents representative plots of each Isothermal titration calorimetry (ITC) analyses between Gth and CR1, Gth and CR2, Gth and CR3 at 20° C. Binding parameters were determined by curve fitting analysis with a single-site binding model. The values indicated in the panel are those corresponding to the curves that are presented. Kd values given in the text are means of 3 independent experiments +/−standard errors. B-C Inhibition of VSV infection by soluble forms of CR domains. Upper x-axis: time (min); upper Y-axis: µcal/s; lower x-axis: molar ratio and lower y-axis: kcal.mol$^{-1}$ of injectant. Left panel: CR1, middle panel: CR2 and right panel: CR3.

FIGS. 6A-6F represents photographs of BSR cells infected with VSV-eGFP preincubated with GST-CR1, GST-CR2, GST-CR3 (A-C), CR1, CR2, or CR3 monovalent domains (D-F) at the indicated concentrations. Cells were fixed 4 h post infection. Only infected cells are expressing eGFP. Neither CR1 nor GST-CR1 construction protect cells from infection. DAPI was used to stain the nuclei. Scale bars 100 µm.

FIG. 6A represents photograph of BRS cells infected with VSV-eGFP preincubated with GST-CR1 at the indicated concentrations.

FIG. 6B represents photograph of BRS cells infected with VSV-eGFP preincubated with GST-CR2 at the indicated concentrations.

FIG. 6C represents photograph of BRS cells infected with VSV-eGFP preincubated with GST-CR3 at the indicated concentrations.

FIG. 6D represents photograph of BRS cells infected with VSV-eGFP preincubated with CR1 monovalent domain at the indicated concentrations.

FIG. 6E represents photograph of BRS cells infected with VSV-eGFP preincubated with CR2 monovalent domain at the indicated concentrations.

Figure 6F:
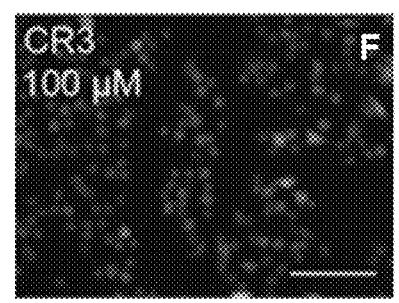

FIG. 6F represents photograph of BRS cells infected with VSV-eGFP preincubated with CR3 monovalent domain at the indicated concentrations.

Figure 7:
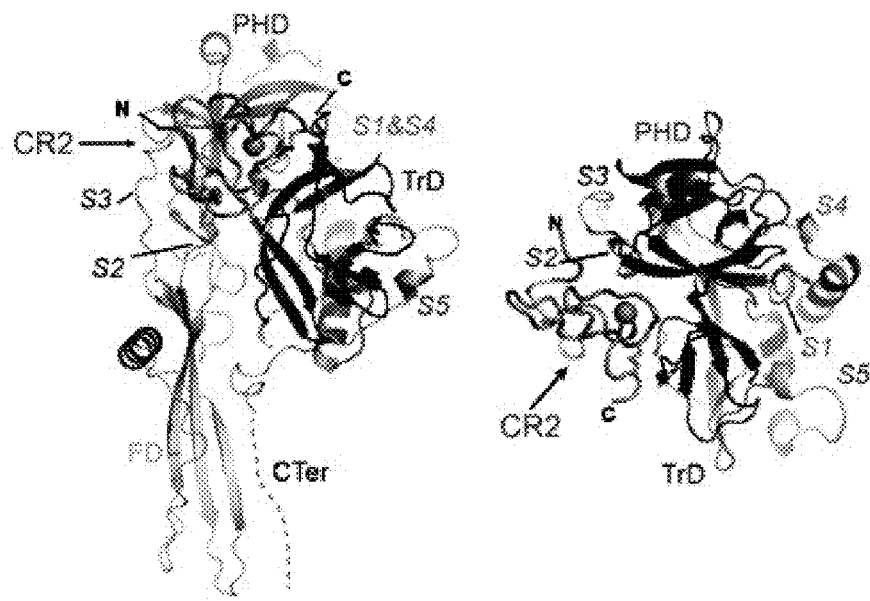

FIG. 7 is a tridimensional representation of GthCR2 crystalline structures in ribbon representation.

Figure 8:
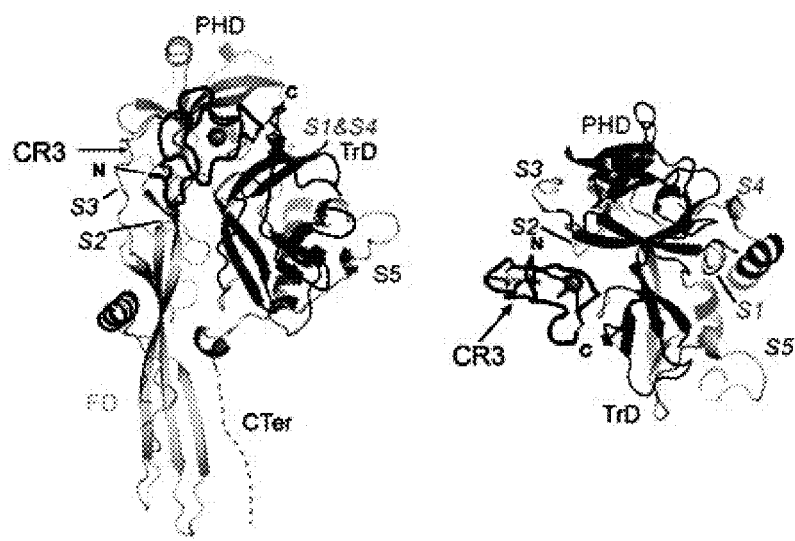

FIG. 8 is a tridimensional representation of GthCR3 crystalline structures in ribbon representation.

In both complexes the CR domain is nested in the same cavity of G. N- and C-terminal extremities of each CR are indicated. The trimerization domain (TrD) the pleckstrin homology domain (PHD) and the fusion domain (FD) of Gth are represented.

Figure 9:
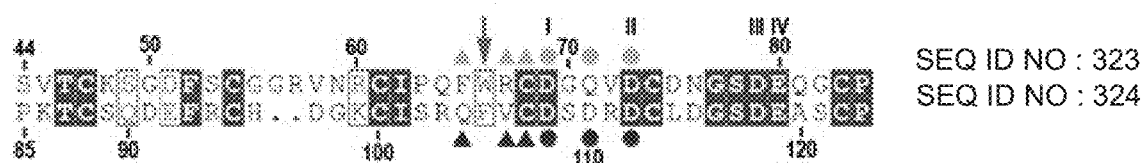

FIG. 9 is a sequence alignment of LDL-R CR2 and CR3. Conserved residues are in a grey box and similar residues are boxed. Acidic residues involved in the binding of the $Ca^{2+}$ ion are indicated by I, II, III, and IV. CR residues involved in polar contacts with G are labelled with grey symbols (light grey for CR2 and black for CR3; dots when the contact is established via the lateral chain and triangles when the contact is established via the main chain) on each CR sequence. The aromatic residue which protrudes from the CR modules and establishes hydrophobic interactions with G is indicated by the arrow.

Figure 10A:
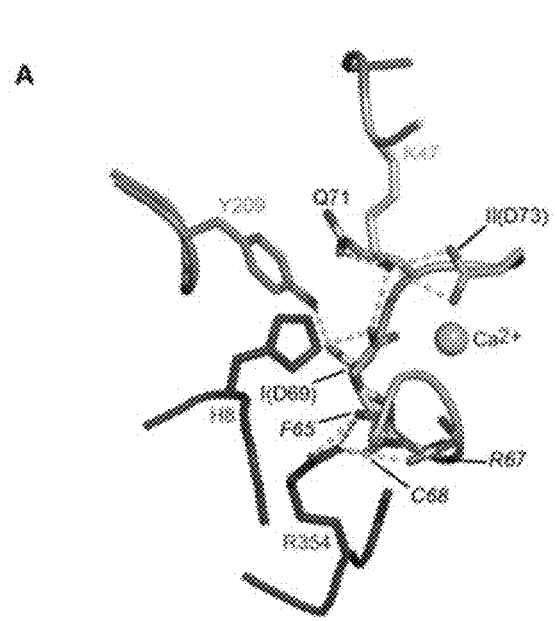

FIG. 10A corresponds to a close-up view on the Gth-CR interface showing the docking of G basic residues on the acidic patch of CR2. The G residues H8, K47, Y209 and R354 are involved in the interaction. Residues labels on each CR domain are in italic letters when the contact is established via the main chain; putative bonds are shown as light grey dashed lines.

Figure 10B:
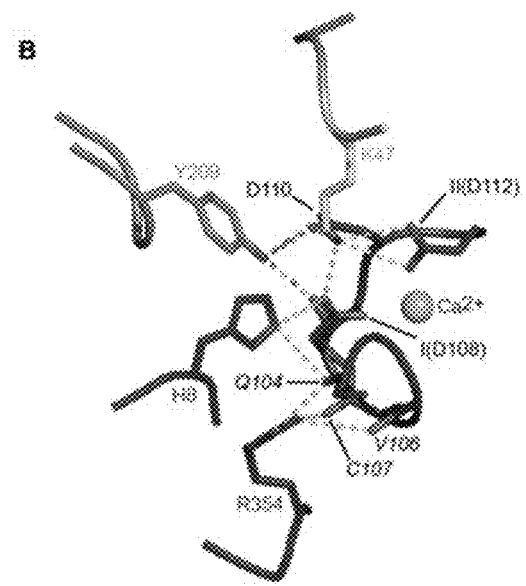

FIG. 10B corresponds to a close-up view on the Gth-CR interface showing the docking of G basic residues on the acidic patch of CR3. The G residues H8, K47, Y209 and R354 are involved in the interaction. Residues labels on each CR domain are in italic letters when the contact is established via the main chain; putative bonds are shown as light grey dashed lines.

Figures 11A, 11B, 11C, 11D:
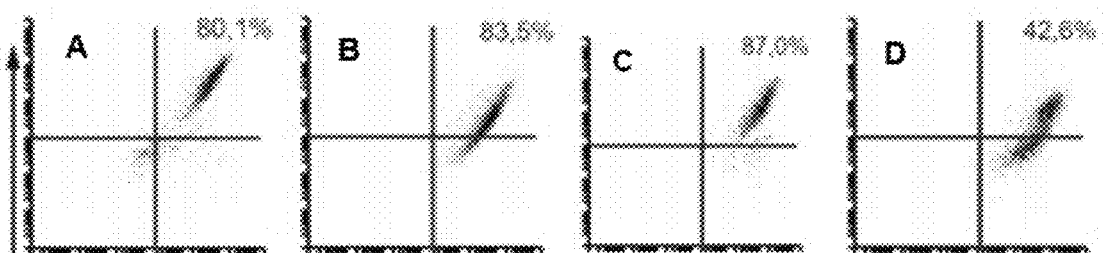
Figures 11E, 11F, 11G, 11H:
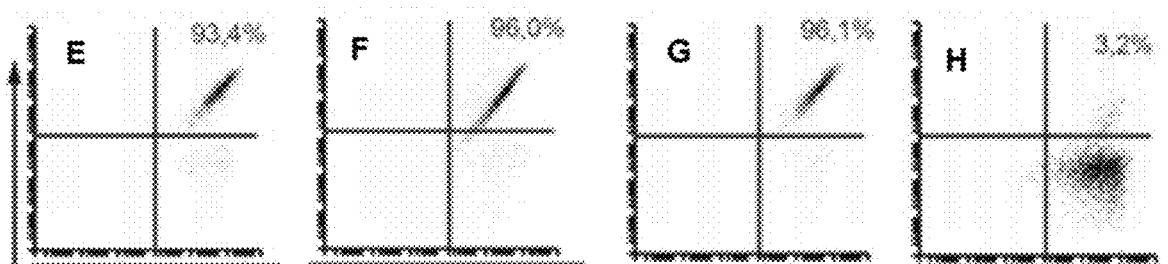
Figures 11I, 11J, 11K:
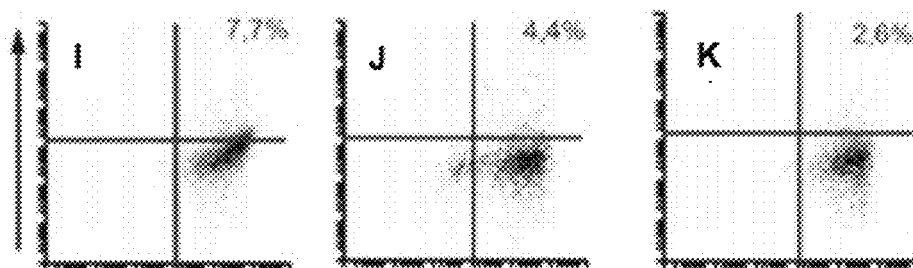
Figures 11L, 11M, 11N:
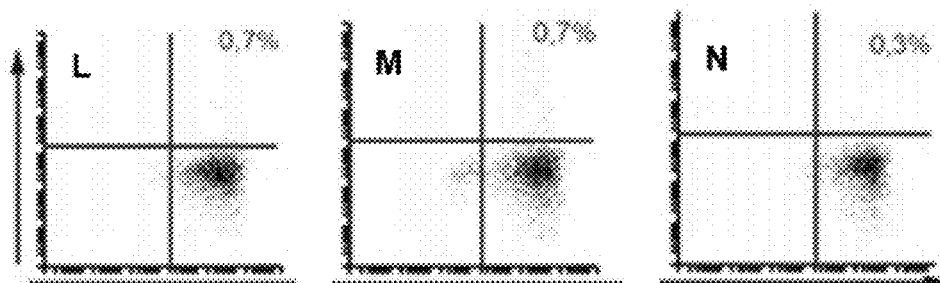

FIGS. 11A-11N represent flow cytometry analysis of the expression of WT and mutant glycoproteins at the surface of HEK293T cells and of the binding of fluorescent GST-CR2 (A-D and I-K) and GST-CR3 (E-H and L-M). After 24 h of transfection, cell surface expression of WT and mutant G was assessed using monoclonal anti-G antibody 8G5F11 directly on living cells at 4° C. during 1 h. Cells were then incubated simultaneously with anti-mouse Alexa fluor 488 and the indicated GST-CRATTO550 dye. Cells transfected with a G construct that was still able to bind GST-CR domains exhibited red fluorescence due the ATTO550 dye. In each plot, the percentage of ATTO550 positive cells is indicated.

FIG. 11A represents the experiment of binding of fluorescent GST-CR2 with WT glycoprotein.

FIG. 11B represents the experiment of binding of fluorescent GST-CR2 with the glycoprotein H8A mutant.

FIG. 11C represents the experiment of binding of fluorescent GST-CR2 with the glycoprotein Y209A mutant.

FIG. 11D represents the experiment of binding of fluorescent GST-CR2 with the glycoprotein K47A mutant.

FIG. 11E represents the experiment of binding of fluorescent GST-CR3 with WT glycoprotein.

FIG. 11F represents the experiment of binding of fluorescent GST-CR3 with the glycoprotein H8A mutant.

FIG. 11G represents the experiment of binding of fluorescent GST-CR3 with the glycoprotein Y209A mutant.

FIG. 11H represents the experiment of binding of fluorescent GST-CR3 with the glycoprotein K47A mutant.

FIG. 11I represents the experiment of binding of fluorescent GST-CR2 with the glycoprotein K47Q mutant.

FIG. 11J represents the experiment of binding of fluorescent GST-CR2 with the glycoprotein R354A mutant.

FIG. 11K represents the experiment of binding of fluorescent GST-CR2 with the glycoprotein R354Q mutant.

FIG. 11L represents the experiment of binding of fluorescent GST-CR3with the glycoprotein K47Q mutant.

FIG. 11M represents the experiment of binding of fluorescent GST-CR3 with the glycoprotein R354A mutant.

FIG. 11N represents the experiment of binding of fluorescent GST-CR3 with the glycoprotein R354Q mutant.

Figure 12:
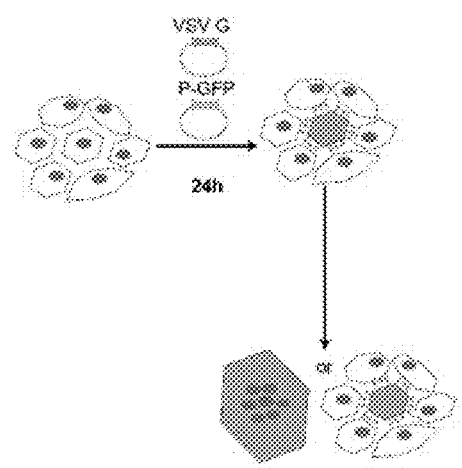

FIG. 12 is a schematic representation of the cell-cell fusion assay. BSR cells are co-transfected with plasmids expressing VSV G (either WT or mutant G) and P-GFP (a cytoplasmic marker). 24 h post-transfection cells are exposed for 10 min to media adjusted to the indicated pH which is then replaced by DMEM at pH 7.4. The cells are then kept at 37° C. for 1 h before fixation. Upon fusion, the P-GFP diffuses in the syncytia.

Figure 13A:
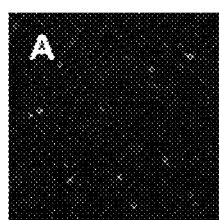

FIGS. 13A-13X are photographs corresponding to the results of the experiment described in FIG. 12.

FIG. 13A represents the result of experiments with empty vector at pH 5.0.

Figure 13B:
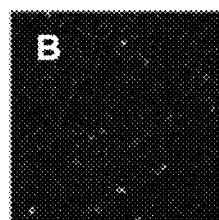

FIG. 13B represents the result of experiments with empty vector at pH 5.5.

Figure 13C:
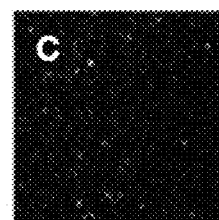

FIG. 13C represents the result of experiments with empty vector at pH 6.0.

Figure 13D:
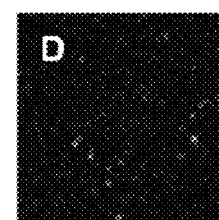

FIG. 13D represents the result of experiments with empty vector at pH 6.5.

Figure 13E:
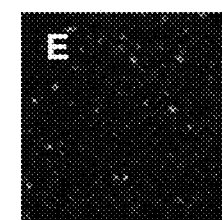

FIG. 13E represents the result of experiments with empty vector at pH 7.0.

Figure 13F:
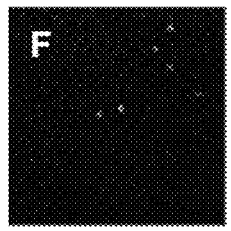

FIG. 13F represents the result of experiments with empty vector at pH 7.5.

Figure 13G:
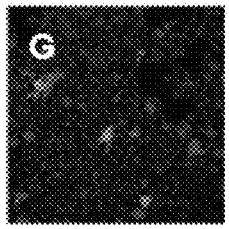

FIG. 13G represents the result of experiments with vector expressing K47A mutant at pH 5.0.

Figure 13H:
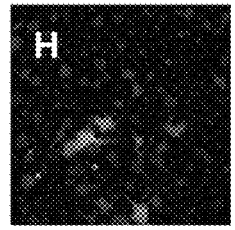

FIG. 13H represents the result of experiments with vector expressing GK47A mutant at pH 5.5.

Figure 13I:
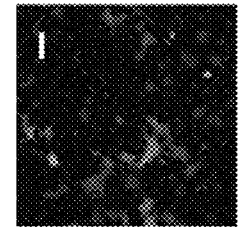

FIG. 13I represents the result of experiments with vector expressing K47A mutant at pH 6.0.

Figure 13J:
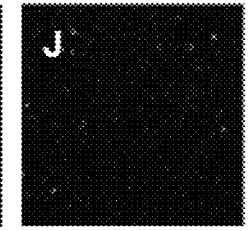

FIG. 13J represents the result of experiments with vector expressing K47A mutant at pH 6.5.

FIG. 13K represents the result of experiments with vector expressing K47A mutant at pH 7.0.

FIG. 13L represents the result of experiments with vector expressing K47A mutant at pH 7.5.

FIG. 13M represents the result of experiments with vector expressing R354A mutant at pH 5.0.

FIG. 13N represents the result of experiments with vector expressing R354A mutant at pH 5.5.

FIG. 13O represents the result of experiments with vector expressing R354A mutant at pH 6.0.

FIG. 13P represents the result of experiments with vector expressing R354A mutant at pH 6.5.

FIG. 13Q represents the result of experiments with vector expressing R354A mutant at pH 7.0.

FIG. 13R represents the result of experiments with vector expressing R354A mutant at pH 7.5.

FIG. 13S represents the result of experiments with vector expressing WT G protein at pH 5.0.

FIG. 13T represents the result of experiments with vector expressing WT G protein at pH 5.5.

FIG. 13U represents the result of experiments with vector expressing WT G protein at pH 6.0.

FIG. 13V represents the result of experiments with vector expressing WT G protein at pH 6.5.

FIG. 13W represents the result of experiments with vector expressing WT G protein at pH 7.0.

FIG. 13X represents the result of experiments with vector expressing WT G protein at pH 7.5.

Figure 14:
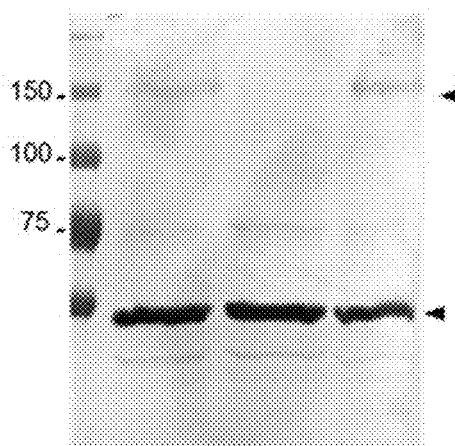

FIG. 14 represent an analysis of LDL-R expression in wild-type HAP-1 cells (A), LDL-RKO HAP-1 (B) cells and HEK293T (C). The immunoblot was performed on crude cell extracts and revealed with anti LDL-R (EP1553Y-1.). Tubulin (tub) was also immunoblotted as a loading control (2.).

Figure 15:
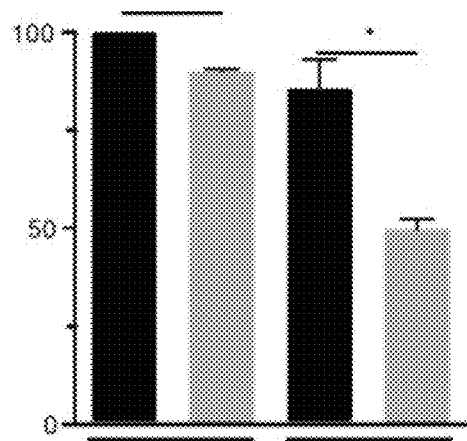

FIG. 15 is an histogram showing the effect of the RAP protein on the susceptibility of LDL-R deficient HAP-1 cells to VSV-eGFP infection. VSV-eGFP was used to infect HAP-1 (A) and HAP-1 LDL-RKO (B) cells in presence of RAP (grey column) or not (black column). Infectivity was determined by counting the number of cells expressing eGFP using a flow cytometer. Data depict the mean with standard error for experiments performed in triplicate. p values were determined using an unpaired Student t test (* $p<0.01$; *** non-significant).

Figure 16:
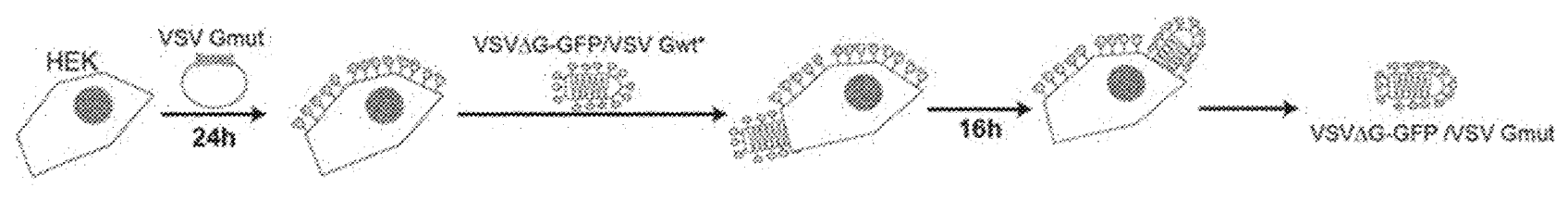

FIG. 16 is a schematic representation of the generation of VSVΔG-GFP virus pseudotyped with VSV G mutants. Transfected HEK-293T cells expressing mutant G at their surface were infected with VSVΔG-GFP pseudotyped with VSV G wild type. After 16 h of infection, VSVΔG-GFP virions pseudotyped with mutant VSV G were harvested from the supernatant.

Figure 17:
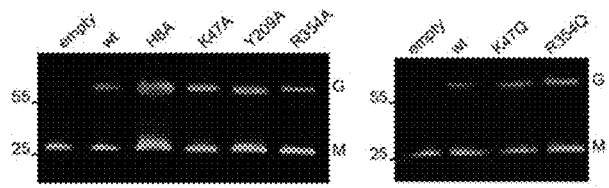

FIG. 17 represents the incorporation of wild type and mutant G in VSVΔG-GFP viral particles. VSVΔG-GFP pseudotyped with the wild type VSV G was used to infect HEK-293T cells transfected with the indicated mutant (MOI 1). At 16 h post infection, viral supernatants were collected, concentrated and analyzed by Western blot (using an anti-VSV G and an anti-VSV M antibody).

Figure 18:
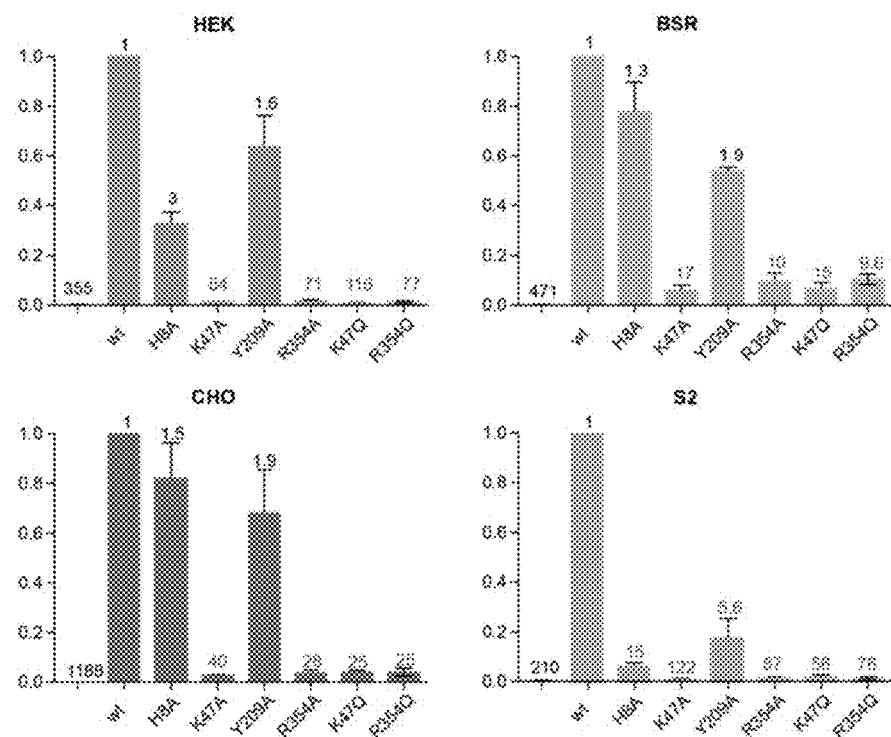

FIG. 18 represents histograms showing the infectivity of VSVΔG-GFP pseudotyped with WT and mutant glycoproteins. VSVΔG-GFP pseudotyped with WT VSV G was used to infect HEK-293T cells previously transfected with the indicated mutated glycoprotein (MOI 1). VSVΔG-GFP viruses pseudotyped by WT or mutant glycoproteins were used to infect HEK-293T, BSR, CHO and S2 cells during 6 h; the percentage of infected cells was determined by counting GFP expressing cells by flow cytometry. Data depict the mean with standard error for three independent experiments. Above each bar, the reduction factor of the titer (compared to VSVΔG-GFP, pseudotyped by WT G which was normalized to 1) is indicated.

Figure 19:
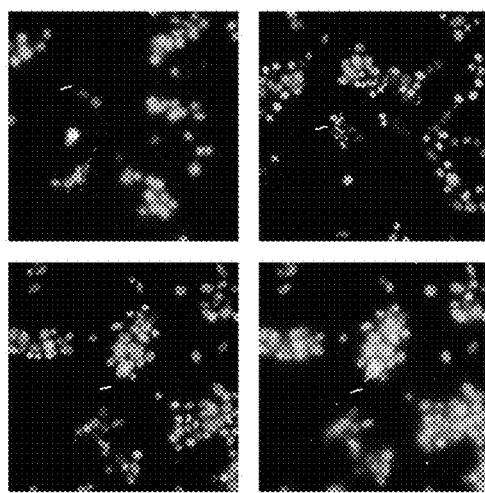

FIG. 19 are photographies of HEK293T cells transfected with a pCAGGS plasmid encoding for VSV glycoprotein modified by the insertion of the mCherry protein in Nterminal extremity (position 1 of the mature protein) and by the insertion of the mCherry protein in between AA 351 and 352. Red fluorescence is present at the cell surface in both case indicating that the protein was correctly refolded and transported throw the Golgi apparatus. This suggests that those two positions on G are potentially interesting to insert any peptide.

EXAMPLES

Example 1

Structural Basis of Low-Density Lipoprotein Receptor Recognition by VSV Glycoprotein The inventors identified that VSV G is able to independently bind two distinct CR (cysteine-rich) domains (CR2 and CR3) of LDL-R and they report crystal structures of VSV G in complex with those domains. The structures reveal that the binding sites of CR2 and CR3 on G are identical. We show that HAP-1 cells in which the LDL-R gene has been knocked out are still susceptible to VSV infection confirming that VSV G can use receptors other than LDL-R for entry. However, mutations of basic residues, which are key for interaction with LDL-R CR domains, abolish VSV infectivity in mammalian as well as insect cells. This indicates that the only receptors of VSV in mammalian and in insect cells are members of the LDL-R family and that VSV G has specifically evolved to interact with their CR domains.

LDL-R CR2 and CR3 domains bind VSV G and neutralize viral infectivity

Figure 1:
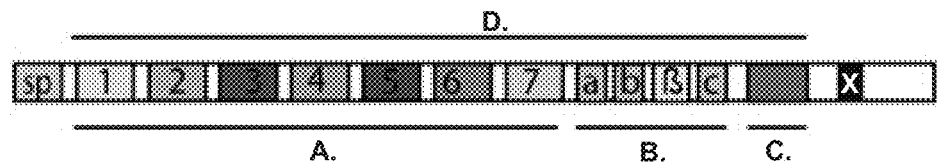
FIG. 1 is a schematic representation of the modular organization of the LDL-R indicating the 7 CR modules (1 to 7), the 3 EGF repeats (a b and c), the seven-bladed β-propeller domain (β) of the epidermal growth factor precursor like domain (B.), and the C-terminal domain containing O-linked oligosaccharides (C.). SP=signal peptide; X=transmembrane domain. A.: CR domains and D.: ectodomain.
Figure 2:
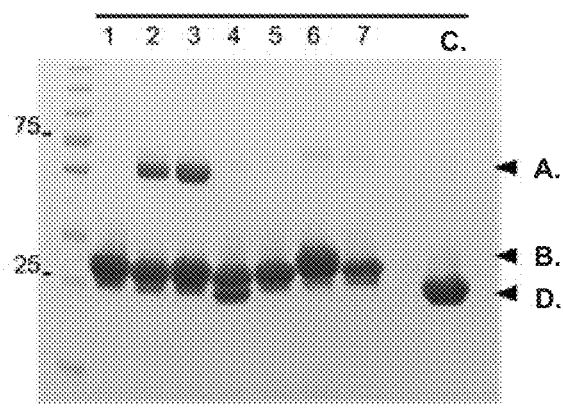
FIG. 2 represents a result of a SDS PAGE analysis of interaction experiments between the 7 GST-CR domains (1-7), bounded to GSH magnetic beads, and Gth at pH 8. C. represents control. The migration position of the proteins are indicated by an arrow: A.: Gth, B.: CRx-GST and D.: GST.
Figure 3:
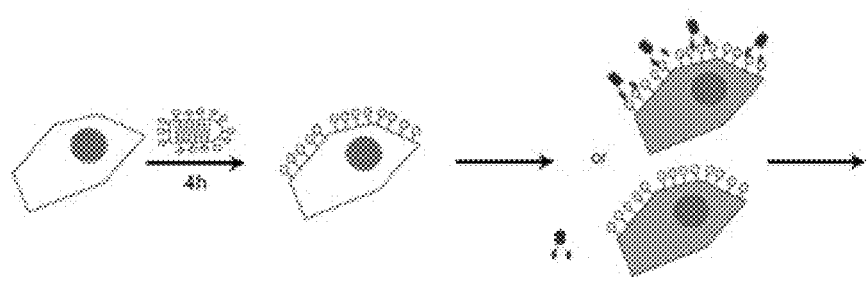
FIG. 3 illustrates the experiments presented in FIG. 6 and FIG. 7. After 4 h of infection, BSR cells were labelled with an antibody directed against VSV nucleoprotein (Anti VSV N) to visualize the infection (green fluorescence) and a GST-CRATTO550 to probe CR domain recognition by the surface displayed glycoprotein (red fluorescence).

The inventors have expressed individually each LDL-R CR domain in fusion with the glutathione S-transferase (GST) in E. coli. Each fusion protein was incubated at pH 8 with magnetic beads coated with glutathione before addition of a soluble form of the ectodomain of G (VSV Gth, amino acid (AA) residues 1-422, generated by thermolysine limited proteolysis of viral particles (FIG. 2). After 20 minutes of incubation at 4° C., the beads were washed and the associated proteins were analyzed by SDS/PAGE followed by Coomassie blue staining. This revealed that only CR2 and CR3 domains are able to directly bind VSV G (FIG. 2) at pH 8. Additionally, GST-CR2 and GST-CR3 (but not GST-CR1) fluorescently labeled with ATTO550 (FIG. 3 and FIG. 4) specifically recognized VSV G expressed at the surface of infected cells. The inventors also used isothermal titration calorimetry (ITC) to investigate the binding parameters of CR1, CR2 and CR3 to Gth in solution (FIG. 5). Here again, no interaction between G and CR1 was detected. On the other hand, for both CR2 and CR3, the binding reactions appear to be exothermic, show a 1:1 stoichiometry and exhibit similar Kds (4.3 +/−1 µM for CR3 and 7.3 +/−1.5 µM for CR2).

Furthermore, recombinant soluble CR2 and CR3 domains, either alone or in fusion with GST, are also able to neutralize viral infectivity when incubated with the viral inoculum prior infection (FIGS. 6).

Crystal structures of VSV G ectodomain in complex with LDL-R CR domains

The inventors crystallized Gth in complex with either CR2 or CR3. The binding site of CR domains on G is the same in both crystal forms (FIG. 7 and FIG. 8).

Two basic residues of G (H8 from the TrD and K47 from PHD) are pointing toward two acidic residues which belong to the octahedral calcium cage of the CR domains (D69 and D73 on CR2; D108 and D112 on CR3 labelled I and II—FIG. 9). Together with Y209 and R354, they seem to be key for the interaction (FIGS. 10A and B).

K47 and R354 are key residues of G required for LDL-R CR domains binding

To investigate their contribution to LDL-R CR domains binding, the inventors mutated residues H8, K47, Y209 and R354 of G into an alanine or a glutamine. HEK293T cells were transfected with a plasmid encoding wild-type or mutant VSV G glycoproteins (WT, H8A, K47A, K47Q, Y209A, R354A and R354Q). Twenty-four hours post-transfection, the cells were incubated with a MAb against G ectodomain. Then, green fluorescent anti IgG secondary antibodies and GST-CR fusion proteins fluorescently labelled with ATTO550 were simultaneously added. Immunofluorescence labelling indicated that WT and all G mutants are efficiently transported to the cell surface (FIGS. 11). Mutants H8A and Y209A bind GST-CR domains as WT G whereas the other mutants are affected in their binding ability (FIGS. 11). Mutants K47Q, R354A and R354Q bind neither GST-CR2 nor GST-CR3. Finally, although no interaction is detected between mutant K47A and CR3, a residual binding activity is observed between this mutant and CR2 (FIGS. 11).

The inventors also checked the fusion properties of mutants K47A and R354A. For this, BSR cells were transfected with pCAGGS plasmids encoding wild-type or mutant VSV G glycoproteins (WT, K47A and R354A). The cells expressing mutant G protein have a fusion phenotype similar to that of WT G (FIGS. 13). This confirms that the mutant glycoproteins are correctly folded and demonstrates that it is possible to decouple G fusion activity and receptor recognition.

Other LDL-R family members are alternative receptors of VSV

HAP-1 cells in which the LDL-R gene has been knocked out (HAP-1 LDL-RKO) (FIG. 14) are as susceptible to VSV infection as WT HAP-1 cells (FIG. 15). This demonstrates that VSV receptors other than the LDL-R are present at the surface of HAP-1 cells.

To evaluate the role of other LDL-R family members as VSV receptors, the inventors took advantage of the properties of the receptor-associated protein (RAP), a common ligand of all LDL-R family members which blocks ligand binding to all LDL-R family members with the exception of LDL-R itself (Finkelshtein et al., 2013). RAP significantly inhibits VSV infection in HAP-1 LDL-RKO but not in WT HAP-1 cells (FIG. 15). Those results are consistent with previous data suggesting that VSV can use other LDL-R family members as alternative receptors (Finkelshtein et al., 2013).

G mutants affected in their CR domain binding site cannot rescue a recombinant VSV lacking the G gene The inventors then examined whether the mutant glycoproteins described above are able to sustain viral infection. The inventors used a recombinant VSV (VSVΔG-GFP) in which the G envelope gene was replaced by the green fluorescent protein (GFP) gene and which was pseudotyped with the VSV G glycoprotein. This pseudotyped recombinant was used to infect HEK cells either transfected or not transfected by a plasmid encoding WT or mutant glycoproteins (Ferlin et al., 2014). After 8 h, the infected cells supernatant was collected (FIG. 16). Mutant glycoproteins incorporation into the envelope of the particles present in the supernatant was verified by western blot (FIG. 17) and the infectivity of the pseudotyped particles was analyzed in different cell lines (mammalian HEK, BSR, CHO and Drosophila S2 cells) by counting the cells expressing GFP by flow cytometry 4 h post-infection (p.i.) (FIG. 18). Mutants K47A, K47Q, R354A and R354Q did not rescue the infectivity of VSVΔG-GFP. Compared to WT G, the infectivity decreased by a factor of 10 up to 120 (FIG. 18). The decrease was more important in HEK and S2 cell lines than in the two hamster cell lines. In mammalian cell lines, mutants H8A and Y209A can rescue the infectivity of VSVΔG-GFP, but at a lower level than that of WT. In S2 cell line, their infectivity is significantly decreased (by a factor of 15 for mutant H8A and ~6 for Y209A) (FIG. 18).

As the fusion activity of the mutants is unaffected, the loss of infectivity of pseudotypes bearing a mutant glycoprotein can be safely attributed to their disability to recognize a cellular receptor. These results indicate that mutants K47A, K47Q, R354A and R354Q which are unable to bind LDL-R CR domains are also severely impaired in their ability to bind other VSV receptors.

Discussion

LDL-R has been demonstrated to be the major entry port of VSV and lentivirus pseudotyped by VSV-G (Finkelshtein et al., 2013). Here, the inventors demonstrate that VSV-G is able to bind two CR domains of the LDL-R with similar affinities. The biological relevance of this interaction was demonstrated by the ability of both CR2 and CR3 to inhibit VSV infection. The crystal structures of VSV G in complex with CR2 and CR3 reveal that they both occupy the same site at the surface of the glycoprotein in its pre-fusion conformation and that the same G residues ensure the correct anchoring of the CR domains. This binding site is split apart when G is in its post-fusion conformation, which explains why G is unable to bind CR domains at low pH. This may disrupt the interaction between G and LDL-R in the endosomal lumen and favour the transport of the virion to an appropriate fusion site.

CR domain recognition by VSV G involves basic residues K47 and R354 pointing toward the calcium-coordinating acidic residues. This mode of binding is very similar to what is observed for endogenous ligand recognition by CR domains of the LDL-R family members and, indeed, mutant glycoproteins in which either K47 or R354 is replaced by an alanine or a glutamine, are unable to bind CR domains. It is worth noting that those key residues are not conserved among vesiculoviruses. Therefore, the use of LDL-R as a viral receptor cannot be generalized to the other members of the genus. Indeed, the inventors have shown that CHAV G, which does not possess basic residues in positions corresponding to VSV residues 47 and 354, does not bind CR domains.

The inventor's functional analysis confirms that LDL-R is not the only receptor of VSV as HAP-1 LDL-RKO can be infected as efficiently as HAP-1 cells. However, the mutant glycoproteins which are unable to bind CR domains cannot restore VSVΔG-GFP infectivity neither in mammalian nor in insect cells. The most parsimonious interpretation of this result is that the only receptors of VSV in HEK cells are members of the LDL-R family. The molecular basis of the interaction is the same for all those receptors and involves G ability to bind their CR domains. This is in agreement with the decrease of infectivity observed in presence of RAP protein which is an antagonist of other members of the LDL-R family. Overall this study demonstrates that VSV G has specifically evolved to interact with CR domains of the members of the LDL-R family. The ubiquitous nature of this receptor family (which is also widespread among invertebrates) explains the pantropism of VSV.

The demonstration that the receptors of VSV are all members of the LDL-R family together with the characterization of the molecular basis of CR domains recognition by G paves the way to develop recombinant VSVs with modified tropism. Indeed, a glycoprotein having (i) a point mutation which ablates the natural receptor tropism and (ii) an insertion of a protein domain or a peptide targeting specifically a tumor cell (Ammayappan et al., 2013) should allow the design of fully retargeted oncolytic VSVs. Such viruses should be able to eliminate cancerous cells while sparing normal ones.

Cells and Viruses

BSR, a clone of BHK-21 (Baby Hamster Kidney cells; ATCC CCL-10) and HEK-293T (human embryonic kidney cells expressing simian virus 40 T antigen; ATCC CRL-3216) cells were grown in Dulbecco's modified Eagle's medium (DMEM) supplemented with 10% fetal calf serum (FCS). HAP-1 wt and HAP-1 LDL-R deficient cells (HAP-1 LDL-RKO) purchased from Horizon Discovery) were grown in Iscove's Modified Dulbecco's Medium (IMDM) supplemented with 10% FCS. CHO (cell line derived from Chinese hamster ovaries) cells were grown in Ham's F12 medium supplemented with 2 mM glutamine and 10% FCS. All mammalian cell lines were maintained at 37° C. in a humidified incubator with 5% CO2. Drosophila S2 cells were grown in Schneider's medium supplemented with 10% FCS at 28° C.

Wild-type VSV (Mudd-Summer strain, Indiana serotype), VSVΔG-GCHAV (Rose et al., 2000) and VSV-eGFP were propagated in BSR cells.

VSVΔG-GFP is a recombinant VSV which was derived from a full-length cDNA clone of the VSV genome (Indiana serotype) in which the coding region of the G protein was replaced by a modified version of the GFP gene and pseudo-typed with the VSV G protein (Ferlin et al., 2014). VSVΔG-GFP was propagated on HEK-293T cells that had been previously transfected with pCAGGS-VSVG.

Plasmids and Cloning

Point mutations were created starting from the cloned VSV G gene (Indiana Mudd-Summer strain) in the pCAGGS plasmid. Briefly, forward and reverse primers containing the desired mutation were combined separately with one of the primers flanking the G gene to generate two PCR products. These two G gene fragments overlap in the region containing the mutation and were assembled into the pCAGGS linearized vector using Gibson assembly reaction kit (New England Biolabs).

Protein Expression, Purification and Labelling

VSV Gth was obtained by limited proteolysis of viral particles and purified as previously described (Albertini et al., 2012a).

DNA sequences encoding the 7 CR domains of the human LDL-R (NM_000527, GenBank) were synthetized (MWG biotech) and subcloned in the pGEX-6P1 bacterial expression vector (Invitrogen). Each protein construct contains at its N-terminus a GST tag and a preScission protease cleavage site. Each CR domain was purified using the following protocol derived from (Harper and Speicher, 2011). C41 bacteria transformed with the CR construct were cultured at 37° in LB-ampicillin medium until OD reached 0.6 AU. Protein expression was then induced with 1 mM IPTG during 5 h at 37° C. Cells were sonicated in lysis buffer (500 mM NaCl, 20 mM Tris-HCl pH 8, 2 mM CaCl2, 2% w/v sarkosyl and 1 mM DTT). The clarified supernatant was incubated with glutathione agarose beads (Thermo Fisher Scientific) in presence of 0.2% Triton X100 during 2 h. After incubation, beads were then extensively washed with equilibration buffer (200 mM NaCl, 50 mM Tris HCl pH 8, 2 mM CaCl2, 1 mM PMSF). The GST-CR construct was then eluted with the same buffer supplemented with 20 mM GSH. Purification of each GST-CR was achieved with a gel filtration step using a Superdex 200 column (Ge Healthcare). To isolate CR domains, purified GST-CR was incubated with preScission protease and injected on a gel filtration column Superdex 75 (Ge Healthcare). Fractions containing pure CR domains were then pooled, concentrated at 1 mM and stored at −80° C. until use.

One milligram of purified GST-CR2 (or GST-CR3) was labelled with the fluorescent dye ATTO550 NHS ester (Sigma Aldrich) using the instruction of the manufacturer. The labelled proteins were then diluted at a concentration of 50 μM and stored at −80° C. until use. The labelling ratio was estimated to be around 2 dyes per molecule.

Characterization of the Binding Between G and CR Domains

Purified GST-CR domains were incubated with magnetic beads coated with GSH (Eurogentec) under agitation during 20 min at 4° C. Then, the slurry was washed with the equilibration buffer at the appropriate pH (200 mM NaCl, 2 mM CaCl2, 50 mM Tris-HCl PH 8 or 50 mM MES-NaOH pH 6). Purified Gth or viral particles were preincubated in this same buffer for 20 min and added to the magnetic beads bound to GST-CR construction or GST alone. After 20 min of incubation under soft agitation, the slurry was washed two times with the equilibration buffer at the appropriate pH (either 8 or 6). Beads were re-suspended in the gel loading buffer and directly analyzed on a SDS PAGE.

Binding of CR Domains to Cells Expressing G (Either WT or Mutants)

For microscopy, BSR cells were infected for 4 h and were then incubated with GST-CR2ATTO550 or GST-CR3ATTO550 at 4° C. for 30 min. Cells were fixed with 4% paraformaldehyde and then permeabilized with 0.5% Triton X-100. Nucleoprotein was detected by using a mouse monoclonal anti-VSV N antibody. Goat anti-mouse Alexa fluor 488 (Invitrogen) was used as a secondary antibody. Images were captured using a Leica SP8 confocal microscope (63X oil-immersion objective).

For flow cytometry experiments, HEK-293T cells were transfected with pCAGGS plasmids encoding WT or mutant G using polyethylenimine (PEI, Sigma-Aldrich). 24 h after transfection, cells were collected and incubated with a mouse-monoclonal anti-G antibody that recognizes G ectodomain (8G5F11, KeraFast). Goat anti-mouse Alexa fluor 488 and GST-CR2ATTO550 (or GST-CR3ATTO550) were then simultaneously added to the cells. The fluorescence of cells was determined using a BD Accuri C6 flow cytometer.

Pseudotypes

HEK-293T cells at 80% confluence were transfected by pCAGGS encoding WT or mutant VSV G using PEI. At 24 h after transfection, cells were infected with VSVΔG-GFP at an MOI of 1. Two hours p.i., cells were washed to remove residual viruses from the inoculum. Cell supernatants containing the pseudotyped viral particles were collected at 16 h p.i. The infectious titers of the pseudotyped viruses were determined on non-transfected cells by counting cells expressing the GFP using a BD Accuri C6 flow cytometer at 4 h p.i. WT and mutant G incorporation in the pseudotyped particles was assessed after supernatant concentration by SDS PAGE and western blot analysis using an anti-VSV G and an anti-VSV M.

HAP-1 cells Infection

HAP-1 cells were plated at 70% confluence and incubated, or not, with 50 nM of RAP during 15 min. Cells were then infected with VSV-eGFP at an MOI of 1. RAP was maintained during all the infection time. The percentage of infected cells (GFP-positive) was determined 4 h p.i. using a BD Accuri C6 flow cytometer.

ITC

ITC experiments were performed at 293 K using a MicroCal iTC200 apparatus (GE Healthcare) in a buffer composed of 150 mM NaCl, 20 mM Tris-HCl pH 8.0 and 2 mM CaCl2. Gth, at a concentration of 50 µM, was titrated by successive injections of CR domains at a concentration of 600 µM. The titration sequence included a first 1 µl injection followed by 19 injections of 2 µl each with a spacing of 180 or 240 s between injections. OriginLab software (GE Healthcare) was used to analyze the raw data. Binding parameters were extracted from curve fitting analysis with a single-site binding model.

Cell-cell Fusion Assay

Cell-cell fusion assay was performed as previously described (Ferlin et al., 2014). Briefly, BSR cells plated on glass coverslips at 70% confluence were co-transfected with pCAGGS plasmids encoding WT G or mutant G, and P-GFP plasmid encoding the phosphoprotein of Rabies virus fused to GFP. Twenty four hours after transfection, cells were incubated with fusion buffer (DMEM-10 mM MES) at various pHs (from 5.0 to 7.5) for 10 minutes at 37°. Cells were then washed once and incubated with DMEM-10 mM HEPES-NaOH buffered at pH 7.4, 1% BSA at 37° C. for 1 hour. Cells were fixed with 4% paraformaldehyde in 1× PBS for 15 min. Cells nuclei were stained with DAPI and syncytia formation was analyzed with Zeiss Axiovert 200 fluorescence microscope with a 10× lens.

Bibliography

Albertini, A. A. V., Baquero, E., Ferlin, A., and Gaudin, Y. (2012b). Molecular and Cellular Aspects of Rhabdovirus Entry. Viruses 4, 117-139.

Amirache, F., Levy, C., Costa, C., Mangeot, P. E., Torbett, B. E., Wang, C. X., Negre, D., Cosset, F. L., and Verhoeyen, E. (2014). Mystery solved: VSV-G-LVs do not allow efficient gene transfer into unstimulated T cells, B cells, and HSCs because they lack the LDL receptor. Blood 123, 1422-1424.

Ammayappan, A., Peng, K. W., and Russell, S. J. (2013). Characteristics of oncolytic vesicular stomatitis virus displaying tumor-targeting ligands. J Virol 87, 13543-13555.

Barber, G. N. (2005). VSV-tumor selective replication and protein translation. Oncogene 24, 7710-7719.

Ferlin, A., Raux, H., Baquero, E., Lepault, J., and Gaudin, Y. (2014). Characterization of pH-sensitive molecular switches that trigger the structural transition of vesicular stomatitis virus glycoprotein from the postfusion state toward the prefusion state. J Virol 88, 13396-13409.

Finkelshtein, D., Werman, A., Novick, D., Barak, S., and Rubinstein, M. (2013). LDL receptor and its family members serve as the cellular receptors for vesicular stomatitis virus. Proceedings of the National Academy of Sciences of the United States of America 110, 7306-7311.

Roche, S., Bressanelli, S., Rey, F. A., and Gaudin, Y. (2006). Crystal structure of the low-pH form of the vesicular stomatitis virus glycoprotein G. Science 313, 187-191.

Roche, S., Rey, F. A., Gaudin, Y., and Bressanelli, S. (2007). Structure of the prefusion form of the vesicular stomatitis virus glycoprotein g. Science 315, 843-848.

Example 2

Preparation of Plasmid Encoding Modified G

Construction of pCAGGS plasmids containing the desired coding G sequence with the mCherry inserted at various position were generated using Gibson assembly reaction.

The empty vector pCAGGS was linearized using EcoRI restriction enzyme. Then 3 PCR products with overlapping parts were generated. The product I is the fragment of G before the insertion site; it is generated running a PCR on the VSV G gene using primers Ia and $Ib_1$ to insert the mCherry in position 1 or Ia and $Ib_{351}$ to insert the mCherry in position 351. The product II is the mCherry gene (using primers $IIa_1$ and $IIb_1$ to insert the mCherry in position 1 or $IIa_{351}$ and $IIb_{351}$ to insert the mCherry in position 351). The product III is the fragment of G after the insertion site; it is generated using primers $IIIa_1$ and IIIb to insert the mCherry in position 1 or $IIIa_{351}$ and IIIb to insert the mCherry in position 351.

Primer Sequences Were Synthetized by Eurofins Genomics

```
Ia:
                                     (SEQ ID NO : 332)
TCTCATCATTTTGGCAAAGATGAAGTGCCTTTTGTACTTAG

Ib1:
                                     (SEQ ID NO: 333)
TTGCTCACCATGCAATTCACCCCAATGAATAAAAAG

Ib351:
                                     (SEQ ID NO: 334)
GCTCACCATAGTTCCACTGATCATTCCGACC

IIa1:
                                     (SEQ ID NO: 335)
CATTGGGGTGAATTGCATGGTGAGCAAGGGC

IIa351:
                                     (SEQ ID NO: 336)
AATGATCAGTGGAACTATGGTGAGCAAGGGC

IIb1:
                                     (SEQ ID NO: 337)
AAAIIb1CTATGGTGAACTTCTTGTACAGCTCGTCC

IIb351:
                                     (SEQ ID NO: 338)
GTTCCCTTTCTGTGGTCTTGTACAGCTCGTCC

IIIa1:
                                     (SEQ ID NO: 339)
GAGCTGTACAAGAAGTTCACCATAGTTTTTCCACACA

IIIa351:
                                     (SEQ ID NO: 340)
CTGTACAAGACCACAGAAAGGGAACTGT

IIIb:
                                     (SEQ ID NO: 341)
CCGCCCGGGAGCTCGTTACTTTCCAAGTCGGTTC
```

After purification of each fragment on agarose gel, the 3 fragments plus the purified digested pCAGGS vector are then combined in equimolar concentration and assembled by Gibson assembly reaction. The DNA is then transformed into bacteria, and a correct plasmid product amplified after been identified by restriction digest and/or sequencing.

Example 3

Transient Expression of Modified VSV Glycoproteins

The transfection protocol will depend of the kind of cells to transduce. For HEK cells the inventors use PolyEthyenelmine (PEI) transfection protocol. For BHK the inventors use Ca-Phosphate transfection protocol or PEI.

Cells grown on coverslips were transfected with pCAGGS plasmid encoding for VSV modified glycoprotein. After 20 hour of transfection the cells were fixed with 4% paraformaldehyde in PBS. After washing (3 times with PBS) coverslides were mounted with immu-mount DAPI (thermofisher) and examined with a Zeiss microscope. Red fluorescence is present at the cell surface in both case indicating that the protein was correctly folded throw the Golgi apparatus (FIG. 19).

The invention is not limited to the above-mentioned embodiments.

The invention claimed is:

1. A polypeptide comprising an amino acid sequence at least 99% identical to the amino acid sequence set forth in SEQ ID NO: 1, wherein the polypeptide comprises an alanine or glutamine substitution at position 47 or an alanine or glutamine substitution at position 354.

2. The polypeptide of claim 1, wherein the polypeptide comprises an alanine substitution at position 47.

3. The polypeptide of claim 1, wherein the polypeptide comprises a glutamine substitution at position 47.

4. The polypeptide of claim 1, wherein the polypeptide comprises an alanine substitution at position 354.

5. The polypeptide of claim 1, wherein the polypeptide comprises a glutamine substitution at position 354.

6. A nucleic acid molecule encoding the polypeptide of claim 1.

7. A nucleic acid molecule encoding the polypeptide of claim 2.

8. A nucleic acid molecule encoding the polypeptide of claim 3.

9. A nucleic acid molecule encoding the polypeptide of claim 4.

10. A nucleic acid molecule encoding the polypeptide of claim 5.

11. A recombinant virus expressing the polypeptide of claim 1.

12. A recombinant virus expressing the polypeptide of claim 2.

13. A recombinant virus expressing the polypeptide of claim 3.

14. A recombinant virus expressing the polypeptide of claim 4.

15. A recombinant virus expressing the polypeptide of claim 5.

16. A composition comprising the polypeptide of claim 1.

17. A composition comprising the polypeptide of claim 2.

18. A composition comprising the polypeptide of claim 3.

19. A composition comprising the polypeptide of claim 4.

20. A composition comprising the polypeptide of claim 5.

21. A membrane comprising the polypeptide of claim 1, wherein the polypeptide is anchored in the membrane, and wherein the membrane is the membrane of a liposome, vesicle, exosome, or nanoparticle.

22. A membrane comprising the polypeptide of claim 2, wherein the polypeptide is anchored in the membrane, and wherein the membrane is the membrane of a liposome, vesicle, exosome, or nanoparticle.

23. A membrane comprising the polypeptide of claim 3, wherein the polypeptide is anchored in the membrane, and wherein the membrane is the membrane of a liposome, vesicle, exosome, or nanoparticle.

24. A membrane comprising the polypeptide of claim 4, wherein the polypeptide is anchored in the membrane, and wherein the membrane is the membrane of a liposome, vesicle, exosome, or nanoparticle.

25. A membrane comprising the polypeptide of claim 5, wherein the polypeptide is anchored in the membrane, and wherein the membrane is the membrane of a liposome, vesicle, exosome, or nanoparticle.

* * * * *

SEQUENCE LISTING

```
Sequence total quantity: 341
SEQ ID NO: 1           moltype = AA  length = 495
FEATURE                Location/Qualifiers
source                 1..495
                       mol_type = protein
                       organism = Vesicular stomatitis virus
SEQUENCE: 1
KFTIVFPHNQ KGNWKNVPSN YHYCPSSSDL NWHNDLIGTA IQVKMPKSHK AIQADGWMCH  60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 2           moltype = AA  length = 511
FEATURE                Location/Qualifiers
source                 1..511
                       mol_type = protein
                       organism = Vesicular stomatitis virus
SEQUENCE: 2
MKCLLYLAFL FIGVNCKFTI VFPHNQKGNW KNVPSNYHYC PSSSDLNWHN DLIGTAIQVK  60
MPKSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
```

```
QETWSKIRAG LPISPVDLSY LAPKNPGTGP AFTIINGTLK YFETRYIRVD IAAPILSRMV    360
GMISGTTTER ELWDDWAPYE DVEIGPNGVL RTSSGYKFPL YMIGHGMLDS DLHLSSKAQV    420
FEHPHIQDAA SQLPDDESLF FGDTGLSKNP IELVEGWFSS WKSSIASFFF IIGLIIGLFL    480
VLRVGIHLCI KLKHTKKRQI YTDIEMNRLG K                                  511

SEQ ID NO: 3              moltype = AA  length = 496
FEATURE                   Location/Qualifiers
source                    1..496
                          mol_type = protein
                          organism = Vesicular stomatitis virus
SEQUENCE: 3
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT    120
DAEVVVVQAT PHHVLVDEYT GEWIDSQLVG GKCSKEVCQT VHNSTVWHAD YKITGLCESN    180
LASVDITFFS EDGQKTSLGK PNTGFRSNHF AYESGEKACR MQYCTQWGIR LPSGVWFELV    240
DKDLFQAAKL PECPRGSSIS APSQTSVDVS LIQDVERILD YSLCQETWSK IRAKLPVSPV    300
DLSYLAPKNP GSGPAFTIIN GTLKYFETRY IRVDISNPII PHMVGTMSGT TTERELWNDW    360
YPYEDVEIGP NGVLKTPTGF KFPLYMIGHG MLDSDLHKSS QAQVFEHPHA KDAASQLPDD    420
ETLFFGDTGL SKNPVELVEG WFSSWKSTLA SFFLIIGLGV ALIFIIRIIV AIRYKYKGRK    480
TQKIYNDVEM SRLGNK                                                   496

SEQ ID NO: 4              moltype = AA  length = 512
FEATURE                   Location/Qualifiers
source                    1..512
                          mol_type = protein
                          organism = Vesicular stomatitis virus
SEQUENCE: 4
MLRLFLFCFL ALGAHSKFTI VFPHHQKGNW KNVPSTYHYC PSSSDQNWHN DLTGVSLHVK    60
IPKSHKAIQA DGWMCHAAKW VTTCDFRWYG PKYITHSIHS MSPTLEQCKT SIEQTKQGVW    120
INPGFPPQSC GYATVTDAEV VVVQATPHHV LVDEYTDSQL VGGKCS KEVCQTVWHNS    180
TVWHADYKIT GLCESNLASV DITFFSEDGQ KTSLGKPNTG FRSNHFAYES GEKACRMQYC    240
TQWGIRLPSG VWFELVDKDL FQAAKLPECP RGSSISAPSQ TSVDVSLIQD VERILDYSLC    300
QETWSKIRAK LPVSPVDLSY LAPKNPGSGP AFTIINGTLK YFETRYIRVD ISNPIIPHMV    360
GTMSGTTTER ELWNDWYPYE DVEIGPNGVL KTPTGFKFPL YMIGHGMLDS DLHKSSQAQV    420
FEHPHAKDAA SQLPDDETLF FGDTGLSKNP VELVEGWFSS WKSTLASFFL IIGLGVALIF    480
IIRIIVAIRY KYGRKTQKI YNDVEMSRLG NK                                  512

SEQ ID NO: 5              moltype = AA  length = 501
FEATURE                   Location/Qualifiers
source                    1..501
                          mol_type = protein
                          organism = Vesicular stomatitis virus
SEQUENCE: 5
KIEIVFPQHT TGDWKRVPHE YNYCPTSADK NSHGTQTGIP VELTMPKGLT THQVDGFMCH    60
SALWMTTCDF RWYGPKYITH SIHNEEPTDY QCLEAIKAYK DGVSFNPGFP PQSCGYGTVT    120
DAEAHIVTVT PHSVKVDEYT GEWIDPHFIG GRCKGQICET VHNSTKWFTS SDGESVCSQL    180
FTLVGGTFFS DSEEITSMGL PETGIRSNYF PYVSTEGIC MPFCRKPGVK LKNDLWFQIT    240
DPDLDKTVRD LPHIKDCDLS SSIVTPGEHA TDISLISDVE RILDYALCQN TWSKIEAGEP    300
ITPVDLSYLG PKNPGAGPVF TIINGSLHYF MSKYLRVELE SPVIPRMEGK VAGTRIVRQL    360
WDQWFPFGEV EIGPNGVLKT KQGYKFPLHI IGTGEVDNDI KMERIVKHWE HPHIEAAQTF    420
LKKDDTEEVL YYGDTGVSKN PVELVEGWFS GWRSSIMGVL AVIIGFVILI FLIRLIGVLS    480
SLFRQKRRPI YKSDVEMAHF R                                             501

SEQ ID NO: 6              moltype = AA  length = 517
FEATURE                   Location/Qualifiers
source                    1..517
                          mol_type = protein
                          organism = Vesicular stomatitis virus
SEQUENCE: 6
MLSYLIFALV VSPILGKIEI VFPQHTTGDW KRVPHEYNYC PTSADKNSHG TQTGIPVELT    60
MPKGLTTHQV DGFMCHSALW MTTCDFRWYG PKYITHSIHN EEPTDYQCLE AIKAYKDGVS    120
FNPGFPPQSC GYGTVTDAEA HIVTVTPHSV KVDEYTGEWI DPHFIGGRCK GQICETVHNS    180
TKWFTSSDGE SVCSQLFTLV GGTFFSDSEE ITSMGLPETG IRSNYFPYVS TEGICKMPFC    240
RKPGYKLKND LWFQITDPDL DKTVRDLPHI KDCDLSSSIV TPGEHATDIS LISDVERILD    300
YALCQNTWSK IEAGEPITPV DLSYLGPKNP GAGPVFTIIN GSLHYFMSKY LRVELESPVI    360
PRMEGKVAGT RIVRQLWDQW FPFGEVEIGP NGVLKTKQGY KFPLHIIGTG EVDNDIKMER    420
IVKHWEHPHI EAAQTFLKKD DTEEVLYYGD TGVSKNPVEL VEGWFSGWRS SIMGVLAVII    480
GFVILIFLIR LIGVLSSLFR QKRRPIYKSD VEMAHFR                            517

SEQ ID NO: 7              moltype = AA  length = 502
FEATURE                   Location/Qualifiers
source                    1..502
                          mol_type = protein
                          organism = Vesicular stomatitis virus
SEQUENCE: 7
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
```

-continued

```
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSRVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 8              moltype = AA  length = 523
FEATURE                   Location/Qualifiers
source                    1..523
                          mol_type = protein
                          organism = Vesicular stomatitis virus
SEQUENCE: 8
MKMKMVIAGL ILCIGILPAI GKITISFPQS LKGDWRPVPK GYNYCPTSAD KNLHGDLIDI     60
GLRLRAPKSF KGISADGWMC HAARWITTCD FRWYGPKYIT HSIHSFRPSN DQCKEAIRLT    120
NEGNWINPGF PPQSCGYASV TDSESVVVTV TKHQVLVDEY SGSWIDSQFP GGSCTSPICD    180
TVHNSTLWHA DHTLDSICDQ EFVAMDAVLF TESGKFEEFG KPNSGIRSNY FPYESLKDVC    240
QMDFCKRKGF KLPSGVWFEI EDAEKSHKAQ VELKIKRCPH GAVISAPNQN AADINLIMDV    300
ERILDYSLCQ ATWSKIQNKE ALTPIDISYL GPKNPGPGPA FTIINGTLHY FNTRYIRVDI    360
AGPVTKEITG FVSGTSTSRV LWDQWFPYGE NSIGPNGLLK TASGYKYPLF MVGTGVLDAD    420
IHKLGEATVI EHPHAKEAQK VVDDSEVIFF GDTGVSKNPV EVVEGWFSGW RSSLMSIFGI    480
ILLIVCLVLI VRILIALKYC CVRHKKRTIY KEDLEMGRIP RRA                      523

SEQ ID NO: 9              moltype = AA  length = 494
FEATURE                   Location/Qualifiers
source                    1..494
                          mol_type = protein
                          organism = Vesicular stomatitis virus
SEQUENCE: 9
KFTIVFPQSQ KGDWKDVPPN YRYCPSSADQ NWHGDLLGVN IRAKMPKVHK AIKADGWMCH     60
AAKWVTTCDY RWYGPQYITH SIHSFIPTKA QCEESIKQTK EGVWINPGFP PKNCGYASVS    120
DAESIIVQAT AHSVMIDEYS GDWLDSQFPT GRCTGSTCET IHNSTLWYAD YQVTGLCDSA    180
LVSTEVTFYS EDGLMTSIGR QNTGYRSNYF PYEKGAAACR MKYCTHEGIR LPSGVWFEMV    240
DKELLESVQM PECPAGLTIS APTQTSVDVS LILDVERMLD YSLCQETWSK VHSGLPISPV    300
DLGYIAPKNP GAGPAFTIVN GTLKYFDTRY LRIDIEGPVL KMTGKVSGT PTKRELWTEW     360
FPYDDVEIGP NGVLKTPEGY KFPLYMIGHG LLDSDLQKTS QAEVFHHPQI AEAVQKLPDD    420
ETLFFGDTGI SKNPVEVIEG WFSNWRSSVM AIVFAILLLV ITVLMVRLCV AFRHFCCQKR    480
HKIYNDLEMN QLRR                                                      494

SEQ ID NO: 10             moltype = AA  length = 511
FEATURE                   Location/Qualifiers
source                    1..511
                          mol_type = protein
                          organism = Vesicular stomatitis virus
SEQUENCE: 10
MTPAFILCML LAGSSWAKFT IVFPQSQKGD WKDVPPNYRY CPSSADQNWH GDLLGVNIRA     60
KMPKVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNYFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK RELWTEWFPY DDVEIGPNGV LKTPEGYKFP LYMIGHGLLD SDLQKTSQAE    420
VFHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                   511

SEQ ID NO: 11             moltype = AA  length = 495
FEATURE                   Location/Qualifiers
source                    1..495
                          mol_type = protein
                          organism = Vesicular stomatitis virus
SEQUENCE: 11
KFSIVFPQSQ KGNWKNVPSS YHYCPSSSDQ NWHNDLLGIT MKVKMPKTHK AIQADGWMCH     60
AAKWITTCDF RWYGPKYITH SIHSIQPTSE QCKESIKQTK QGTWMSPGFP PQNCGYATVT    120
DSVAVVVQAT PHHVLVDEYT GEWIDSQFPN GKCETEECET VHNSTVWYSD YKVTGLCDAT    180
LVDTEITFFS EDGKKESIGK PNTGYRSNYF AYEKGDKVCK MNYCKHAGVR LPSGVWFEFV    240
DQDVYAAAKL PECPVGATIS APTQTSVDVS LILDVERILD YSLCQETWSK IRSKQPVSPV    300
DLSYLAPKNP GTGPAFTIIN GTLKYFETRY IRIDIDNPII SKMVGKISGS QTERELWTEW    360
FPYEGVEIGP NGILKTPTGY KFPLFMIGHG MLDSDLHKTS QAEVFEHPHL AEAPKQLPEE    420
ETLFFGDTGI SKNPVELIEG WFSSWKSTVV TFPPAIGVPI LLYVVARIVI AVRYRYQGSN    480
NKRIYNDIEM SRFRK                                                     495

SEQ ID NO: 12             moltype = AA  length = 512
FEATURE                   Location/Qualifiers
source                    1..512
                          mol_type = protein
                          organism = Vesicular stomatitis virus
SEQUENCE: 12
MNFLLLTFIV LPLCSHAKFS IVFPQSQKGN WKNVPSSYHY CPSSSDQNWH NDLLGITMKV     60
KMPKTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
```

```
STVWYSDYKV TGLCDATLVD TEITFFSEDG KKESIGKPNT GYRSNYFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE RELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                 512

SEQ ID NO: 13           moltype = AA  length = 496
FEATURE                 Location/Qualifiers
source                  1..496
                        mol_type = protein
                        organism = Vesicular stomatitis virus
SEQUENCE: 13
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTERELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 14           moltype = AA  length = 513
FEATURE                 Location/Qualifiers
source                  1..513
                        mol_type = protein
                        organism = Vesicular stomatitis virus
SEQUENCE: 14
MLVLYLLLSL LALGAQCKFT IVFPHNQKGN WKNVPANYQY CPSSSDLNWH NGLIGTSLQV    60
KMPKSHKAIQ ADGWMCHAAK WVTTCDFRWY GPKYVTHSIK SMIPTVDQCK ESIAQTKQGT    120
WLNPGFPPQS CGYASVTDAE AVIVKATPHQ VLVDEYTGEW VDSQFPTGKC NKDICPTVHN    180
STTWHSDYKV TGLCDANLIS MDITFFSEDG KLTSLGKEGT GFRSNYFAYE NGDKACRMQY    240
CKHWGVRLPS GVWFEMADKD IYNDAKFPDC PEGSSIAAPS QTSVDVSLIQ DVERILDYSL    300
CQETWSKIRA HLPISPVDLS YLSPKNPGTG PAFTIINGTL KYFETRYIRV DIAGPIIPQM    360
RGVISGTTTE RELWTDWYPY EDVEIGPNGV LKTATGYKFP LYMIGHGMLD SDLHISSKAQ    420
VFEHPHIQDA ASQLPDDETL FFGDTGLSKN PIELVEGWFS GWKSTIASFF FIIGLVIGLY    480
LVLRIGIALC IKCRVQEKRP KIYTDVEMNR LDR                                513

SEQ ID NO: 15           moltype = AA  length = 495
FEATURE                 Location/Qualifiers
SITE                    47
                        note = misc_feature - Xaa can be any naturally occurring
                         amino acid except Lys or Arg
source                  1..495
                        mol_type = protein
                        organism = Vesicular stomatitis virus
SEQUENCE: 15
KFTIVFPHNQ KGNWKNVPSN YHYCPSSSDL NWHNDLIGTA IQVKMPXSHK AIQADGWMCH    60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTERELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVRVGI HLCIKLKHTK    480
KRQIYTDIEM NRLGK                                                    495

SEQ ID NO: 16           moltype = AA  length = 495
FEATURE                 Location/Qualifiers
SITE                    354
                        note = misc_feature - Xaa can be any naturally occurring
                         amino acid except Lys or Arg
source                  1..495
                        mol_type = protein
                        organism = Vesicular stomatitis virus
SEQUENCE: 16
KFTIVFPHNQ KGNWKNVPSN YHYCPSSSDL NWHNDLIGTA IQVKMPKSHK AIQADGWMCH    60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEXELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 17           moltype = AA  length = 495
FEATURE                 Location/Qualifiers
```

```
SITE                        47
                            note = misc_feature - Xaa can be any naturally occurring
                             amino acid except Lys or Arg
SITE                        354
                            note = misc_feature - Xaa can be any naturally occurring
                             amino acid except Lys or Arg
source                      1..495
                            mol_type = protein
                            organism = Vesicular stomatitis virus
SEQUENCE: 17
KFTIVFPHNQ KGNWKNVPSN YHYCPSSSDL NWHNDLIGTA IQVKMPXSHK AIQADGWMCH   60
ASKWVTTCDF RWYGPKYITQ SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTEXELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 18               moltype = AA  length = 511
FEATURE                     Location/Qualifiers
SITE                        63
                            note = misc_feature - Xaa can be any naturally occurring
                             amino acid except Lys or Arg
source                      1..511
                            mol_type = protein
                            organism = Vesicular stomatitis virus
SEQUENCE: 18
MKCLLYLAFL FIGVNCKFTI VFPHNQKGNW KNVPSNYHYC PSSSDLNWHN DLIGTAIQVK   60
MPXSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 19               moltype = AA  length = 511
FEATURE                     Location/Qualifiers
SITE                        370
                            note = misc_feature - Xaa can be any naturally occurring
                             amino acid except Lys or Arg
source                      1..511
                            mol_type = protein
                            organism = Vesicular stomatitis virus
SEQUENCE: 19
MKCLLYLAFL FIGVNCKFTI VFPHNQKGNW KNVPSNYHYC PSSSDLNWHN DLIGTAIQVK   60
MPKSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTEX ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 20               moltype = AA  length = 511
FEATURE                     Location/Qualifiers
SITE                        63
                            note = misc_feature - Xaa can be any naturally occurring
                             amino acid except Lys or Arg
SITE                        370
                            note = misc_feature - Xaa can be any naturally occurring
                             amino acid except Lys or Arg
source                      1..511
                            mol_type = protein
                            organism = Vesicular stomatitis virus
SEQUENCE: 20
MKCLLYLAFL FIGVNCKFTI VFPHNQKGNW KNVPSNYHYC PSSSDLNWHN DLIGTAIQVK   60
MPXSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTEX ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511
```

```
SEQ ID NO: 21           moltype = AA   length = 496
FEATURE                 Location/Qualifiers
SITE                    47
                        note = misc_feature - Xaa can be any naturally occurring
                         amino acid except Lys or Arg
source                  1..496
                        mol_type = protein
                        organism = Vesicular stomatitis virus
SEQUENCE: 21
KFTIVFPHHQ KGNWKNVPST YHYCPSSSDQ NWHNDLTGVS LHVKIPXSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 22           moltype = AA   length = 496
FEATURE                 Location/Qualifiers
SITE                    354
                        note = misc_feature - Xaa can be any naturally occurring
                         amino acid except Lys or Arg
source                  1..496
                        mol_type = protein
                        organism = Vesicular stomatitis virus
SEQUENCE: 22
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEXELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 23           moltype = AA   length = 496
FEATURE                 Location/Qualifiers
SITE                    47
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..496
                        mol_type = protein
                        organism = Vesicular stomatitis virus
SEQUENCE: 23
KFTIVFPHHQ KGNWKNVPST YHYCPSSSDQ NWHNDLTGVS LHVKIPXSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEXELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 24           moltype = AA   length = 512
FEATURE                 Location/Qualifiers
SITE                    63
                        note = misc_feature - Xaa can be any naturally occurring
                         amino acid except Lys or Arg
source                  1..512
                        mol_type = protein
                        organism = Vesicular stomatitis virus
SEQUENCE: 24
MLRLFLFCFL ALGAHSKFTI VFPHHQKGNW KNVPSTYHYC PSSSDQNWHN DLTGVSLHVK    60
IPXSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNHFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTER ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512
```

```
SEQ ID NO: 25              moltype = AA  length = 512
FEATURE                    Location/Qualifiers
SITE                       370
                           note = misc_feature - Xaa can be any naturally occurring
                             amino acid except Lys or Arg
source                     1..512
                           mol_type = protein
                           organism = Vesicular stomatitis virus
SEQUENCE: 25
MLRLFLFCFL ALGAHSKFTI VFPHHQKGNW KNVPSTYHYC PSSSDQNWHN DLTGVSLHVK    60
IPKSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNHFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTEX ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 26              moltype = AA  length = 512
FEATURE                    Location/Qualifiers
SITE                       63
                           note = misc_feature - Xaa can be any naturally occurring
                             amino acid except Lys or Arg
SITE                       370
                           note = misc_feature - Xaa can be any naturally occurring
                             amino acid except Lys or Arg
source                     1..512
                           mol_type = protein
                           organism = Vesicular stomatitis virus
SEQUENCE: 26
MLRLFLFCFL ALGAHSKFTI VFPHHQKGNW KNVPSTYHYC PSSSDQNWHN DLTGVSLHVK    60
IPXSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNHFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTEX ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 27              moltype = AA  length = 501
FEATURE                    Location/Qualifiers
SITE                       47
                           note = misc_feature - Xaa can be any naturally occurring
                             amino acid except Lys or Arg
source                     1..501
                           mol_type = protein
                           organism = Vesicular stomatitis virus
SEQUENCE: 27
KIEIVFPQHT TGDWKRVPHE YNYCPTSADK NSHGTQTGIP VELTMPXGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNYF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVRQL   360
WDQWFPPGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                             501

SEQ ID NO: 28              moltype = AA  length = 501
FEATURE                    Location/Qualifiers
SITE                       358
                           note = misc_feature - Xaa can be any naturally occurring
                             amino acid except Lys or Arg
source                     1..501
                           mol_type = protein
                           organism = Vesicular stomatitis virus
SEQUENCE: 28
KIEIVFPQHT TGDWKRVPHE YNYCPTSADK NSHGTQTGIP VELTMPKGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNYF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVXQL   360
WDQWFPPGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                             501
```

```
SEQ ID NO: 29          moltype = AA  length = 501
FEATURE                Location/Qualifiers
SITE                   47
                       note = misc_feature - Xaa can be any naturally occurring
                        amino acid except Lys or Arg
SITE                   358
                       note = misc_feature - Xaa can be any naturally occurring
                        amino acid except Lys or Arg
source                 1..501
                       mol_type = protein
                       organism = Vesicular stomatitis virus
SEQUENCE: 29
KIEIVFPQHT TGDWKRVPHE YNYCPTSADK NSHGTQTGIP VELTMPXGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNYF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVXQL   360
WDQWFPPGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                             501

SEQ ID NO: 30          moltype = AA  length = 517
FEATURE                Location/Qualifiers
SITE                   63
                       note = misc_feature - Xaa can be any naturally occurring
                        amino acid except Lys or Arg
source                 1..517
                       mol_type = protein
                       organism = Vesicular stomatitis virus
SEQUENCE: 30
MLSYLIFALV VSPILGKIEI VFPQHTTGDW KRVPHEYNYC PTSADKNSHG TQTGIPVELT    60
MPXGLTTHQV DGFMCHSALW MTTCDFRWYG PKYITHSIHN EEPTDYQCLE AIKAYKDGVS   120
FNPGFPPQSC GYGTVTDAEA HIVTVTPHSV KVDEYTGEWI DPHFIGGRCK GQICETVHNS   180
TKWFTSSDGE SVCSQLFTLV GGTFFSDSEE ITSMGLPETG IRSNYFPYVS TEGICKMPFC   240
RKPGYKLKND LWFQITDPDL DKTVRDLPHI KDCDLSSSIV TPGEHATDIS LISDVERILD   300
YALCQNTWSK IEAGEPITPV DLSYLGPKNP GAGPVFTIIN GSLHYFMSKY LRVELESPVI   360
PRMEGKVAGT RIVRQLWDQW FPFGEVEIGP NGVLKTKQGY KFPLHIIGTG EVDNDIKMER   420
IVKHWEHPHI EAAQTFLKKD DTEEVLYYGD TGVSKNPVEL VEGWFSGWRS SIMGVLAVII   480
GFVILIFLIR LIGVLSSLFR QKRRPIYKSD VEMAHFR                            517

SEQ ID NO: 31          moltype = AA  length = 517
FEATURE                Location/Qualifiers
SITE                   374
                       note = misc_feature - Xaa can be any naturally occurring
                        amino acid except Lys or Arg
source                 1..517
                       mol_type = protein
                       organism = Vesicular stomatitis virus
SEQUENCE: 31
MLSYLIFALV VSPILGKIEI VFPQHTTGDW KRVPHEYNYC PTSADKNSHG TQTGIPVELT    60
MPKGLTTHQV DGFMCHSALW MTTCDFRWYG PKYITHSIHN EEPTDYQCLE AIKAYKDGVS   120
FNPGFPPQSC GYGTVTDAEA HIVTVTPHSV KVDEYTGEWI DPHFIGGRCK GQICETVHNS   180
TKWFTSSDGE SVCSQLFTLV GGTFFSDSEE ITSMGLPETG IRSNYFPYVS TEGICKMPFC   240
RKPGYKLKND LWFQITDPDL DKTVRDLPHI KDCDLSSSIV TPGEHATDIS LISDVERILD   300
YALCQNTWSK IEAGEPITPV DLSYLGPKNP GAGPVFTIIN GSLHYFMSKY LRVELESPVI   360
PRMEGKVAGT RIVXQLWDQW FPFGEVEIGP NGVLKTKQGY KFPLHIIGTG EVDNDIKMER   420
IVKHWEHPHI EAAQTFLKKD DTEEVLYYGD TGVSKNPVEL VEGWFSGWRS SIMGVLAVII   480
GFVILIFLIR LIGVLSSLFR QKRRPIYKSD VEMAHFR                            517

SEQ ID NO: 32          moltype = AA  length = 517
FEATURE                Location/Qualifiers
SITE                   63
                       note = misc_feature - Xaa can be any naturally occurring
                        amino acid except Lys or Arg
SITE                   374
                       note = misc_feature - Xaa can be any naturally occurring
                        amino acid except Lys or Arg
source                 1..517
                       mol_type = protein
                       organism = Vesicular stomatitis virus
SEQUENCE: 32
MLSYLIFALV VSPILGKIEI VFPQHTTGDW KRVPHEYNYC PTSADKNSHG TQTGIPVELT    60
MPXGLTTHQV DGFMCHSALW MTTCDFRWYG PKYITHSIHN EEPTDYQCLE AIKAYKDGVS   120
FNPGFPPQSC GYGTVTDAEA HIVTVTPHSV KVDEYTGEWI DPHFIGGRCK GQICETVHNS   180
TKWFTSSDGE SVCSQLFTLV GGTFFSDSEE ITSMGLPETG IRSNYFPYVS TEGICKMPFC   240
RKPGYKLKND LWFQITDPDL DKTVRDLPHI KDCDLSSSIV TPGEHATDIS LISDVERILD   300
YALCQNTWSK IEAGEPITPV DLSYLGPKNP GAGPVFTIIN GSLHYFMSKY LRVELESPVI   360
```

```
PRMEGKVAGT RIVXQLWDQW FPFGEVEIGP NGVLKTKQGY KFPPLHIIGTG EVDNDIKMER    420
IVKHWEHPHI EAAQTFLKKD DTEEVLYYGD TGVSKNPVEL VEGWFSGWRS SIMGVLAVII    480
GFVILIFLIR LIGVLSSLFR QKRRPIYKSD VEMAHFR                             517

SEQ ID NO: 33              moltype = AA  length = 502
FEATURE                    Location/Qualifiers
SITE                       47
                           note = misc_feature - Xaa can be any naturally occurring
                             amino acid except Lys or Arg
source                     1..502
                           mol_type = protein
                           organism = Vesicular stomatitis virus
SEQUENCE: 33
KITISFPQSL KGDWRPVPKG YNYCPTSADK NLHGDLIDIG LRLRAPXSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSRVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 34              moltype = AA  length = 502
FEATURE                    Location/Qualifiers
SITE                       358
                           note = misc_feature - Xaa can be any naturally occurring
                             amino acid except Lys or Arg
source                     1..502
                           mol_type = protein
                           organism = Vesicular stomatitis virus
SEQUENCE: 34
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSXVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 35              moltype = AA  length = 502
FEATURE                    Location/Qualifiers
SITE                       47
                           note = misc_feature - Xaa can be any naturally occurring
                             amino acid except Lys or Arg
SITE                       358
                           note = misc_feature - Xaa can be any naturally occurring
                             amino acid except Lys or Arg
source                     1..502
                           mol_type = protein
                           organism = Vesicular stomatitis virus
SEQUENCE: 35
KITISFPQSL KGDWRPVPKG YNYCPTSADK NLHGDLIDIG LRLRAPXSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSXVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 36              moltype = AA  length = 523
FEATURE                    Location/Qualifiers
SITE                       68
                           note = misc_feature - Xaa can be any naturally occurring
                             amino acid except Lys or Arg
source                     1..523
                           mol_type = protein
                           organism = Vesicular stomatitis virus
SEQUENCE: 36
MKMKMVIAGL ILCIGILPAI GKITISFPQS LKGDWRPVPK GYNYCPTSAD KNLHGDLIDI    60
GLRLRAPXSF KGISADGWMC HAARWITTCD FRWYGPKYIT HSIHSFRPSN DQCKEAIRLT    120
NEGNWINPGF PPQSCGYASV TDSESVVVTV TKHQVLVDEY SGSWIDSQFP GGSCTSPICD    180
TVHNSTLWHA DHTLDSICDQ EFVAMDAVLF TESGKFEEFG KPNSGIRSNY FPYESLKDVC    240
QMDFCKRKGF KLPSGVWFEI EDAEKSHKAQ VELKIKRCPH GAVISAPNQN AADINLIMDV    300
ERILDYSLCQ ATWSKIQNKE ALTPIDISYL GPKNPGPGPA FTIINGTLHY FNTRYIRVDI    360
```

```
AGPVTKEITG FVSGTSTSRV LWDQWFPYGE NSIGPNGLLK TASGYKYPLF MVGTGVLDAD    420
IHKLGEATVI EHPHAKEAQK VVDDSEVIFF GDTGVSKNPV EVVEGWFSGW RSSLMSIFGI    480
ILLIVCLVLI VRILIALKYC CVRHKKRTIY KEDLEMGRIP RRA                     523

SEQ ID NO: 37           moltype = AA   length = 523
FEATURE                 Location/Qualifiers
SITE                    379
                        note = misc_feature - Xaa can be any naturally occurring
                          amino acid except Lys or Arg
source                  1..523
                        mol_type = protein
                        organism = Vesicular stomatitis virus
SEQUENCE: 37
MKMKMVIAGL ILCIGILPAI GKITISFPQS LKGDWRPVPK GYNYCPTSAD KNLHGDLIDI    60
GLRLRAPKSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNY FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                    523

SEQ ID NO: 38           moltype = AA   length = 523
FEATURE                 Location/Qualifiers
SITE                    68
                        note = misc_feature - Xaa can be any naturally occurring
                          amino acid except Lys or Arg
SITE                    379
                        note = misc_feature - Xaa can be any naturally occurring
                          amino acid except Lys or Arg
source                  1..523
                        mol_type = protein
                        organism = Vesicular stomatitis virus
SEQUENCE: 38
MKMKMVIAGL ILCIGILPAI GKITISFPQS LKGDWRPVPK GYNYCPTSAD KNLHGDLIDI    60
GLRLRAPXSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNY FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                    523

SEQ ID NO: 39           moltype = AA   length = 494
FEATURE                 Location/Qualifiers
SITE                    47
                        note = misc_feature - Xaa can be any naturally occurring
                          amino acid except Lys or Arg
source                  1..494
                        mol_type = protein
                        organism = Vesicular stomatitis virus
SEQUENCE: 39
KFTIVFPQSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 40           moltype = AA   length = 494
FEATURE                 Location/Qualifiers
SITE                    354
                        note = misc_feature - Xaa can be any naturally occurring
                          amino acid except Lys or Arg
source                  1..494
                        mol_type = protein
                        organism = Vesicular stomatitis virus
SEQUENCE: 40
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKXELWTEW   360
```

```
FPYDDVEIGP NGVLKTPEGY KFPLYMIGHG LLDSDLQKTS QAEVFHHPQI AEAVQKLPDD    420
ETLFFGDTGI SKNPVEVIEG WFSNWRSSVM AIVFAILLLV ITVLMVRLCV AFRHFCCQKR    480
HKIYNDLEMN QLRR                                                      494

SEQ ID NO: 41           moltype = AA  length = 494
FEATURE                 Location/Qualifiers
SITE                    47
                        note = misc_feature - Xaa can be any naturally occurring
                          amino acid except Lys or Arg
SITE                    354
                        note = misc_feature - Xaa can be any naturally occurring
                          amino acid except Lys or Arg
source                  1..494
                        mol_type = protein
                        organism = Vesicular stomatitis virus
SEQUENCE: 41
KFTIVFPQSQ KGDWKDVPPN YRYCPSSADQ NWHGDLLGVN IRAKMPXVHK AIKADGWMCH     60
AAKWVTTCDY RWYGPQYITH SIHSFIPTKA QCEESIKQTK EGVWINPGFP PKNCGYASVS    120
DAESIIVQAT AHSVMIDEYS GDWLDSQFPT GRCTGSTCET IHNSTLWYAD YQVTGLCDSA    180
LVSTEVTFYS EDGLMTSIGR QNTGYRSNYF PYEKGAAACR MKYCTHEGIR LPSGVWFEMV    240
DKELLESVQM PECPAGLTIS APTQTSVDVS LILDVERMLD YSLCQETWSK VHSGLPISPV    300
DLGYIAPKNP GAGPAFTIVN GTLKYFDTRY LRIDIEGPVL KKMTGKVSGT PTKXELWTEW    360
FPYDDVEIGP NGVLKTPEGY KFPLYMIGHG LLDSDLQKTS QAEVFHHPQI AEAVQKLPDD    420
ETLFFGDTGI SKNPVEVIEG WFSNWRSSVM AIVFAILLLV ITVLMVRLCV AFRHFCCQKR    480
HKIYNDLEMN QLRR                                                      494

SEQ ID NO: 42           moltype = AA  length = 511
FEATURE                 Location/Qualifiers
SITE                    64
                        note = misc_feature - Xaa can be any naturally occurring
                          amino acid except Lys or Arg
source                  1..511
                        mol_type = protein
                        organism = Vesicular stomatitis virus
SEQUENCE: 42
MTPAFILCML LAGSSWAKFT IVFPQSQKGD WKDVPPNYRY CPSSADQNWH GDLLGVNIRA     60
KMPXVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNYFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK RELWTEWFPY DDVEIGPNGV LKTPEGYKFP LYMIGHGLLD SDLQKTSQAE    420
VFHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                    511

SEQ ID NO: 43           moltype = AA  length = 511
FEATURE                 Location/Qualifiers
SITE                    371
                        note = misc_feature - Xaa can be any naturally occurring
                          amino acid except Lys or Arg
source                  1..511
                        mol_type = protein
                        organism = Vesicular stomatitis virus
SEQUENCE: 43
MTPAFILCML LAGSSWAKFT IVFPQSQKGD WKDVPPNYRY CPSSADQNWH GDLLGVNIRA     60
KMPKVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNYFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK XELWTEWFPY DDVEIGPNGV LKTPEGYKFP LYMIGHGLLD SDLQKTSQAE    420
VFHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                    511

SEQ ID NO: 44           moltype = AA  length = 511
FEATURE                 Location/Qualifiers
SITE                    64
                        note = misc_feature - Xaa can be any naturally occurring
                          amino acid except Lys or Arg
SITE                    371
                        note = misc_feature - Xaa can be any naturally occurring
                          amino acid except Lys or Arg
source                  1..511
                        mol_type = protein
                        organism = Vesicular stomatitis virus
SEQUENCE: 44
MTPAFILCML LAGSSWAKFT IVFPQSQKGD WKDVPPNYRY CPSSADQNWH GDLLGVNIRA     60
KMPXVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
```

```
STLWYADYQV TGLCDSALVS TEVTFYSEDG LMTSIGRQNT GYRSNYFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK XELWTEWFPY DDVEIGPNGV LKTPEGYKFP LYMIGHGLLD SDLQKTSQAE    420
VPHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                  511

SEQ ID NO: 45           moltype = AA  length = 495
FEATURE                 Location/Qualifiers
SITE                    47
                        note = misc_feature - Xaa can be any naturally occurring
                          amino acid except Lys or Arg
source                  1..495
                        mol_type = protein
                        organism = Vesicular stomatitis virus
SEQUENCE: 45
KFSIVFPQSQ KGNWKNVPSS YHYCPSSSDQ NWHNDLLGIT MKVKMPXTHK AIQADGWMCH     60
AAKWITTCDF RWYGPKYITH SIHSIQPTSE QCKESIKQTK QGTWMSPGFP PQNCGYATVT    120
DSVAVVVQAT PHHVLVDEYT GEWIDSQFPN GKCETEECET VHNSTVWYSD YKVTGLCDAT    180
LVDTEITFFS EDGKKESIGK PNTGYRSNYF AYEKGDKVCK MNYCKHAGVR LPSGVWFEFV    240
DQDVYAAAKL PECPVGATIS APTQTSVDVS LILDVERILD YSLCQETWSK IRSKQPVSPV    300
DLSYLAPKNP GTGPAFTIIN GTLKYFETRY IRIDIDNPII SKMVGKISGS QTERELWTEW    360
FPYEGVEIGP NGILKTPTGY KFPLFMIGHG MLDSDLHKTS QAEVFEHPHL AEAPKQLPEE    420
ETLFFGDTGI SKNPVELIEG WFSSWKSTVV TFFFAIGVFI LLYVVARIVI AVRYRYQGSN    480
NKRIYNDIEM SRFRK                                                   495

SEQ ID NO: 46           moltype = AA  length = 495
FEATURE                 Location/Qualifiers
SITE                    354
                        note = misc_feature - Xaa can be any naturally occurring
                          amino acid except Lys or Arg
source                  1..495
                        mol_type = protein
                        organism = Vesicular stomatitis virus
SEQUENCE: 46
KFSIVFPQSQ KGNWKNVPSS YHYCPSSSDQ NWHNDLLGIT MKVKMPKTHK AIQADGWMCH     60
AAKWITTCDF RWYGPKYITH SIHSIQPTSE QCKESIKQTK QGTWMSPGFP PQNCGYATVT    120
DSVAVVVQAT PHHVLVDEYT GEWIDSQFPN GKCETEECET VHNSTVWYSD YKVTGLCDAT    180
LVDTEITFFS EDGKKESIGK PNTGYRSNYF AYEKGDKVCK MNYCKHAGVR LPSGVWFEFV    240
DQDVYAAAKL PECPVGATIS APTQTSVDVS LILDVERILD YSLCQETWSK IRSKQPVSPV    300
DLSYLAPKNP GTGPAFTIIN GTLKYFETRY IRIDIDNPII SKMVGKISGS QTEXELWTEW    360
FPYEGVEIGP NGILKTPTGY KFPLFMIGHG MLDSDLHKTS QAEVFEHPHL AEAPKQLPEE    420
ETLFFGDTGI SKNPVELIEG WFSSWKSTVV TFFFAIGVFI LLYVVARIVI AVRYRYQGSN    480
NKRIYNDIEM SRFRK                                                   495

SEQ ID NO: 47           moltype = AA  length = 495
FEATURE                 Location/Qualifiers
SITE                    47
                        note = misc_feature - Xaa can be any naturally occurring
                          amino acid except Lys or Arg
SITE                    354
                        note = misc_feature - Xaa can be any naturally occurring
                          amino acid except Lys or Arg
source                  1..495
                        mol_type = protein
                        organism = Vesicular stomatitis virus
SEQUENCE: 47
KFSIVFPQSQ KGNWKNVPSS YHYCPSSSDQ NWHNDLLGIT MKVKMPXTHK AIQADGWMCH     60
AAKWITTCDF RWYGPKYITH SIHSIQPTSE QCKESIKQTK QGTWMSPGFP PQNCGYATVT    120
DSVAVVVQAT PHHVLVDEYT GEWIDSQFPN GKCETEECET VHNSTVWYSD YKVTGLCDAT    180
LVDTEITFFS EDGKKESIGK PNTGYRSNYF AYEKGDKVCK MNYCKHAGVR LPSGVWFEFV    240
DQDVYAAAKL PECPVGATIS APTQTSVDVS LILDVERILD YSLCQETWSK IRSKQPVSPV    300
DLSYLAPKNP GTGPAFTIIN GTLKYFETRY IRIDIDNPII SKMVGKISGS QTEXELWTEW    360
FPYEGVEIGP NGILKTPTGY KFPLFMIGHG MLDSDLHKTS QAEVFEHPHL AEAPKQLPEE    420
ETLFFGDTGI SKNPVELIEG WFSSWKSTVV TFFFAIGVFI LLYVVARIVI AVRYRYQGSN    480
NKRIYNDIEM SRFRK                                                   495

SEQ ID NO: 48           moltype = AA  length = 512
FEATURE                 Location/Qualifiers
SITE                    64
                        note = misc_feature - Xaa can be any naturally occurring
                          amino acid except Lys or Arg
source                  1..512
                        mol_type = protein
                        organism = Vesicular stomatitis virus
SEQUENCE: 48
MNFLLLTFIV LPLCSHAKFS IVFPQSQKGN WKNVPSSYHY CPSSSDQNWH NDLLGITMKV     60
KMPXTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
```

```
STVWYSDYKV TGLCDATLVD TEITFFSEDG KKESIGKPNT GYRSNYFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE RELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                  512

SEQ ID NO: 49           moltype = AA  length = 512
FEATURE                 Location/Qualifiers
SITE                    371
                        note = misc_feature - Xaa can be any naturally occurring
                          amino acid except Lys or Arg
source                  1..512
                        mol_type = protein
                        organism = Vesicular stomatitis virus
SEQUENCE: 49
MNFLLLTFIV LPLCSHAKFS IVFPQSQKGN WKNVPSSYHY CPSSSDQNWH NDLLGITMKV     60
KMPKTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
STVWYSDYKV TGLCDATLVD TEITFFSEDG KKESIGKPNT GYRSNYFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE XELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                  512

SEQ ID NO: 50           moltype = AA  length = 512
FEATURE                 Location/Qualifiers
SITE                    64
                        note = misc_feature - Xaa can be any naturally occurring
                          amino acid except Lys or Arg
SITE                    371
                        note = misc_feature - Xaa can be any naturally occurring
                          amino acid except Lys or Arg
source                  1..512
                        mol_type = protein
                        organism = Vesicular stomatitis virus
SEQUENCE: 50
MNFLLLTFIV LPLCSHAKFS IVFPQSQKGN WKNVPSSYHY CPSSSDQNWH NDLLGITMKV     60
KMPXTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
STVWYSDYKV TGLCDATLVD TEITFFSEDG KKESIGKPNT GYRSNYFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE XELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                  512

SEQ ID NO: 51           moltype = AA  length = 496
FEATURE                 Location/Qualifiers
SITE                    47
                        note = misc_feature - Xaa can be any naturally occurring
                          amino acid except Lys or Arg
source                  1..496
                        mol_type = protein
                        organism = Vesicular stomatitis virus
SEQUENCE: 51
KFTIVFPHNQ KGNWKNVPAN YQYCPSSSDL NWHNGLIGTS LQVKMPXSHK AIQADGWMCH     60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTERELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                    496

SEQ ID NO: 52           moltype = AA  length = 496
FEATURE                 Location/Qualifiers
SITE                    354
                        note = misc_feature - Xaa can be any naturally occurring
                          amino acid except Lys or Arg
source                  1..496
                        mol_type = protein
                        organism = Vesicular stomatitis virus
SEQUENCE: 52
KFTIVFPHNQ KGNWKNVPAN YQYCPSSSDL NWHNGLIGTS LQVKMPKSHK AIQADGWMCH     60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
```

```
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEXELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 53              moltype = AA  length = 496
FEATURE                    Location/Qualifiers
SITE                       47
                           note = misc_feature - Xaa can be any naturally occurring
                             amino acid except Lys or Arg
SITE                       354
                           note = misc_feature - Xaa can be any naturally occurring
                             amino acid except Lys or Arg
source                     1..496
                           mol_type = protein
                           organism = Vesicular stomatitis virus
SEQUENCE: 53
KFTIVFPHNQ KGNWKNVPAN YQYCPSSSDL NWHNGLIGTS LQVKMPXSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEXELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 54              moltype = AA  length = 513
FEATURE                    Location/Qualifiers
SITE                       64
                           note = misc_feature - Xaa can be any naturally occurring
                             amino acid except Lys or Arg
source                     1..513
                           mol_type = protein
                           organism = Vesicular stomatitis virus
SEQUENCE: 54
MLVLYLLLSL LALGAQCKFT IVFPHNQKGN WKNVPANYQY CPSSSDLNWH NGLIGTSLQV    60
KMPXSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNYFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE RELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 55              moltype = AA  length = 513
FEATURE                    Location/Qualifiers
SITE                       371
                           note = misc_feature - Xaa can be any naturally occurring
                             amino acid except Lys or Arg
source                     1..513
                           mol_type = protein
                           organism = Vesicular stomatitis virus
SEQUENCE: 55
MLVLYLLLSL LALGAQCKFT IVFPHNQKGN WKNVPANYQY CPSSSDLNWH NGLIGTSLQV    60
KMPKSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNYFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE XELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 56              moltype = AA  length = 513
FEATURE                    Location/Qualifiers
SITE                       64
                           note = misc_feature - Xaa can be any naturally occurring
                             amino acid except Lys or Arg
SITE                       371
                           note = misc_feature - Xaa can be any naturally occurring
                             amino acid except Lys or Arg
source                     1..513
                           mol_type = protein
                           organism = Vesicular stomatitis virus
SEQUENCE: 56
```

```
MLVLYLLLSL LALGAQCKFT IVFPHNQKGN WKNVPANYQY CPSSSDLNWH NGLIGTSLQV    60
KMPXSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNYFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE XELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 57           moltype = AA  length = 495
FEATURE                 Location/Qualifiers
SITE                    8
                        note = misc_feature - Xaa can be any naturally occurring
                         amino acid except Lys or Arg
SITE                    47
                        note = misc_feature - Xaa can be any naturally occurring
                         amino acid except Lys or Arg
source                  1..495
                        mol_type = protein
                        organism = Vesicular stomatitis virus
SEQUENCE: 57
KFTIVFPXNQ KGNWKNVPSN YHYCPSSSDL NWHNDLIGTA IQVKMPXSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 58           moltype = AA  length = 495
FEATURE                 Location/Qualifiers
SITE                    8
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..495
                        mol_type = protein
                        organism = Vesicular stomatitis virus
SEQUENCE: 58
KFTIVFPXNQ KGNWKNVPSN YHYCPSSSDL NWHNDLIGTA IQVKMPKSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEXLWDDW    360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 59           moltype = AA  length = 495
FEATURE                 Location/Qualifiers
SITE                    8
                        note = misc_feature - Xaa can be any naturally occurring
                         amino acid except Lys or Arg
SITE                    47
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..495
                        mol_type = protein
                        organism = Vesicular stomatitis virus
SEQUENCE: 59
KFTIVFPXNQ KGNWKNVPSN YHYCPSSSDL NWHNDLIGTA IQVKMPXSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEXLWDDW    360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495
```

```
SEQ ID NO: 60              moltype = AA  length = 495
FEATURE                    Location/Qualifiers
SITE                       47
                           note = misc_feature - Xaa can be any naturally occurring
                             amino acid except Lys or Arg
SITE                       209
                           note = misc_feature - Xaa can be any naturally occurring
                             amino acid except Lys or Arg
source                     1..495
                           mol_type = protein
                           organism = Vesicular stomatitis virus
SEQUENCE: 60
KFTIVFPHNQ KGNWKNVPSN YHYCPSSSDL NWHNDLIGTA IQVKMPXSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNXF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 61              moltype = AA  length = 495
FEATURE                    Location/Qualifiers
SITE                       209
                           note = misc_feature - Xaa can be any naturally occurring
                             amino acid except Lys or Arg
SITE                       354
                           note = misc_feature - Xaa can be any naturally occurring
                             amino acid except Lys or Arg
source                     1..495
                           mol_type = protein
                           organism = Vesicular stomatitis virus
SEQUENCE: 61
KFTIVFPHNQ KGNWKNVPSN YHYCPSSSDL NWHNDLIGTA IQVKMPKSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNXF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEXLWDDW    360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 62              moltype = AA  length = 495
FEATURE                    Location/Qualifiers
SITE                       47
                           note = misc_feature - Xaa can be any naturally occurring
                             amino acid except Lys or Arg
SITE                       209
                           note = misc_feature - Xaa can be any naturally occurring
                             amino acid except Lys or Arg
SITE                       354
                           note = misc_feature - Xaa can be any naturally occurring
                             amino acid except Lys or Arg
source                     1..495
                           mol_type = protein
                           organism = Vesicular stomatitis virus
SEQUENCE: 62
KFTIVFPHNQ KGNWKNVPSN YHYCPSSSDL NWHNDLIGTA IQVKMPXSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNXF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEXLWDDW    360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 63              moltype = AA  length = 495
FEATURE                    Location/Qualifiers
SITE                       8
                           note = misc_feature - Xaa can be any naturally occurring
                             amino acid except Lys or Arg
SITE                       47
                           note = misc_feature - Xaa can be any naturally occurring
                             amino acid except Lys or Arg
SITE                       209
                           note = misc_feature - Xaa can be any naturally occurring
```

```
                           amino acid except Lys or Arg
source                     1..495
                           mol_type = protein
                           organism = Vesicular stomatitis virus
SEQUENCE: 63
KFTIVFPXNQ KGNWKNVPSN YHYCPSSSDL NWHNDLIGTA IQVKMPXSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNXF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 64              moltype = AA   length = 511
FEATURE                    Location/Qualifiers
SITE                       24
                           note = misc_feature - Xaa can be any naturally occurring
                           amino acid except Lys or Arg
SITE                       63
                           note = misc_feature - Xaa can be any naturally occurring
                           amino acid except Lys or Arg
source                     1..511
                           mol_type = protein
                           organism = Vesicular stomatitis virus
SEQUENCE: 64
MKCLLYLAFL FIGVNCKFTI VFPXNQKGNW KNVPSNYHYC PSSSDLNWHN DLIGTAIQVK    60
MPXSHKAIQA DGWMCHASKW VTTCDFRWYG PKYITQSIRS FTPSVEQCKE SIEQTKQGTW   120
LNPGFPPQSC GYATVTDAEA VIVQVTPHHV LVDEYTGEWV DSQFINGKCS NYICPTVHNS   180
TTWHSDYKVK GLCDSNLISM DITFFSEDGE LSSLGKEGTG FRSNYFAYET GGKACKMQYC   240
KHWGVRLPSG VWFEMADKDL FAAARFPECP EGSSISAPSQ TSVDVSLIQD VERILDYSLC   300
QETWSKIRAG LPISPVDLSY LAPKNPGTGP AFTIINGTLK YFETRYIRVD IAAPILSRMV   360
GMISGTTTER ELWDDWAPYE DVEIGPNGVL RTSSGYKFPL YMIGHGMLDS DLHLSSKAQV   420
FEHPHIQDAA SQLPDDESLF FGDTGLSKNP IELVEGWFSS WKSSIASFFF IIGLIIGLFL   480
VLRVGIHLCI KLKHTKKRQI YTDIEMNRLG K                                 511

SEQ ID NO: 65              moltype = AA   length = 511
FEATURE                    Location/Qualifiers
SITE                       24
                           note = misc_feature - Xaa can be any naturally occurring
                           amino acid except Lys or Arg
SITE                       370
                           note = misc_feature - Xaa can be any naturally occurring
                           amino acid except Lys or Arg
source                     1..511
                           mol_type = protein
                           organism = Vesicular stomatitis virus
SEQUENCE: 65
MKCLLYLAFL FIGVNCKFTI VFPXNQKGNW KNVPSNYHYC PSSSDLNWHN DLIGTAIQVK    60
MPKSHKAIQA DGWMCHASKW VTTCDFRWYG PKYITQSIRS FTPSVEQCKE SIEQTKQGTW   120
LNPGFPPQSC GYATVTDAEA VIVQVTPHHV LVDEYTGEWV DSQFINGKCS NYICPTVHNS   180
TTWHSDYKVK GLCDSNLISM DITFFSEDGE LSSLGKEGTG FRSNYFAYET GGKACKMQYC   240
KHWGVRLPSG VWFEMADKDL FAAARFPECP EGSSISAPSQ TSVDVSLIQD VERILDYSLC   300
QETWSKIRAG LPISPVDLSY LAPKNPGTGP AFTIINGTLK YFETRYIRVD IAAPILSRMV   360
GMISGTTTEX ELWDDWAPYE DVEIGPNGVL RTSSGYKFPL YMIGHGMLDS DLHLSSKAQV   420
FEHPHIQDAA SQLPDDESLF FGDTGLSKNP IELVEGWFSS WKSSIASFFF IIGLIIGLFL   480
VLRVGIHLCI KLKHTKKRQI YTDIEMNRLG K                                 511

SEQ ID NO: 66              moltype = AA   length = 511
FEATURE                    Location/Qualifiers
SITE                       24
                           note = misc_feature - Xaa can be any naturally occurring
                           amino acid except Lys or Arg
SITE                       63
                           note = misc_feature - Xaa can be any naturally occurring
                           amino acid except Lys or Arg
SITE                       370
                           note = misc_feature - Xaa can be any naturally occurring
                           amino acid except Lys or Arg
source                     1..511
                           mol_type = protein
                           organism = Vesicular stomatitis virus
SEQUENCE: 66
MKCLLYLAFL FIGVNCKFTI VFPXNQKGNW KNVPSNYHYC PSSSDLNWHN DLIGTAIQVK    60
MPXSHKAIQA DGWMCHASKW VTTCDFRWYG PKYITQSIRS FTPSVEQCKE SIEQTKQGTW   120
LNPGFPPQSC GYATVTDAEA VIVQVTPHHV LVDEYTGEWV DSQFINGKCS NYICPTVHNS   180
TTWHSDYKVK GLCDSNLISM DITFFSEDGE LSSLGKEGTG FRSNYFAYET GGKACKMQYC   240
KHWGVRLPSG VWFEMADKDL FAAARFPECP EGSSISAPSQ TSVDVSLIQD VERILDYSLC   300
```

```
QETWSKIRAG LPISPVDLSY LAPKNPGTGP AFTIINGTLK YFETRYIRVD IAAPILSRMV    360
GMISGTTTEX ELWDDWAPYE DVEIGPNGVL RTSSGYKFPL YMIGHGMLDS DLHLSSKAQV    420
FEHPHIQDAA SQLPDDESLF FGDTGLSKNP IELVEGWFSS WKSSIASFFF IIGLIIGLFL    480
VLRVGIHLCI KLKHTKKRQI YTDIEMNRLG K                                  511

SEQ ID NO: 67           moltype = AA   length = 511
FEATURE                 Location/Qualifiers
SITE                    63
                        note = misc_feature - Xaa can be any naturally occurring
                          amino acid except Lys or Arg
SITE                    225
                        note = misc_feature - Xaa can be any naturally occurring
                          amino acid except Lys or Arg
source                  1..511
                        mol_type = protein
                        organism = Vesicular stomatitis virus
SEQUENCE: 67
MKCLLYLAFL FIGVNCKFTI VFPHNQKGNW KNVPSNYHYC PSSSDLNWHN DLIGTAIQVK     60
MPXSHKAIQA DGWMCHASKW VTTCDFRWYG PKYITQSIRS FTPSVEQCKE SIEQTKQGTW    120
LNPGFPPQSC GYATVTDAEA VIVQVTPHHV LVDEYTGEWV DSQFINGKCS NYICPTVHNS    180
TTWHSDYKVK GLCDSNLISM DITFFSEDGE LSSLGKEGTG FRSNXFAYET GGKACKMQYC    240
KHWGVRLPSG VWFEMADKDL FAAARFPECP EGSSISAPSQ TSVDVSLIQD VERILDYSLC    300
QETWSKIRAG LPISPVDLSY LAPKNPGTGP AFTIINGTLK YFETRYIRVD IAAPILSRMV    360
GMISGTTTER ELWDDWAPYE DVEIGPNGVL RTSSGYKFPL YMIGHGMLDS DLHLSSKAQV    420
FEHPHIQDAA SQLPDDESLF FGDTGLSKNP IELVEGWFSS WKSSIASFFF IIGLIIGLFL    480
VLRVGIHLCI KLKHTKKRQI YTDIEMNRLG K                                  511

SEQ ID NO: 68           moltype = AA   length = 511
FEATURE                 Location/Qualifiers
SITE                    225
                        note = misc_feature - Xaa can be any naturally occurring
                          amino acid except Lys or Arg
SITE                    370
                        note = misc_feature - Xaa can be any naturally occurring
                          amino acid except Lys or Arg
source                  1..511
                        mol_type = protein
                        organism = Vesicular stomatitis virus
SEQUENCE: 68
MKCLLYLAFL FIGVNCKFTI VFPHNQKGNW KNVPSNYHYC PSSSDLNWHN DLIGTAIQVK     60
MPKSHKAIQA DGWMCHASKW VTTCDFRWYG PKYITQSIRS FTPSVEQCKE SIEQTKQGTW    120
LNPGFPPQSC GYATVTDAEA VIVQVTPHHV LVDEYTGEWV DSQFINGKCS NYICPTVHNS    180
TTWHSDYKVK GLCDSNLISM DITFFSEDGE LSSLGKEGTG FRSNXFAYET GGKACKMQYC    240
KHWGVRLPSG VWFEMADKDL FAAARFPECP EGSSISAPSQ TSVDVSLIQD VERILDYSLC    300
QETWSKIRAG LPISPVDLSY LAPKNPGTGP AFTIINGTLK YFETRYIRVD IAAPILSRMV    360
GMISGTTTEX ELWDDWAPYE DVEIGPNGVL RTSSGYKFPL YMIGHGMLDS DLHLSSKAQV    420
FEHPHIQDAA SQLPDDESLF FGDTGLSKNP IELVEGWFSS WKSSIASFFF IIGLIIGLFL    480
VLRVGIHLCI KLKHTKKRQI YTDIEMNRLG K                                  511

SEQ ID NO: 69           moltype = AA   length = 511
FEATURE                 Location/Qualifiers
SITE                    63
                        note = misc_feature - Xaa can be any naturally occurring
                          amino acid except Lys or Arg
SITE                    225
                        note = misc_feature - Xaa can be any naturally occurring
                          amino acid except Lys or Arg
SITE                    370
                        note = misc_feature - Xaa can be any naturally occurring
                          amino acid except Lys or Arg
source                  1..511
                        mol_type = protein
                        organism = Vesicular stomatitis virus
SEQUENCE: 69
MKCLLYLAFL FIGVNCKFTI VFPHNQKGNW KNVPSNYHYC PSSSDLNWHN DLIGTAIQVK     60
MPXSHKAIQA DGWMCHASKW VTTCDFRWYG PKYITQSIRS FTPSVEQCKE SIEQTKQGTW    120
LNPGFPPQSC GYATVTDAEA VIVQVTPHHV LVDEYTGEWV DSQFINGKCS NYICPTVHNS    180
TTWHSDYKVK GLCDSNLISM DITFFSEDGE LSSLGKEGTG FRSNXFAYET GGKACKMQYC    240
KHWGVRLPSG VWFEMADKDL FAAARFPECP EGSSISAPSQ TSVDVSLIQD VERILDYSLC    300
QETWSKIRAG LPISPVDLSY LAPKNPGTGP AFTIINGTLK YFETRYIRVD IAAPILSRMV    360
GMISGTTTEX ELWDDWAPYE DVEIGPNGVL RTSSGYKFPL YMIGHGMLDS DLHLSSKAQV    420
FEHPHIQDAA SQLPDDESLF FGDTGLSKNP IELVEGWFSS WKSSIASFFF IIGLIIGLFL    480
VLRVGIHLCI KLKHTKKRQI YTDIEMNRLG K                                  511

SEQ ID NO: 70           moltype = AA   length = 511
FEATURE                 Location/Qualifiers
SITE                    24
                        note = misc_feature - Xaa can be any naturally occurring
                          amino acid except Lys or Arg
```

```
SITE                    63
                        note = misc_feature - Xaa can be any naturally occurring
                           amino acid except Lys or Arg
SITE                    225
                        note = misc_feature - Xaa can be any naturally occurring
                           amino acid except Lys or Arg
SITE                    370
                        note = misc_feature - Xaa can be any naturally occurring
                           amino acid except Lys or Arg
source                  1..511
                        mol_type = protein
                        organism = Vesicular stomatitis virus
SEQUENCE: 70
MKCLLYLAFL FIGVNCKFTI VFPXNQKGNW KNVPSNYHYC PSSSDLNWHN DLIGTAIQVK   60
MPXSHKAIQA DGWMCHASKW VTTCDFRWYG PKYITQSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNXFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTEX ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 71           moltype = AA  length = 496
FEATURE                 Location/Qualifiers
SITE                    8
                        note = misc_feature - Xaa can be any naturally occurring
                           amino acid except Lys or Arg
SITE                    47
                        note = misc_feature - Xaa can be any naturally occurring
                           amino acid except Lys or Arg
source                  1..496
                        mol_type = protein
                        organism = Vesicular stomatitis virus
SEQUENCE: 71
KFTIVFPXHQ KGNWKNVPST YHYCPSSSDQ NWHNDLTGVS LHVKIPXSHK AIQADGWMCH   60
AAKWVTTCDF RWYGPKYITH SIHSMSPTLE QCKTSIEQTK QGVWINPGFP PQSCGYATVT  120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV  240
DKDLFQAAKL PECPRGSSIS APSQTSVDVS LIQDVERILD YSLCQETWSK IRAKLPVSPV  300
DLSYLAPKNP GSGPAFTIIN GTLKYFETRY IRVDISNPII PHMVGTMSGT TTERELWNDW  360
YPYEDVEIGP NGVLKTPTGF KFPLYMIGHG MLDSDLHKSS QAQVFEHPHA KDAASQLPDD  420
ETLFFGDTGL SKNPVELVEG WFSSWKSTLA SFFLIIGLGV ALIFIIRIIV AIRYKYKGRK  480
TQKIYNDVEM SRLGNK                                                  496

SEQ ID NO: 72           moltype = AA  length = 496
FEATURE                 Location/Qualifiers
SITE                    8
                        note = misc_feature - Xaa can be any naturally occurring
                           amino acid except Lys or Arg
SITE                    354
                        note = misc_feature - Xaa can be any naturally occurring
                           amino acid except Lys or Arg
source                  1..496
                        mol_type = protein
                        organism = Vesicular stomatitis virus
SEQUENCE: 72
KFTIVFPXHQ KGNWKNVPST YHYCPSSSDQ NWHNDLTGVS LHVKIPKSHK AIQADGWMCH   60
AAKWVTTCDF RWYGPKYITH SIHSMSPTLE QCKTSIEQTK QGVWINPGFP PQSCGYATVT  120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV  240
DKDLFQAAKL PECPRGSSIS APSQTSVDVS LIQDVERILD YSLCQETWSK IRAKLPVSPV  300
DLSYLAPKNP GSGPAFTIIN GTLKYFETRY IRVDISNPII PHMVGTMSGT TEXELWNDW   360
YPYEDVEIGP NGVLKTPTGF KFPLYMIGHG MLDSDLHKSS QAQVFEHPHA KDAASQLPDD  420
ETLFFGDTGL SKNPVELVEG WFSSWKSTLA SFFLIIGLGV ALIFIIRIIV AIRYKYKGRK  480
TQKIYNDVEM SRLGNK                                                  496

SEQ ID NO: 73           moltype = AA  length = 496
FEATURE                 Location/Qualifiers
SITE                    8
                        note = misc_feature - Xaa can be any naturally occurring
                           amino acid except Lys or Arg
SITE                    47
                        note = misc_feature - Xaa can be any naturally occurring
                           amino acid except Lys or Arg
SITE                    354
                        note = misc_feature - Xaa can be any naturally occurring
                           amino acid except Lys or Arg
source                  1..496
```

```
                            mol_type = protein
                            organism = Vesicular stomatitis virus
SEQUENCE: 73
KFTIVFPXHQ KGNWKNVPST YHYCPSSSDQ NWHNDLTGVS LHVKIPXSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEXELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 74           moltype = AA   length = 496
FEATURE                 Location/Qualifiers
SITE                    47
                        note = misc_feature - Xaa can be any naturally occurring
                         amino acid except Lys or Arg
SITE                    209
                        note = misc_feature - Xaa can be any naturally occurring
                         amino acid except Lys or Arg
source                  1..496
                        mol_type = protein
                        organism = Vesicular stomatitis virus
SEQUENCE: 74
KFTIVFPHHQ KGNWKNVPST YHYCPSSSDQ NWHNDLTGVS LHVKIPXSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNXF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 75           moltype = AA   length = 496
FEATURE                 Location/Qualifiers
SITE                    209
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..496
                        mol_type = protein
                        organism = Vesicular stomatitis virus
SEQUENCE: 75
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNXF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEXELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 76           moltype = AA   length = 496
FEATURE                 Location/Qualifiers
SITE                    47
                        note = misc_feature - Xaa can be any naturally occurring
                         amino acid except Lys or Arg
SITE                    209
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..496
                        mol_type = protein
                        organism = Vesicular stomatitis virus
SEQUENCE: 76
KFTIVFPHHQ KGNWKNVPST YHYCPSSSDQ NWHNDLTGVS LHVKIPXSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNXF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEXELWNDW   360
YPYEDVEIGP NGVLKTPTGF KFPLYMIGHG MLDSDLHKSS QAQVFEHPHA KDAASQLPDD   420
```

```
ETLFFGDTGL SKNPVELVEG WFSSWKSTLA SFFLIIGLGV ALIFIIRIIV AIRYKYKGRK    480
TQKIYNDVEM SRLGNK                                                   496

SEQ ID NO: 77           moltype = AA  length = 496
FEATURE                 Location/Qualifiers
SITE                    8
                        note = misc_feature - Xaa can be any naturally occurring
                          amino acid except Lys or Arg
SITE                    47
                        note = misc_feature - Xaa can be any naturally occurring
                          amino acid except Lys or Arg
SITE                    209
                        note = misc_feature - Xaa can be any naturally occurring
                          amino acid except Lys or Arg
SITE                    354
                        note = misc_feature - Xaa can be any naturally occurring
                          amino acid except Lys or Arg
source                  1..496
                        mol_type = protein
                        organism = Vesicular stomatitis virus
SEQUENCE: 77
KFTIVFPXHQ KGNWKNVPST YHYCPSSSDQ NWHNDLTGVS LHVKIPXSHK AIQADGWMCH     60
AAKWVTTCDF RWYGPKYITH SIHSMSPTLE QCKTSIEQTK QGVWINPGFP PQSCGYATVT    120
DAEVVVVQAT PHHVLVDEYT GEWIDSQLVG GKCSKEVCQT VHNSTVWHAD YKITGLCESN    180
LASVDITFFS EDGQKTSLGK PNTGFRSNXF AYESGEKACR MQYCTQWGIR LPSGVWFELV    240
DKDLFQAAKL PECPRGSSIS APSQTSVDVS LIQDVERILD YSLCQETWSK IRAKLPVSPV    300
DLSYLAPKNP GSGPAFTIIN GTLKYFETRY IRVDISNPII PHMVGTMSGT TTEXELWNDW    360
YPYEDVEIGP NGVLKTPTGF KFPLYMIGHG MLDSDLHKSS QAQVFEHPHA KDAASQLPDD    420
ETLFFGDTGL SKNPVELVEG WFSSWKSTLA SFFLIIGLGV ALIFIIRIIV AIRYKYKGRK    480
TQKIYNDVEM SRLGNK                                                   496

SEQ ID NO: 78           moltype = AA  length = 512
FEATURE                 Location/Qualifiers
SITE                    24
                        note = misc_feature - Xaa can be any naturally occurring
                          amino acid except Lys or Arg
SITE                    63
                        note = misc_feature - Xaa can be any naturally occurring
                          amino acid except Lys or Arg
source                  1..512
                        mol_type = protein
                        organism = Vesicular stomatitis virus
SEQUENCE: 78
MLRLFLFCFL ALGAHSKFTI VFPXHQKGNW KNVPSTYHYC PSSSDQNWHN DLTGVSLHVK     60
IPXSHKAIQA DGWMCHAAKW VTTCDFRWYG PKYITHSIHS MSPTLEQCKT SIEQTKQGVW    120
INPGFPPQSC GYATVTDAEV VVVQATPHHV LVDEYTGEWI DSQLVGGKCS KEVCQTVHNS    180
TVWHADYKIT GLCESNLASV DITFFSEDGQ KTSLGKPNTG FRSNHFAYES GEKACRMQYC    240
TQWGIRLPSG VWFELVDKDL FQAAKLPECP RGSSISAPSQ TSVDVSLIQD VERILDYSLC    300
QETWSKIRAK LPVSPVDLSY LAPKNPGSGP AFTIINGTLK YFETRYIRVD ISNPIIPHMV    360
GTMSGTTTER ELWNDWYPYE DVEIGPNGVL KTPTGFKFPL YMIGHGMLDS DLHKSSQAQV    420
FEHPHAKDAA SQLPDDETLF FGDTGLSKNP VELVEGWFSS WKSTLASFFL IIGLGVALIF    480
IIRIIVAIRY KYKGRKTQKI YNDVEMSRLG NK                                  512

SEQ ID NO: 79           moltype = AA  length = 512
FEATURE                 Location/Qualifiers
SITE                    24
                        note = misc_feature - Xaa can be any naturally occurring
                          amino acid except Lys or Arg
SITE                    370
                        note = misc_feature - Xaa can be any naturally occurring
                          amino acid except Lys or Arg
source                  1..512
                        mol_type = protein
                        organism = Vesicular stomatitis virus
SEQUENCE: 79
MLRLFLFCFL ALGAHSKFTI VFPXHQKGNW KNVPSTYHYC PSSSDQNWHN DLTGVSLHVK     60
IPKSHKAIQA DGWMCHAAKW VTTCDFRWYG PKYITHSIHS MSPTLEQCKT SIEQTKQGVW    120
INPGFPPQSC GYATVTDAEV VVVQATPHHV LVDEYTGEWI DSQLVGGKCS KEVCQTVHNS    180
TVWHADYKIT GLCESNLASV DITFFSEDGQ KTSLGKPNTG FRSNHFAYES GEKACRMQYC    240
TQWGIRLPSG VWFELVDKDL FQAAKLPECP RGSSISAPSQ TSVDVSLIQD VERILDYSLC    300
QETWSKIRAK LPVSPVDLSY LAPKNPGSGP AFTIINGTLK YFETRYIRVD ISNPIIPHMV    360
GTMSGTTTEX ELWNDWYPYE DVEIGPNGVL KTPTGFKFPL YMIGHGMLDS DLHKSSQAQV    420
FEHPHAKDAA SQLPDDETLF FGDTGLSKNP VELVEGWFSS WKSTLASFFL IIGLGVALIF    480
IIRIIVAIRY KYKGRKTQKI YNDVEMSRLG NK                                  512

SEQ ID NO: 80           moltype = AA  length = 512
FEATURE                 Location/Qualifiers
SITE                    24
                        note = misc_feature - Xaa can be any naturally occurring
```

```
                    amino acid except Lys or Arg
SITE                63
                    note = misc_feature - Xaa can be any naturally occurring
                    amino acid except Lys or Arg
SITE                370
                    note = misc_feature - Xaa can be any naturally occurring
                    amino acid except Lys or Arg
source              1..512
                    mol_type = protein
                    organism = Vesicular stomatitis virus
SEQUENCE: 80
MLRLFLFCFL ALGAHSKFTI VFPXHQKGNW KNVPSTYHYC PSSSDQNWHN DLTGVSLHVK    60
IPKSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNHFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTEX ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 81       moltype = AA  length = 512
FEATURE             Location/Qualifiers
SITE                63
                    note = misc_feature - Xaa can be any naturally occurring
                    amino acid except Lys or Arg
SITE                225
                    note = misc_feature - Xaa can be any naturally occurring
                    amino acid except Lys or Arg
source              1..512
                    mol_type = protein
                    organism = Vesicular stomatitis virus
SEQUENCE: 81
MLRLFLFCFL ALGAHSKFTI VFPHHQKGNW KNVPSTYHYC PSSSDQNWHN DLTGVSLHVK    60
IPXSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNXFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTER ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 82       moltype = AA  length = 512
FEATURE             Location/Qualifiers
SITE                225
                    note = misc_feature - Xaa can be any naturally occurring
                    amino acid except Lys or Arg
SITE                370
                    note = misc_feature - Xaa can be any naturally occurring
                    amino acid except Lys or Arg
source              1..512
                    mol_type = protein
                    organism = Vesicular stomatitis virus
SEQUENCE: 82
MLRLFLFCFL ALGAHSKFTI VFPHHQKGNW KNVPSTYHYC PSSSDQNWHN DLTGVSLHVK    60
IPKSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNXFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPGSGP AFTIINGTLK YFETRYIRVD ISNPIIPHMV   360
GTMSGTTTEX ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 83       moltype = AA  length = 512
FEATURE             Location/Qualifiers
SITE                63
                    note = misc_feature - Xaa can be any naturally occurring
                    amino acid except Lys or Arg
SITE                225
                    note = misc_feature - Xaa can be any naturally occurring
                    amino acid except Lys or Arg
SITE                370
                    note = misc_feature - Xaa can be any naturally occurring
                    amino acid except Lys or Arg
source              1..512
                    mol_type = protein
                    organism = Vesicular stomatitis virus
```

```
SEQUENCE: 83
MLRLFLFCFL ALGAHSKFTI VFPHHQKGNW KNVPSTYHYC PSSSDQNWHN DLTGVSLHVK    60
IPXSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNXFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPSGP  AFTIINGTLK YFETRYIRVD ISNPIIPHMV   360
GTMSGTTTEX ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 84         moltype = AA  length = 512
FEATURE               Location/Qualifiers
SITE                  24
                      note = misc_feature - Xaa can be any naturally occurring
                        amino acid except Lys or Arg
SITE                  63
                      note = misc_feature - Xaa can be any naturally occurring
                        amino acid except Lys or Arg
SITE                  225
                      note = misc_feature - Xaa can be any naturally occurring
                        amino acid except Lys or Arg
SITE                  370
                      note = misc_feature - Xaa can be any naturally occurring
                        amino acid except Lys or Arg
source                1..512
                      mol_type = protein
                      organism = Vesicular stomatitis virus
SEQUENCE: 84
MLRLFLFCFL ALGAHSKFTI VFPXHQKGNW KNVPSTYHYC PSSSDQNWHN DLTGVSLHVK    60
IPXSHKAIQA DGWMCHAAKW VTTCDFRWYG PKYITHSIHS MSPTLEQCKT SIEQTKQGVW   120
INPGFPPQSC GYATVTDAEV VVVQATPHHV LVDEYTGEWI DSQLVGGKCS KEVCQTVHNS   180
TVWHADYKIT GLCESNLASV DITFFSEDGQ KTSLGKPNTG FRSNXFAYES GEKACRMQYC   240
TQWGIRLPSG VWFELVDKDL FQAAKLPECP RGSSISAPSQ TSVDVSLIQD VERILDYSLC   300
QETWSKIRAK LPVSPVDLSY LAPKNPSGP  AFTIINGTLK YFETRYIRVD ISNPIIPHMV   360
GTMSGTTTEX ELWNDWYPYE DVEIGPNGVL KTPTGFKFPL YMIGHGMLDS DLHKSSQAQV   420
FEHPHAKDAA SQLPDDETLF FGDTGLSKNP VELVEGWFSS WKSTLASFFL IIGLGVALIF   480
IIRIIVAIRY KYKGRKTQKI YNDVEMSRLG NK                                 512

SEQ ID NO: 85         moltype = AA  length = 501
FEATURE               Location/Qualifiers
SITE                  9
                      note = misc_feature - Xaa can be any naturally occurring
                        amino acid except Lys or Arg
SITE                  47
                      note = misc_feature - Xaa can be any naturally occurring
                        amino acid except Lys or Arg
source                1..501
                      mol_type = protein
                      organism = Vesicular stomatitis virus
SEQUENCE: 85
KIEIVFPQXT TGDWKRVPHE YNYCPTSADK NSHGTQTGIP VELTMPXGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNYF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVRQL   360
WDQWFPFGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                             501

SEQ ID NO: 86         moltype = AA  length = 501
FEATURE               Location/Qualifiers
SITE                  9
                      note = misc_feature - Xaa can be any naturally occurring
                        amino acid except Lys or Arg
SITE                  358
                      note = misc_feature - Xaa can be any naturally occurring
                        amino acid except Lys or Arg
source                1..501
                      mol_type = protein
                      organism = Vesicular stomatitis virus
SEQUENCE: 86
KIEIVFPQXT TGDWKRVPHE YNYCPTSADK NSHGTQTGIP VELTMPKGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNYF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVXQL   360
```

```
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 87           moltype = AA  length = 501
FEATURE                 Location/Qualifiers
SITE                    9
                        note = misc_feature - Xaa can be any naturally occurring
                         amino acid except Lys or Arg
SITE                    47
                        note = misc_feature - Xaa can be any naturally occurring
                         amino acid except Lys or Arg
SITE                    358
                        note = misc_feature - Xaa can be any naturally occurring
                         amino acid except Lys or Arg
source                  1..501
                        mol_type = protein
                        organism = Vesicular stomatitis virus
SEQUENCE: 87
KIEIVFPQXT TGDWKRVPHE YNYCPTSADK NSHGTQTGIP VELTMPXGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVXQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 88           moltype = AA  length = 501
FEATURE                 Location/Qualifiers
SITE                    47
                        note = misc_feature - Xaa can be any naturally occurring
                         amino acid except Lys or Arg
source                  1..501
                        mol_type = protein
                        organism = Vesicular stomatitis virus
SEQUENCE: 88
KIEIVFPQHT TGDWKRVPHE YNYCPTSADK NSHGTQTGIP VELTMPXGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVRQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 89           moltype = AA  length = 501
FEATURE                 Location/Qualifiers
SITE                    209
                        note = misc_feature - Xaa can be any naturally occurring
                         amino acid except Lys or Arg
SITE                    358
                        note = misc_feature - Xaa can be any naturally occurring
                         amino acid except Lys or Arg
source                  1..501
                        mol_type = protein
                        organism = Vesicular stomatitis virus
SEQUENCE: 89
KIEIVFPQHT TGDWKRVPHE YNYCPTSADK NSHGTQTGIP VELTMPKGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNXF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVXQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 90           moltype = AA  length = 501
FEATURE                 Location/Qualifiers
SITE                    47
                        note = misc_feature - Xaa can be any naturally occurring
                         amino acid except Lys or Arg
SITE                    209
                        note = misc_feature - Xaa can be any naturally occurring
                         amino acid except Lys or Arg
SITE                    358
```

```
                          note = misc_feature - Xaa can be any naturally occurring
                             amino acid except Lys or Arg
source                    1..501
                          mol_type = protein
                          organism = Vesicular stomatitis virus
SEQUENCE: 90
KIEIVFPQHT TGDWKRVPHE YNYCPTSADK NSHGTQTGIP VELTMPXGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNXF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVXQL   360
WDQWFPPGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                            501

SEQ ID NO: 91             moltype = AA   length = 501
FEATURE                   Location/Qualifiers
SITE                      9
                          note = misc_feature - Xaa can be any naturally occurring
                             amino acid except Lys or Arg
SITE                      47
                          note = misc_feature - Xaa can be any naturally occurring
                             amino acid except Lys or Arg
SITE                      209
                          note = misc_feature - Xaa can be any naturally occurring
                             amino acid except Lys or Arg
SITE                      358
                          note = misc_feature - Xaa can be any naturally occurring
                             amino acid except Lys or Arg
source                    1..501
                          mol_type = protein
                          organism = Vesicular stomatitis virus
SEQUENCE: 91
KIEIVFPQXT TGDWKRVPHE YNYCPTSADK NSHGTQTGIP VELTMPXGLT THQVDGFMCH    60
SALWMTTCDF RWYGPKYITH SIHNEEPTDY QCLEAIKAYK DGVSFNPGFP PQSCGYGTVT   120
DAEAHIVTVT PHSVKVDEYT GEWIDPHFIG GRCKGQICET VHNSTKWFTS SDGESVCSQL   180
FTLVGGTFFS DSEEITSMGL PETGIRSNXF PYVSTEGICK MPFCRKPGYK LKNDLWFQIT   240
DPDLDKTVRD LPHIKDCDLS SSIVTPGEHA TDISLISDVE RILDYALCQN TWSKIEAGEP   300
ITPVDLSYLG PKNPGAGPVF TIINGSLHYF MSKYLRVELE SPVIPRMEGK VAGTRIVXQL   360
WDQWFPPGEV EIGPNGVLKT KQGYKFPLHI IGTGEVDNDI KMERIVKHWE HPHIEAAQTF   420
LKKDDTEEVL YYGDTGVSKN PVELVEGWFS GWRSSIMGVL AVIIGFVILI FLIRLIGVLS   480
SLFRQKRRPI YKSDVEMAHF R                                            501

SEQ ID NO: 92             moltype = AA   length = 517
FEATURE                   Location/Qualifiers
SITE                      25
                          note = misc_feature - Xaa can be any naturally occurring
                             amino acid except Lys or Arg
SITE                      63
                          note = misc_feature - Xaa can be any naturally occurring
                             amino acid except Lys or Arg
source                    1..517
                          mol_type = protein
                          organism = Vesicular stomatitis virus
SEQUENCE: 92
MLSYLIFALV VSPILGKIEI VFPQXTTGDW KRVPHEYNYC PTSADKNSHG TQTGIPVELT    60
MPXGLTTHQV DGFMCHSALW MTTCDFRWYG PKYITHSIHN EEPTDYQCLE AIKAYKDGVS   120
FNPGFPPQSC GYGTVTDAEA HIVTVTPHSV KVDEYTDPHF IGGRCK GQICETVHNS       180
TKWFTSSDGE SVCSQLFTLV GGTFFSDSEE ITSMGLPETG IRSNYFPYVS TEGICKMPFC   240
RKPGYKLKND LWFQITDPDL DKTVRDLPHI KDCDLSSSIV TPGEHATDIS LISDVERILD   300
YALCQNTWSK IEAGEPITPV DLSYLGPKNP GAGPVFTIIN GSLHYFMSKY LRVELESPVI   360
PRMEGKVAGT RIVRQLWDQW FPFGEVEIGP NGVLKTKQGY KFPLHIIGTG EVDNDIKMER   420
IVKHWEHPHI EAAQTFLKKD DTEEVLYYGD TGVSKNPVEL VEGWFSGWRS SIMGVLAVII   480
GFVILIFLIR LIGVLSSLFR QKRRPIYKSD VEMAHFR                            517

SEQ ID NO: 93             moltype = AA   length = 517
FEATURE                   Location/Qualifiers
SITE                      25
                          note = misc_feature - Xaa can be any naturally occurring
                             amino acid except Lys or Arg
SITE                      374
                          note = misc_feature - Xaa can be any naturally occurring
                             amino acid except Lys or Arg
source                    1..517
                          mol_type = protein
                          organism = Vesicular stomatitis virus
SEQUENCE: 93
MLSYLIFALV VSPILGKIEI VFPQXTTGDW KRVPHEYNYC PTSADKNSHG TQTGIPVELT    60
```

```
MPKGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNYFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVXQLWDQW FPFGEVEIGP NGVLKTKQGY KFPLHIIGTG EVDNDIKMER  420
IVKHWEHPHI EAAQTFLKKD DTEEVLYYGD TGVSKNPVEL VEGWFSGWRS SIMGVLAVII  480
GFVILIFLIR LIGVLSSLFR QKRRPIYKSD VEMAHFR                          517

SEQ ID NO: 94          moltype = AA  length = 517
FEATURE                Location/Qualifiers
SITE                   25
                       note = misc_feature - Xaa can be any naturally occurring
                        amino acid except Lys or Arg
SITE                   63
                       note = misc_feature - Xaa can be any naturally occurring
                        amino acid except Lys or Arg
SITE                   374
                       note = misc_feature - Xaa can be any naturally occurring
                        amino acid except Lys or Arg
source                 1..517
                       mol_type = protein
                       organism = Vesicular stomatitis virus
SEQUENCE: 94
MLSYLIFALV VSPILGKIEI VFPQXTTGDW KRVPHEYNYC PTSADKNSHG TQTGIPVELT   60
MPXGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNYFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVXQLWDQW FPFGEVEIGP NGVLKTKQGY KFPLHIIGTG EVDNDIKMER  420
IVKHWEHPHI EAAQTFLKKD DTEEVLYYGD TGVSKNPVEL VEGWFSGWRS SIMGVLAVII  480
GFVILIFLIR LIGVLSSLFR QKRRPIYKSD VEMAHFR                          517

SEQ ID NO: 95          moltype = AA  length = 517
FEATURE                Location/Qualifiers
SITE                   63
                       note = misc_feature - Xaa can be any naturally occurring
                        amino acid except Lys or Arg
SITE                   225
                       note = misc_feature - Xaa can be any naturally occurring
                        amino acid except Lys or Arg
source                 1..517
                       mol_type = protein
                       organism = Vesicular stomatitis virus
SEQUENCE: 95
MLSYLIFALV VSPILGKIEI VFPQHTTGDW KRVPHEYNYC PTSADKNSHG TQTGIPVELT   60
MPXGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNXFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVRQLWDQW FPFGEVEIGP NGVLKTKQGY KFPLHIIGTG EVDNDIKMER  420
IVKHWEHPHI EAAQTFLKKD DTEEVLYYGD TGVSKNPVEL VEGWFSGWRS SIMGVLAVII  480
GFVILIFLIR LIGVLSSLFR QKRRPIYKSD VEMAHFR                          517

SEQ ID NO: 96          moltype = AA  length = 517
FEATURE                Location/Qualifiers
SITE                   225
                       note = misc_feature - Xaa can be any naturally occurring
                        amino acid except Lys or Arg
SITE                   374
                       note = misc_feature - Xaa can be any naturally occurring
                        amino acid except Lys or Arg
source                 1..517
                       mol_type = protein
                       organism = Vesicular stomatitis virus
SEQUENCE: 96
MLSYLIFALV VSPILGKIEI VFPQHTTGDW KRVPHEYNYC PTSADKNSHG TQTGIPVELT   60
MPKGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNXFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVXQLWDQW FPFGEVEIGP NGVLKTKQGY KFPLHIIGTG EVDNDIKMER  420
IVKHWEHPHI EAAQTFLKKD DTEEVLYYGD TGVSKNPVEL VEGWFSGWRS SIMGVLAVII  480
GFVILIFLIR LIGVLSSLFR QKRRPIYKSD VEMAHFR                          517

SEQ ID NO: 97          moltype = AA  length = 517
```

| FEATURE | Location/Qualifiers |
|---|---|
| SITE | 63 |
| | note = misc_feature - Xaa can be any naturally occurring amino acid except Lys or Arg |
| SITE | 225 |
| | note = misc_feature - Xaa can be any naturally occurring amino acid except Lys or Arg |
| SITE | 374 |
| | note = misc_feature - Xaa can be any naturally occurring amino acid except Lys or Arg |
| source | 1..517 |
| | mol_type = protein |
| | organism = Vesicular stomatitis virus |

SEQUENCE: 97

```
MLSYLIFALV VSPILGKIEI VFPQHTTGDW KRVPHEYNYC PTSADKNSHG TQTGIPVELT   60
MPXGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNXFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVXQLWDQW FPFGEVEIGP NGVLKTKQGY KFPLHIIGTG EVDNDIKMER  420
IVKHWEHPHI EAAQTFLKKD DTEEVYYGD TGVSKNPVEL VEGWFSGWRS SIMGVLAVII  480
GFVILIFLIR LIGVLSSLFR QKRRPIYKSD VEMAHFR                           517
```

| SEQ ID NO: 98 | moltype = AA length = 517 |
|---|---|
| FEATURE | Location/Qualifiers |
| SITE | 25 |
| | note = misc_feature - Xaa can be any naturally occurring amino acid except Lys or Arg |
| SITE | 63 |
| | note = misc_feature - Xaa can be any naturally occurring amino acid except Lys or Arg |
| SITE | 225 |
| | note = misc_feature - Xaa can be any naturally occurring amino acid except Lys or Arg |
| SITE | 374 |
| | note = misc_feature - Xaa can be any naturally occurring amino acid except Lys or Arg |
| source | 1..517 |
| | mol_type = protein |
| | organism = Vesicular stomatitis virus |

SEQUENCE: 98

```
MLSYLIFALV VSPILGKIEI VFPQXTTGDW KRVPHEYNYC PTSADKNSHG TQTGIPVELT   60
MPXGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNXFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVXQLWDQW FPFGEVEIGP NGVLKTKQGY KFPLHIIGTG EVDNDIKMER  420
IVKHWEHPHI EAAQTFLKKD DTEEVYYGD TGVSKNPVEL VEGWFSGWRS SIMGVLAVII  480
GFVILIFLIR LIGVLSSLFR QKRRPIYKSD VEMAHFR                           517
```

| SEQ ID NO: 99 | moltype = AA length = 502 |
|---|---|
| FEATURE | Location/Qualifiers |
| SITE | 8 |
| | note = misc_feature - Xaa can be any naturally occurring amino acid except Lys or Arg |
| SITE | 47 |
| | note = misc_feature - Xaa can be any naturally occurring amino acid except Lys or Arg |
| source | 1..502 |
| | mol_type = protein |
| | organism = Vesicular stomatitis virus |

SEQUENCE: 99

```
KITISFPXSL KGDWRPVPKG YNYCPTSADK NLHGDLIDIG LRLRAPXSFK GISADGWMCH   60
AARWITTCDF RWYGPKYITH SIHSFRPSND QCKEAIRLTN EGNWINPGFP PQSCGYASVT  120
DSESVVVTVT KHQVLVDEYS GSWIDSQFPG GSCTSPICDT VHNSTLWHAD HTLDSICDQE  180
FVAMDAVLFT ESGKFEEFGK PNSGIRSNYF PYESLKDVCQ MDPCKRKGFK LPSGVWFEIE  240
DAEKSHKAQV ELKIKRCPHG AVISAPNQNA ADINLIMDVE RILDYSLCQA TWSKIQNKEA  300
LTPIDISYLG PKNPGPGPAF TIINGTLHYF NTRYIRVDIA GPVTKEITGF VSGTSTSRVL  360
WDQWFPYGEN SIGPNGLLKT ASGYKYPLFM VGTGVLDADI HKLGEATVIE HPHAKEAQKV  420
VDDSEVIFFG DTGVSKNPVE VVEGWFSGWR SSLMSIFGII LLIVCLVLIV RILIALKYCC  480
VRHKKRTIYK EDLEMGRIPR RA                                           502
```

| SEQ ID NO: 100 | moltype = AA length = 502 |
|---|---|
| FEATURE | Location/Qualifiers |
| SITE | 8 |
| | note = misc_feature - Xaa can be any naturally occurring amino acid except Lys or Arg |

```
SITE                        358
                            note = misc_feature - Xaa can be any naturally occurring
                             amino acid except Lys or Arg
source                      1..502
                            mol_type = protein
                            organism = Vesicular stomatitis virus
SEQUENCE: 100
KITISFPXSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT   120
DSESVVVTVT KHQVLVDEYS GSWIDSQFPG GSCTSPICDT VHNSTLWHAD HTLDSICDQE   180
FVAMDAVLFT ESGKFEEFGK PNSGIRSNYF PYESLKDVCQ MDFCKRKGFK LPSGVWFEIE   240
DAEKSHKAQV ELKIKRCPHG AVISAPNQNA ADINLIMDVE RILDYSLCQA TWSKIQNKEA   300
LTPIDISYLG PKNPGPGPAF TIINGTLHYF NTRYIRVDIA GPVTKEITGF VSGTSTSXVL   360
WDQWFPYGEN SIGPNGLLKT ASGYKYPLFM VGTGVLDADI HKLGEATVIE HPHAKEAQKV   420
VDDSEVIFFG DTGVSKNPVE VVEGWFSGWR SSLMSIFGII LLIVCLVLIV RILIALKYCC   480
VRHKKRTIYK EDLEMGRIPR RA                                           502

SEQ ID NO: 101              moltype = AA   length = 502
FEATURE                     Location/Qualifiers
SITE                        8
                            note = misc_feature - Xaa can be any naturally occurring
                             amino acid except Lys or Arg
SITE                        47
                            note = misc_feature - Xaa can be any naturally occurring
                             amino acid except Lys or Arg
SITE                        358
                            note = misc_feature - Xaa can be any naturally occurring
                             amino acid except Lys or Arg
source                      1..502
                            mol_type = protein
                            organism = Vesicular stomatitis virus
SEQUENCE: 101
KITISFPXSL KGDWRPVPKG YNYCPTSADK NLHGDLIDIG LRLRAPXSFK GISADGWMCH    60
AARWITTCDF RWYGPKYITH SIHSFRPSND QCKEAIRLTN EGNWINPGFP PQSCGYASVT   120
DSESVVVTVT KHQVLVDEYS GSWIDSQFPG GSCTSPICDT VHNSTLWHAD HTLDSICDQE   180
FVAMDAVLFT ESGKFEEFGK PNSGIRSNYF PYESLKDVCQ MDFCKRKGFK LPSGVWFEIE   240
DAEKSHKAQV ELKIKRCPHG AVISAPNQNA ADINLIMDVE RILDYSLCQA TWSKIQNKEA   300
LTPIDISYLG PKNPGPGPAF TIINGTLHYF NTRYIRVDIA GPVTKEITGF VSGTSTSXVL   360
WDQWFPYGEN SIGPNGLLKT ASGYKYPLFM VGTGVLDADI HKLGEATVIE HPHAKEAQKV   420
VDDSEVIFFG DTGVSKNPVE VVEGWFSGWR SSLMSIFGII LLIVCLVLIV RILIALKYCC   480
VRHKKRTIYK EDLEMGRIPR RA                                           502

SEQ ID NO: 102              moltype = AA   length = 502
FEATURE                     Location/Qualifiers
SITE                        47
                            note = misc_feature - Xaa can be any naturally occurring
                             amino acid except Lys or Arg
SITE                        209
                            note = misc_feature - Xaa can be any naturally occurring
                             amino acid except Lys or Arg
source                      1..502
                            mol_type = protein
                            organism = Vesicular stomatitis virus
SEQUENCE: 102
KITISFPQSL KGDWRPVPKG YNYCPTSADK NLHGDLIDIG LRLRAPXSFK GISADGWMCH    60
AARWITTCDF RWYGPKYITH SIHSFRPSND QCKEAIRLTN EGNWINPGFP PQSCGYASVT   120
DSESVVVTVT KHQVLVDEYS GSWIDSQFPG GSCTSPICDT VHNSTLWHAD HTLDSICDQE   180
FVAMDAVLFT ESGKFEEFGK PNSGIRSNXF PYESLKDVCQ MDFCKRKGFK LPSGVWFEIE   240
DAEKSHKAQV ELKIKRCPHG AVISAPNQNA ADINLIMDVE RILDYSLCQA TWSKIQNKEA   300
LTPIDISYLG PKNPGPGPAF TIINGTLHYF NTRYIRVDIA GPVTKEITGF VSGTSTSRVL   360
WDQWFPYGEN SIGPNGLLKT ASGYKYPLFM VGTGVLDADI HKLGEATVIE HPHAKEAQKV   420
VDDSEVIFFG DTGVSKNPVE VVEGWFSGWR SSLMSIFGII LLIVCLVLIV RILIALKYCC   480
VRHKKRTIYK EDLEMGRIPR RA                                           502

SEQ ID NO: 103              moltype = AA   length = 502
FEATURE                     Location/Qualifiers
SITE                        209
                            note = misc_feature - Xaa can be any naturally occurring
                             amino acid except Lys or Arg
SITE                        358
                            note = misc_feature - Xaa can be any naturally occurring
                             amino acid except Lys or Arg
source                      1..502
                            mol_type = protein
                            organism = Vesicular stomatitis virus
SEQUENCE: 103
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT   120
DSESVVVTVT KHQVLVDEYS GSWIDSQFPG GSCTSPICDT VHNSTLWHAD HTLDSICDQE   180
```

```
FVAMDAVLFT ESGKFEEFGK PNSGIRSNXF PYESLKDVCQ MDFCKRKGFK LPSGVWFEIE      240
DAEKSHKAQV ELKIKRCPHG AVISAPNQNA ADINLIMDVE RILDYSLCQA TWSKIQNKEA      300
LTPIDISYLG PKNPGPGPAF TIINGTLHYF NTRYIRVDIA GPVTKEITGF VSGTSTSXVL      360
WDQWFPYGEN SIGPNGLLKT ASGYKYPLFM VGTGVLDADI HKLGEATVIE HPAKEAQKV       420
VDDSEVIFFG DTGVSKNPVE VVEGWFSGWR SSLMSIFGII LLIVCLVLIV RILIALKYCC      480
VRHKKRTIYK EDLEMGRIPR RA                                              502

SEQ ID NO: 104           moltype = AA  length = 502
FEATURE                  Location/Qualifiers
SITE                     47
                         note = misc_feature - Xaa can be any naturally occurring
                           amino acid except Lys or Arg
SITE                     209
                         note = misc_feature - Xaa can be any naturally occurring
                           amino acid except Lys or Arg
SITE                     358
                         note = misc_feature - Xaa can be any naturally occurring
                           amino acid except Lys or Arg
source                   1..502
                         mol_type = protein
                         organism = Vesicular stomatitis virus
SEQUENCE: 104
KITISFPQSL KGDWRPVPKG YNYCPTSADK NLHGDLIDIG LRLRAPXSFK GISADGWMCH       60
AARWITTCDF RWYGPKYITH SIHSFRPSND QCKEAIRLTN EGNWINPGFP PQSCGYASVT      120
DSESVVVTVT KHQVLVDEYS GSWIDSQFPG GSCTSPICDT VHNSTLWHAD HTLDSICDQE      180
FVAMDAVLFT ESGKFEEFGK PNSGIRSNXF PYESLKDVCQ MDFCKRKGFK LPSGVWFEIE      240
DAEKSHKAQV ELKIKRCPHG AVISAPNQNA ADINLIMDVE RILDYSLCQA TWSKIQNKEA      300
LTPIDISYLG PKNPGPGPAF TIINGTLHYF NTRYIRVDIA GPVTKEITGF VSGTSTSXVL      360
WDQWFPYGEN SIGPNGLLKT ASGYKYPLFM VGTGVLDADI HKLGEATVIE HPAKEAQKV       420
VDDSEVIFFG DTGVSKNPVE VVEGWFSGWR SSLMSIFGII LLIVCLVLIV RILIALKYCC      480
VRHKKRTIYK EDLEMGRIPR RA                                              502

SEQ ID NO: 105           moltype = AA  length = 502
FEATURE                  Location/Qualifiers
SITE                     8
                         note = misc_feature - Xaa can be any naturally occurring
                           amino acid except Lys or Arg
SITE                     47
                         note = misc_feature - Xaa can be any naturally occurring
                           amino acid except Lys or Arg
SITE                     209
                         note = misc_feature - Xaa can be any naturally occurring
                           amino acid except Lys or Arg
SITE                     358
                         note = misc_feature - Xaa can be any naturally occurring
                           amino acid except Lys or Arg
source                   1..502
                         mol_type = protein
                         organism = Vesicular stomatitis virus
SEQUENCE: 105
KITISFPXSL KGDWRPVPKG YNYCPTSADK NLHGDLIDIG LRLRAPXSFK GISADGWMCH       60
AARWITTCDF RWYGPKYITH SIHSFRPSND QCKEAIRLTN EGNWINPGFP PQSCGYASVT      120
DSESVVVTVT KHQVLVDEYS GSWIDSQFPG GSCTSPICDT VHNSTLWHAD HTLDSICDQE      180
FVAMDAVLFT ESGKFEEFGK PNSGIRSNXF PYESLKDVCQ MDFCKRKGFK LPSGVWFEIE      240
DAEKSHKAQV ELKIKRCPHG AVISAPNQNA ADINLIMDVE RILDYSLCQA TWSKIQNKEA      300
LTPIDISYLG PKNPGPGPAF TIINGTLHYF NTRYIRVDIA GPVTKEITGF VSGTSTSXVL      360
WDQWFPYGEN SIGPNGLLKT ASGYKYPLFM VGTGVLDADI HKLGEATVIE HPAKEAQKV       420
VDDSEVIFFG DTGVSKNPVE VVEGWFSGWR SSLMSIFGII LLIVCLVLIV RILIALKYCC      480
VRHKKRTIYK EDLEMGRIPR RA                                              502

SEQ ID NO: 106           moltype = AA  length = 523
FEATURE                  Location/Qualifiers
SITE                     29
                         note = misc_feature - Xaa can be any naturally occurring
                           amino acid except Lys or Arg
SITE                     68
                         note = misc_feature - Xaa can be any naturally occurring
                           amino acid except Lys or Arg
source                   1..523
                         mol_type = protein
                         organism = Vesicular stomatitis virus
SEQUENCE: 106
MKMKMVIAGL ILCIGILPAI GKITISFPXS LKGDWRPVPK GYNYCPTSAD KNLHGDLIDI       60
GLRLRAPXSF KGISADGWMC HAARWITTCD FRWYGPKYIT HSIHSFRPSN DQCKEAIRLT      120
NEGNWINPGF PPQSCGYASV TDSESVVVTV TKHQVLVDEY SGSWIDSQFP GGSCTSPICD      180
TVHNSTLWHA DHTLDSICDQ EFVAMDAVLF TESGKFEEFG KPNSGIRSNY PYESLKDVC       240
QMDFCKRKGF KLPSGVWFEI EDAEKSHKAQ VELKIKRCPH GAVISAPNQN AADINLIMDV      300
ERILDYSLCQ ATWSKIQNKE ALTPIDISYL GPKNPGPGPA FTIINGTLHY FNTRYIRVDI      360
AGPVTKEITG FVSGTSTSRV LWDQWFPYGE NSIGPNGLLK TASGYKYPLF MVGTGVLDAD      420
```

```
IHKLGEATVI EHPHAKEAQK VVDDSEVIFF GDTGVSKNPV EVVEGWFSGW RSSLMSIFGI    480
ILLIVCLVLI VRILIALKYC CVRHKKRTIY KEDLEMGRIP RRA                      523

SEQ ID NO: 107          moltype = AA  length = 523
FEATURE                 Location/Qualifiers
SITE                    29
                        note = misc_feature - Xaa can be any naturally occurring
                         amino acid except Lys or Arg
SITE                    379
                        note = misc_feature - Xaa can be any naturally occurring
                         amino acid except Lys or Arg
source                  1..523
                        mol_type = protein
                        organism = Vesicular stomatitis virus
SEQUENCE: 107
MKMKMVIAGL ILCIGILPAI GKITISFPXS LKGDWRPVPK GYNYCPTSAD KNLHGDLIDI    60
GLRLRAPKSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNY FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                    523

SEQ ID NO: 108          moltype = AA  length = 523
FEATURE                 Location/Qualifiers
SITE                    29
                        note = misc_feature - Xaa can be any naturally occurring
                         amino acid except Lys or Arg
SITE                    68
                        note = misc_feature - Xaa can be any naturally occurring
                         amino acid except Lys or Arg
SITE                    379
                        note = misc_feature - Xaa can be any naturally occurring
                         amino acid except Lys or Arg
source                  1..523
                        mol_type = protein
                        organism = Vesicular stomatitis virus
SEQUENCE: 108
MKMKMVIAGL ILCIGILPAI GKITISFPXS LKGDWRPVPK GYNYCPTSAD KNLHGDLIDI    60
GLRLRAPXSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNY FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                    523

SEQ ID NO: 109          moltype = AA  length = 523
FEATURE                 Location/Qualifiers
SITE                    68
                        note = misc_feature - Xaa can be any naturally occurring
                         amino acid except Lys or Arg
SITE                    230
                        note = misc_feature - Xaa can be any naturally occurring
                         amino acid except Lys or Arg
source                  1..523
                        mol_type = protein
                        organism = Vesicular stomatitis virus
SEQUENCE: 109
MKMKMVIAGL ILCIGILPAI GKITISFPQS LKGDWRPVPK GYNYCPTSAD KNLHGDLIDI    60
GLRLRAPXSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNX FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSRV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                    523

SEQ ID NO: 110          moltype = AA  length = 523
FEATURE                 Location/Qualifiers
SITE                    230
                        note = misc_feature - Xaa can be any naturally occurring
                         amino acid except Lys or Arg
SITE                    379
                        note = misc_feature - Xaa can be any naturally occurring
```

```
                          amino acid except Lys or Arg
source                    1..523
                          mol_type = protein
                          organism = Vesicular stomatitis virus
SEQUENCE: 110
MKMKMVIAGL ILCIGILPAI GKITISFPQS LKGDWRPVPK GYNYCPTSAD KNLHGDLIDI    60
GLRLRAPKSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNX FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                     523

SEQ ID NO: 111            moltype = AA   length = 523
FEATURE                   Location/Qualifiers
SITE                      68
                          note = misc_feature - Xaa can be any naturally occurring
                           amino acid except Lys or Arg
SITE                      230
                          note = misc_feature - Xaa can be any naturally occurring
                           amino acid except Lys or Arg
SITE                      379
                          note = misc_feature - Xaa can be any naturally occurring
                           amino acid except Lys or Arg
source                    1..523
                          mol_type = protein
                          organism = Vesicular stomatitis virus
SEQUENCE: 111
MKMKMVIAGL ILCIGILPAI GKITISFPQS LKGDWRPVPK GYNYCPTSAD KNLHGDLIDI    60
GLRLRAPXSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNX FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                     523

SEQ ID NO: 112            moltype = AA   length = 523
FEATURE                   Location/Qualifiers
SITE                      29
                          note = misc_feature - Xaa can be any naturally occurring
                           amino acid except Lys or Arg
SITE                      68
                          note = misc_feature - Xaa can be any naturally occurring
                           amino acid except Lys or Arg
SITE                      230
                          note = misc_feature - Xaa can be any naturally occurring
                           amino acid except Lys or Arg
SITE                      379
                          note = misc_feature - Xaa can be any naturally occurring
                           amino acid except Lys or Arg
source                    1..523
                          mol_type = protein
                          organism = Vesicular stomatitis virus
SEQUENCE: 112
MKMKMVIAGL ILCIGILPAI GKITISFPXS LKGDWRPVPK GYNYCPTSAD KNLHGDLIDI    60
GLRLRAPXSF KGISADGWMC HAARWITTCD FRWYGPKYIT HSIHSFRPSN DQCKEAIRLT   120
NEGNWINPGF PPQSCGYASV TDSESVVVTV TKHQVLVDEY SGSWIDSQFP GGSCTSPICD   180
TVHNSTLWHA DHTLDSICDQ EFVAMDAVLF TESGKFEEFG KPNSGIRSNX FPYESLKDVC   240
QMDFCKRKGF KLPSGVWFEI EDAEKSHKAQ VELKIKRCPH GAVISAPNQN AADINLIMDV   300
ERILDYSLCQ ATWSKIQNKE ALTPIDISYL GPKNPGPGPA FTIINGTLHY FNTRYIRVDI   360
AGPVTKEITG FVSGTSTSXV LWDQWFPYGE NSIGPNGLLK TASGYKYPLF MVGTGVLDAD   420
IHKLGEATVI EHPHAKEAQK VVDDSEVIFF GDTGVSKNPV EVVEGWFSGW RSSLMSIFGI   480
ILLIVCLVLI VRILIALKYC CVRHKKRTIY KEDLEMGRIP RRA                     523

SEQ ID NO: 113            moltype = AA   length = 494
FEATURE                   Location/Qualifiers
SITE                      8
                          note = misc_feature - Xaa can be any naturally occurring
                           amino acid except Lys or Arg
SITE                      47
                          note = misc_feature - Xaa can be any naturally occurring
                           amino acid except Lys or Arg
source                    1..494
                          mol_type = protein
                          organism = Vesicular stomatitis virus
```

```
SEQUENCE: 113
KFTIVFPXSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 114         moltype = AA  length = 494
FEATURE                Location/Qualifiers
SITE                   8
                       note = misc_feature - Xaa can be any naturally occurring
                        amino acid except Lys or Arg
SITE                   354
                       note = misc_feature - Xaa can be any naturally occurring
                        amino acid except Lys or Arg
source                 1..494
                       mol_type = protein
                       organism = Vesicular stomatitis virus
SEQUENCE: 114
KFTIVFPXSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKXELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 115         moltype = AA  length = 494
FEATURE                Location/Qualifiers
SITE                   8
                       note = misc_feature - Xaa can be any naturally occurring
                        amino acid except Lys or Arg
SITE                   47
                       note = misc_feature - Xaa can be any naturally occurring
                        amino acid except Lys or Arg
SITE                   354
                       note = misc_feature - Xaa can be any naturally occurring
                        amino acid except Lys or Arg
source                 1..494
                       mol_type = protein
                       organism = Vesicular stomatitis virus
SEQUENCE: 115
KFTIVFPXSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKXELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 116         moltype = AA  length = 494
FEATURE                Location/Qualifiers
SITE                   47
                       note = misc_feature - Xaa can be any naturally occurring
                        amino acid except Lys or Arg
SITE                   209
                       note = misc_feature - Xaa can be any naturally occurring
                        amino acid except Lys or Arg
source                 1..494
                       mol_type = protein
                       organism = Vesicular stomatitis virus
SEQUENCE: 116
KFTIVFPQSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNXF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494
```

```
SEQ ID NO: 117           moltype = AA  length = 494
FEATURE                  Location/Qualifiers
SITE                     209
                         note = misc_feature - Xaa can be any naturally occurring
                          amino acid except Lys or Arg
SITE                     354
                         note = misc_feature - Xaa can be any naturally occurring
                          amino acid except Lys or Arg
source                   1..494
                         mol_type = protein
                         organism = Vesicular stomatitis virus
SEQUENCE: 117
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNXF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKXELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 118           moltype = AA  length = 494
FEATURE                  Location/Qualifiers
SITE                     47
                         note = misc_feature - Xaa can be any naturally occurring
                          amino acid except Lys or Arg
SITE                     209
                         note = misc_feature - Xaa can be any naturally occurring
                          amino acid except Lys or Arg
SITE                     354
                         note = misc_feature - Xaa can be any naturally occurring
                          amino acid except Lys or Arg
source                   1..494
                         mol_type = protein
                         organism = Vesicular stomatitis virus
SEQUENCE: 118
KFTIVFPQSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNXF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKXELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 119           moltype = AA  length = 494
FEATURE                  Location/Qualifiers
SITE                     8
                         note = misc_feature - Xaa can be any naturally occurring
                          amino acid except Lys or Arg
SITE                     47
                         note = misc_feature - Xaa can be any naturally occurring
                          amino acid except Lys or Arg
SITE                     209
                         note = misc_feature - Xaa can be any naturally occurring
                          amino acid except Lys or Arg
SITE                     354
                         note = misc_feature - Xaa can be any naturally occurring
                          amino acid except Lys or Arg
source                   1..494
                         mol_type = protein
                         organism = Vesicular stomatitis virus
SEQUENCE: 119
KFTIVFPXSQ KGDWKDVPPN YRYCPSSADQ NWHGDLLGVN IRAKMPXVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNXF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKXELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 120           moltype = AA  length = 511
FEATURE                  Location/Qualifiers
SITE                     25
```

```
                            note = misc_feature - Xaa can be any naturally occurring
                                amino acid except Lys or Arg
SITE                        64
                            note = misc_feature - Xaa can be any naturally occurring
                                amino acid except Lys or Arg
source                      1..511
                            mol_type = protein
                            organism = Vesicular stomatitis virus
SEQUENCE: 120
MTPAFILCML LAGSSWAKFT IVFPXSQKGD WKDVPPNYRY CPSSADQNWH GDLLGVNIRA    60
KMPXVHKAIK ADGWMCHAAK WVTTCDYRWY GPQYITHSIH SFIPTKAQCE ESIKQTKEGV   120
WINPGFPPKN CGYASVSDAE SIIVQATAHS VMIDEYSGDW LDSQFPTGRC TGSTCETIHN   180
STLWYADYQV TGLCDSALVS TEVTFYSEDG LMTSIGRQNT GYRSNYFPYE KGAAACRMKY   240
CTHEGIRLPS GVWFEMVDKE LLESVQMPEC PAGLTISAPT QTSVDVSLIL DVERMLDYSL   300
CQETWSKVHS GLPISPVDLG YIAPKNPGAG PAFTIVNGTL KYFDTRYLRI DIEGPVLKKM   360
TGKVSGTPTK RELWTEWFPY DDVEIGPNGV LKTPEGYKFP LYMIGHGLLD SDLQKTSQAE   420
VFHHPQIAEA VQKLPDDETL FFGDTGISKN PVEVIEGWFS NWRSSVMAIV FAILLLVITV   480
LMVRLCVAFR HFCCQKRHKI YNDLEMNQLR R                                 511

SEQ ID NO: 121              moltype = AA   length = 511
FEATURE                     Location/Qualifiers
SITE                        25
                            note = misc_feature - Xaa can be any naturally occurring
                                amino acid except Lys or Arg
SITE                        371
                            note = misc_feature - Xaa can be any naturally occurring
                                amino acid except Lys or Arg
source                      1..511
                            mol_type = protein
                            organism = Vesicular stomatitis virus
SEQUENCE: 121
MTPAFILCML LAGSSWAKFT IVFPXSQKGD WKDVPPNYRY CPSSADQNWH GDLLGVNIRA    60
KMPKVHKAIK ADGWMCHAAK WVTTCDYRWY GPQYITHSIH SFIPTKAQCE ESIKQTKEGV   120
WINPGFPPKN CGYASVSDAE SIIVQATAHS VMIDEYSGDW LDSQFPTGRC TGSTCETIHN   180
STLWYADYQV TGLCDSALVS TEVTFYSEDG LMTSIGRQNT GYRSNYFPYE KGAAACRMKY   240
CTHEGIRLPS GVWFEMVDKE LLESVQMPEC PAGLTISAPT QTSVDVSLIL DVERMLDYSL   300
CQETWSKVHS GLPISPVDLG YIAPKNPGAG PAFTIVNGTL KYFDTRYLRI DIEGPVLKKM   360
TGKVSGTPTK XELWTEWFPY DDVEIGPNGV LKTPEGYKFP LYMIGHGLLD SDLQKTSQAE   420
VFHHPQIAEA VQKLPDDETL FFGDTGISKN PVEVIEGWFS NWRSSVMAIV FAILLLVITV   480
LMVRLCVAFR HFCCQKRHKI YNDLEMNQLR R                                 511

SEQ ID NO: 122              moltype = AA   length = 511
FEATURE                     Location/Qualifiers
SITE                        25
                            note = misc_feature - Xaa can be any naturally occurring
                                amino acid except Lys or Arg
SITE                        64
                            note = misc_feature - Xaa can be any naturally occurring
                                amino acid except Lys or Arg
SITE                        371
                            note = misc_feature - Xaa can be any naturally occurring
                                amino acid except Lys or Arg
source                      1..511
                            mol_type = protein
                            organism = Vesicular stomatitis virus
SEQUENCE: 122
MTPAFILCML LAGSSWAKFT IVFPXSQKGD WKDVPPNYRY CPSSADQNWH GDLLGVNIRA    60
KMPXVHKAIK ADGWMCHAAK WVTTCDYRWY GPQYITHSIH SFIPTKAQCE ESIKQTKEGV   120
WINPGFPPKN CGYASVSDAE SIIVQATAHS VMIDEYSGDW LDSQFPTGRC TGSTCETIHN   180
STLWYADYQV TGLCDSALVS TEVTFYSEDG LMTSIGRQNT GYRSNYFPYE KGAAACRMKY   240
CTHEGIRLPS GVWFEMVDKE LLESVQMPEC PAGLTISAPT QTSVDVSLIL DVERMLDYSL   300
CQETWSKVHS GLPISPVDLG YIAPKNPGAG PAFTIVNGTL KYFDTRYLRI DIEGPVLKKM   360
TGKVSGTPTK XELWTEWFPY DDVEIGPNGV LKTPEGYKFP LYMIGHGLLD SDLQKTSQAE   420
VFHHPQIAEA VQKLPDDETL FFGDTGISKN PVEVIEGWFS NWRSSVMAIV FAILLLVITV   480
LMVRLCVAFR HFCCQKRHKI YNDLEMNQLR R                                 511

SEQ ID NO: 123              moltype = AA   length = 511
FEATURE                     Location/Qualifiers
SITE                        64
                            note = misc_feature - Xaa can be any naturally occurring
                                amino acid except Lys or Arg
SITE                        226
                            note = misc_feature - Xaa can be any naturally occurring
                                amino acid except Lys or Arg
source                      1..511
                            mol_type = protein
                            organism = Vesicular stomatitis virus
SEQUENCE: 123
MTPAFILCML LAGSSWAKFT IVFPQSQKGD WKDVPPNYRY CPSSADQNWH GDLLGVNIRA    60
```

```
KMPXVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNXFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK RELWTEWFPY DDVEIGPNGV LKTPEGYKFP LYMIGHGLLD SDLQKTSQAE    420
VFHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                  511

SEQ ID NO: 124          moltype = AA   length = 511
FEATURE                 Location/Qualifiers
SITE                    226
                        note = misc_feature - Xaa can be any naturally occurring
                         amino acid except Lys or Arg
SITE                    371
                        note = misc_feature - Xaa can be any naturally occurring
                         amino acid except Lys or Arg
source                  1..511
                        mol_type = protein
                        organism = Vesicular stomatitis virus
SEQUENCE: 124
MTPAFILCML LAGSSWAKFT IVFPQSQKGD WKDVPPNYRY CPSSADQNWH GDLLGVNIRA     60
KMPKVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNXFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK XELWTEWFPY DDVEIGPNGV LKTPEGYKFP LYMIGHGLLD SDLQKTSQAE    420
VFHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                  511

SEQ ID NO: 125          moltype = AA   length = 511
FEATURE                 Location/Qualifiers
SITE                    64
                        note = misc_feature - Xaa can be any naturally occurring
                         amino acid except Lys or Arg
SITE                    226
                        note = misc_feature - Xaa can be any naturally occurring
                         amino acid except Lys or Arg
SITE                    371
                        note = misc_feature - Xaa can be any naturally occurring
                         amino acid except Lys or Arg
source                  1..511
                        mol_type = protein
                        organism = Vesicular stomatitis virus
SEQUENCE: 125
MTPAFILCML LAGSSWAKFT IVFPQSQKGD WKDVPPNYRY CPSSADQNWH GDLLGVNIRA     60
KMPXVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNXFPYE KGAAACRMKY    240
CTHEGIRLPS GVWFEMVDKE LLESVQMPEC PAGLTISAPT QTSVDVSLIL DVERMLDYSL    300
CQETWSKVHS GLPISPVDLG YIAPKNPGAG PAFTIVNGTL KYFDTRYLRI DIEGPVLKKM    360
TGKVSGTPTK XELWTEWFPY DDVEIGPNGV LKTPEGYKFP LYMIGHGLLD SDLQKTSQAE    420
VFHHPQIAEA VQKLPDDETL FFGDTGISKN PVEVIEGWFS NWRSSVMAIV FAILLLVITV    480
LMVRLCVAFR HFCCQKRHKI YNDLEMNQLR R                                  511

SEQ ID NO: 126          moltype = AA   length = 511
FEATURE                 Location/Qualifiers
SITE                    25
                        note = misc_feature - Xaa can be any naturally occurring
                         amino acid except Lys or Arg
SITE                    64
                        note = misc_feature - Xaa can be any naturally occurring
                         amino acid except Lys or Arg
SITE                    226
                        note = misc_feature - Xaa can be any naturally occurring
                         amino acid except Lys or Arg
SITE                    371
                        note = misc_feature - Xaa can be any naturally occurring
                         amino acid except Lys or Arg
source                  1..511
                        mol_type = protein
                        organism = Vesicular stomatitis virus
SEQUENCE: 126
MTPAFILCML LAGSSWAKFT IVFPXSQKGD WKDVPPNYRY CPSSADQNWH GDLLGVNIRA     60
KMPXVHKAIK ADGWMCHAAK WVTTCDYRWY GPQYITHSIH SFIPTKAQCE ESIKQTKEGV    120
WINPGFPPKN CGYASVSDAE SIIVQATAHS VMIDEYSGDW LDSQFPTGRC TGSTCETIHN    180
STLWYADYQV TGLCDSALVS TEVTFYSEDG LMTSIGRQNT GYRSNXFPYE KGAAACRMKY    240
CTHEGIRLPS GVWFEMVDKE LLESVQMPEC PAGLTISAPT QTSVDVSLIL DVERMLDYSL    300
```

```
CQETWSKVHS GLPISPVDLG YIAPKNPGAG PAFTIVNGTL KYFDTRYLRI DIEGPVLKKM   360
TGKVSGTPTK XELWTEWFPY DDVEIGPNGV LKTPEGYKFP LYMIGHGLLD SDLQKTSQAE   420
VPHHPQIAEA VQKLPDDETL FFGDTGISKN PVEVIEGWFS NWRSSVMAIV FAILLLVITV   480
LMVRLCVAFR HFCCQKRHKI YNDLEMNQLR R                                 511

SEQ ID NO: 127          moltype = AA  length = 495
FEATURE                 Location/Qualifiers
SITE                    8
                        note = misc_feature - Xaa can be any naturally occurring
                          amino acid except Lys or Arg
SITE                    47
                        note = misc_feature - Xaa can be any naturally occurring
                          amino acid except Lys or Arg
source                  1..495
                        mol_type = protein
                        organism = Vesicular stomatitis virus
SEQUENCE: 127
KFSIVFPXSQ KGNWKNVPSS YHYCPSSSDQ NWHNDLLGIT MKVKMPXTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTERELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 128          moltype = AA  length = 495
FEATURE                 Location/Qualifiers
SITE                    8
                        note = misc_feature - Xaa can be any naturally occurring
                          amino acid except Lys or Arg
SITE                    354
                        note = misc_feature - Xaa can be any naturally occurring
                          amino acid except Lys or Arg
source                  1..495
                        mol_type = protein
                        organism = Vesicular stomatitis virus
SEQUENCE: 128
KFSIVFPXSQ KGNWKNVPSS YHYCPSSSDQ NWHNDLLGIT MKVKMPKTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEXELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 129          moltype = AA  length = 495
FEATURE                 Location/Qualifiers
SITE                    8
                        note = misc_feature - Xaa can be any naturally occurring
                          amino acid except Lys or Arg
SITE                    47
                        note = misc_feature - Xaa can be any naturally occurring
                          amino acid except Lys or Arg
SITE                    354
                        note = misc_feature - Xaa can be any naturally occurring
                          amino acid except Lys or Arg
source                  1..495
                        mol_type = protein
                        organism = Vesicular stomatitis virus
SEQUENCE: 129
KFSIVFPXSQ KGNWKNVPSS YHYCPSSSDQ NWHNDLLGIT MKVKMPXTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEXELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 130          moltype = AA  length = 495
FEATURE                 Location/Qualifiers
SITE                    47
                        note = misc_feature - Xaa can be any naturally occurring
                          amino acid except Lys or Arg
```

```
SITE                    209
                        note = misc_feature - Xaa can be any naturally occurring
                         amino acid except Lys or Arg
source                  1..495
                        mol_type = protein
                        organism = Vesicular stomatitis virus
SEQUENCE: 130
KFSIVFPQSQ KGNWKNVPSS YHYCPSSSDQ NWHNDLLGIT MKVKMPXTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNXF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTERELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 131          moltype = AA  length = 495
FEATURE                 Location/Qualifiers
SITE                    209
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..495
                        mol_type = protein
                        organism = Vesicular stomatitis virus
SEQUENCE: 131
KFSIVFPQSQ KGNWKNVPSS YHYCPSSSDQ NWHNDLLGIT MKVKMPXTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNXF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEXELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 132          moltype = AA  length = 495
FEATURE                 Location/Qualifiers
SITE                    47
                        note = misc_feature - Xaa can be any naturally occurring
                         amino acid except Lys or Arg
SITE                    209
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..495
                        mol_type = protein
                        organism = Vesicular stomatitis virus
SEQUENCE: 132
KFSIVFPQSQ KGNWKNVPSS YHYCPSSSDQ NWHNDLLGIT MKVKMPXTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNXF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEXELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 133          moltype = AA  length = 495
FEATURE                 Location/Qualifiers
SITE                    8
                        note = misc_feature - Xaa can be any naturally occurring
                         amino acid except Lys or Arg
SITE                    47
                        note = misc_feature - Xaa can be any naturally occurring
                         amino acid except Lys or Arg
SITE                    209
                        note = misc_feature - Xaa can be any naturally occurring
                         amino acid except Lys or Arg
SITE                    354
                        note = misc_feature - Xaa can be any naturally occurring
                         amino acid except Lys or Arg
source                  1..495
```

```
                    mol_type = protein
                    organism = Vesicular stomatitis virus
SEQUENCE: 133
KFSIVFPXSQ KGNWKNVPSS YHYCPSSSDQ NWHNDLLGIT MKVKMPXTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNXF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEXELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                    495

SEQ ID NO: 134          moltype = AA  length = 512
FEATURE                 Location/Qualifiers
SITE                    25
                        note = misc_feature - Xaa can be any naturally occurring
                         amino acid except Lys or Arg
SITE                    64
                        note = misc_feature - Xaa can be any naturally occurring
                         amino acid except Lys or Arg
source                  1..512
                        mol_type = protein
                        organism = Vesicular stomatitis virus
SEQUENCE: 134
MNFLLLTFIV LPLCSHAKFS IVFPXSQKGN WKNVPSSYHY CPSSSDQNWH NDLLGITMKV    60
KMPXTHKAIQ ADGWMCHAAK WITTCDFRWY GPKYITHSIH SIQPTSEQCK ESIKQTKQGT   120
WMSPGFPPQN CGYATVTDSV AVVVQATPHH VLVDEYTGEW IDSQFPNGKC ETEECETVHN   180
STVWYSDYKV TGLCDATLVD TEITFFSEDG KKESIGKPNT GYRSNYFAYE KGDKVCKMNY   240
CKHAGVRLPS GVWFEFVDQD VYAAAKLPEC PVGATISAPT QTSVDVSLIL DVERILDYSL   300
CQETWSKIRS KQPVSPVDLS YLAPKNPGTG PAFTIINGTL KYFETRYIRI DIDNPIISKM   360
VGKISGSQTE RELWTEWFPY EGVEIGPNGI LKTPTGYKFP LFMIGHGMLD SDLHKTSQAE   420
VFEHPHLAEA PKQLPEEETL FFGDTGISKN PVELIEGWFS SWKSTVVTFF FAIGVFILLY   480
VVARIVIAVR YRYQGSNNKR IYNDIEMSRF RK                                 512

SEQ ID NO: 135          moltype = AA  length = 512
FEATURE                 Location/Qualifiers
SITE                    25
                        note = misc_feature - Xaa can be any naturally occurring
                         amino acid except Lys or Arg
SITE                    371
                        note = misc_feature - Xaa can be any naturally occurring
                         amino acid except Lys or Arg
source                  1..512
                        mol_type = protein
                        organism = Vesicular stomatitis virus
SEQUENCE: 135
MNFLLLTFIV LPLCSHAKFS IVFPXSQKGN WKNVPSSYHY CPSSSDQNWH NDLLGITMKV    60
KMPKTHKAIQ ADGWMCHAAK WITTCDFRWY GPKYITHSIH SIQPTSEQCK ESIKQTKQGT   120
WMSPGFPPQN CGYATVTDSV AVVVQATPHH VLVDEYTGEW IDSQFPNGKC ETEECETVHN   180
STVWYSDYKV TGLCDATLVD TEITFFSEDG KKESIGKPNT GYRSNYFAYE KGDKVCKMNY   240
CKHAGVRLPS GVWFEFVDQD VYAAAKLPEC PVGATISAPT QTSVDVSLIL DVERILDYSL   300
CQETWSKIRS KQPVSPVDLS YLAPKNPGTG PAFTIINGTL KYFETRYIRI DIDNPIISKM   360
VGKISGSQTE XELWTEWFPY EGVEIGPNGI LKTPTGYKFP LFMIGHGMLD SDLHKTSQAE   420
VFEHPHLAEA PKQLPEEETL FFGDTGISKN PVELIEGWFS SWKSTVVTFF FAIGVFILLY   480
VVARIVIAVR YRYQGSNNKR IYNDIEMSRF RK                                 512

SEQ ID NO: 136          moltype = AA  length = 512
FEATURE                 Location/Qualifiers
SITE                    25
                        note = misc_feature - Xaa can be any naturally occurring
                         amino acid except Lys or Arg
SITE                    64
                        note = misc_feature - Xaa can be any naturally occurring
                         amino acid except Lys or Arg
SITE                    371
                        note = misc_feature - Xaa can be any naturally occurring
                         amino acid except Lys or Arg
source                  1..512
                        mol_type = protein
                        organism = Vesicular stomatitis virus
SEQUENCE: 136
MNFLLLTFIV LPLCSHAKFS IVFPXSQKGN WKNVPSSYHY CPSSSDQNWH NDLLGITMKV    60
KMPXTHKAIQ ADGWMCHAAK WITTCDFRWY GPKYITHSIH SIQPTSEQCK ESIKQTKQGT   120
WMSPGFPPQN CGYATVTDSV AVVVQATPHH VLVDEYTGEW IDSQFPNGKC ETEECETVHN   180
STVWYSDYKV TGLCDATLVD TEITFFSEDG KKESIGKPNT GYRSNYFAYE KGDKVCKMNY   240
CKHAGVRLPS GVWFEFVDQD VYAAAKLPEC PVGATISAPT QTSVDVSLIL DVERILDYSL   300
CQETWSKIRS KQPVSPVDLS YLAPKNPGTG PAFTIINGTL KYFETRYIRI DIDNPIISKM   360
VGKISGSQTE XELWTEWFPY EGVEIGPNGI LKTPTGYKFP LFMIGHGMLD SDLHKTSQAE   420
```

```
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                 512

SEQ ID NO: 137          moltype = AA  length = 512
FEATURE                 Location/Qualifiers
SITE                    64
                        note = misc_feature - Xaa can be any naturally occurring
                          amino acid except Lys or Arg
SITE                    226
                        note = misc_feature - Xaa can be any naturally occurring
                          amino acid except Lys or Arg
source                  1..512
                        mol_type = protein
                        organism = Vesicular stomatitis virus
SEQUENCE: 137
MNFLLLTFIV LPLCSHAKFS IVFPQSQKGN WKNVPSSYHY CPSSSDQNWH NDLLGITMKV    60
KMPXTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
STVWYSDYKV TGLCDATLVD TEITFFSEDG KKESIGKPNT GYRSNXFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE RELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                 512

SEQ ID NO: 138          moltype = AA  length = 512
FEATURE                 Location/Qualifiers
SITE                    226
                        note = misc_feature - Xaa can be any naturally occurring
                          amino acid except Lys or Arg
SITE                    371
                        note = misc_feature - Xaa can be any naturally occurring
                          amino acid except Lys or Arg
source                  1..512
                        mol_type = protein
                        organism = Vesicular stomatitis virus
SEQUENCE: 138
MNFLLLTFIV LPLCSHAKFS IVFPQSQKGN WKNVPSSYHY CPSSSDQNWH NDLLGITMKV    60
KMPKTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
STVWYSDYKV TGLCDATLVD TEITFFSEDG KKESIGKPNT GYRSNXFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE XELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                 512

SEQ ID NO: 139          moltype = AA  length = 512
FEATURE                 Location/Qualifiers
SITE                    64
                        note = misc_feature - Xaa can be any naturally occurring
                          amino acid except Lys or Arg
SITE                    226
                        note = misc_feature - Xaa can be any naturally occurring
                          amino acid except Lys or Arg
SITE                    371
                        note = misc_feature - Xaa can be any naturally occurring
                          amino acid except Lys or Arg
source                  1..512
                        mol_type = protein
                        organism = Vesicular stomatitis virus
SEQUENCE: 139
MNFLLLTFIV LPLCSHAKFS IVFPQSQKGN WKNVPSSYHY CPSSSDQNWH NDLLGITMKV    60
KMPXTHKAIQ ADGWMCHAAK WITTCDFRWY GPKYITHSIH SIQPTSEQCK ESIKQTKQGT    120
WMSPGFPPQN CGYATVTDSV AVVVQATPHH VLVDEYTGEW IDSQFPNGKC ETEECETVHN    180
STVWYSDYKV TGLCDATLVD TEITFFSEDG KKESIGKPNT GYRSNXFAYE KGDKVCKMNY    240
CKHAGVRLPS GVWFEFVDQD VYAAAKLPEC PVGATISAPT QTSVDVSLIL DVERILDYSL    300
CQETWSKIRS KQPVSPVDLS YLAPKNPGTG PAFTIINGTL KYFETRYIRI DIDNPIISKM    360
VGKISGSQTE XELWTEWFPY EGVEIGPNGI LKTPTGYKFP LFMIGHGMLD SDLHKTSQAE    420
VFEHPHLAEA PKQLPEEETL FFGDTGISKN PVELIEGWFS SWKSTVVTFF FAIGVFILLY    480
VVARIVIAVR YRYQGSNNKR IYNDIEMSRF RK                                 512

SEQ ID NO: 140          moltype = AA  length = 512
FEATURE                 Location/Qualifiers
SITE                    25
                        note = misc_feature - Xaa can be any naturally occurring
                          amino acid except Lys or Arg
SITE                    64
                        note = misc_feature - Xaa can be any naturally occurring
```

```
                         amino acid except Lys or Arg
SITE                226
                    note = misc_feature - Xaa can be any naturally occurring
                         amino acid except Lys or Arg
SITE                371
                    note = misc_feature - Xaa can be any naturally occurring
                         amino acid except Lys or Arg
source              1..512
                    mol_type = protein
                    organism = Vesicular stomatitis virus
SEQUENCE: 140
MNFLLLTFIV LPLCSHAKFS IVFPXSQKGN WKNVPSSYHY CPSSSDQNWH NDLLGITMKV    60
KMPXTHKAIQ ADGWMCHAAK WITTCDFRWY GPKYITHSIH SIQPTSEQCK ESIKQTKQGT   120
WMSPGFPPQN CGYATVTDSV AVVVQATPHH VLVDEYTGEW IDSQFPNGKC ETEECETVHN   180
STVWYSDYKV TGLCDATLVD TEITFFSEDG KKESIGKPNT GYRSNXFAYE KGDKVCKMNY   240
CKHAGVRLPS GVWFEFVDQD VYAAAKLPEC PVGATISAPT QTSVDVSLIL DVERILDYSL   300
CQETWSKIRS KQPVSPVDLS YLAPKNPGTG PAFTIINGTL KYFETRYIRI DIDNPIISKM   360
VGKISGSQTE XELWTEWFPY EGVEIGPNGI LKTPTGYKFP LFMIGHGMLD SDLHKTSQAE   420
VFEHPHLAEA PKQLPEEETL FFGDTGISKN PVELIEGWFS SWKSTVVTFF FAIGVFILLY   480
VVARIVIAVR YRYQGSNNKR IYNDIEMSRF RK                                 512

SEQ ID NO: 141      moltype = AA   length = 496
FEATURE             Location/Qualifiers
SITE                8
                    note = misc_feature - Xaa can be any naturally occurring
                         amino acid except Lys or Arg
SITE                47
                    note = misc_feature - Xaa can be any naturally occurring
                         amino acid except Lys or Arg
source              1..496
                    mol_type = protein
                    organism = Vesicular stomatitis virus
SEQUENCE: 141
KFTIVFPXNQ KGNWKNVPAN YQYCPSSSDL NWHNGLIGTS LQVKMPXSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 142      moltype = AA   length = 496
FEATURE             Location/Qualifiers
SITE                8
                    note = misc_feature - Xaa can be any naturally occurring
                         amino acid except Lys or Arg
SITE                354
                    note = misc_feature - Xaa can be any naturally occurring
                         amino acid except Lys or Arg
source              1..496
                    mol_type = protein
                    organism = Vesicular stomatitis virus
SEQUENCE: 142
KFTIVFPXNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEXELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 143      moltype = AA   length = 496
FEATURE             Location/Qualifiers
SITE                8
                    note = misc_feature - Xaa can be any naturally occurring
                         amino acid except Lys or Arg
SITE                47
                    note = misc_feature - Xaa can be any naturally occurring
                         amino acid except Lys or Arg
SITE                354
                    note = misc_feature - Xaa can be any naturally occurring
                         amino acid except Lys or Arg
source              1..496
                    mol_type = protein
                    organism = Vesicular stomatitis virus
```

-continued

```
SEQUENCE: 143
KFTIVFPXNQ KGNWKNVPAN YQYCPSSSDL NWHNGLIGTS LQVKMPXSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGKACR  MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEXELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 144            moltype = AA  length = 496
FEATURE                   Location/Qualifiers
SITE                      47
                          note = misc_feature - Xaa can be any naturally occurring
                           amino acid except Lys or Arg
SITE                      209
                          note = misc_feature - Xaa can be any naturally occurring
                           amino acid except Lys or Arg
source                    1..496
                          mol_type = protein
                          organism = Vesicular stomatitis virus
SEQUENCE: 144
KFTIVFPHNQ KGNWKNVPAN YQYCPSSSDL NWHNGLIGTS LQVKMPXSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNXF AYENGKACR  MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 145            moltype = AA  length = 496
FEATURE                   Location/Qualifiers
SITE                      209
                          note = misc_feature - Xaa can be any naturally occurring
                           amino acid except Lys or Arg
SITE                      354
                          note = misc_feature - Xaa can be any naturally occurring
                           amino acid except Lys or Arg
source                    1..496
                          mol_type = protein
                          organism = Vesicular stomatitis virus
SEQUENCE: 145
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNXF AYENGKACR  MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEXELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 146            moltype = AA  length = 496
FEATURE                   Location/Qualifiers
SITE                      47
                          note = misc_feature - Xaa can be any naturally occurring
                           amino acid except Lys or Arg
SITE                      209
                          note = misc_feature - Xaa can be any naturally occurring
                           amino acid except Lys or Arg
SITE                      354
                          note = misc_feature - Xaa can be any naturally occurring
                           amino acid except Lys or Arg
source                    1..496
                          mol_type = protein
                          organism = Vesicular stomatitis virus
SEQUENCE: 146
KFTIVFPHNQ KGNWKNVPAN YQYCPSSSDL NWHNGLIGTS LQVKMPXSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNXF AYENGKACR  MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEXELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496
```

```
SEQ ID NO: 147         moltype = AA  length = 496
FEATURE                Location/Qualifiers
SITE                   8
                       note = misc_feature - Xaa can be any naturally occurring
                        amino acid except Lys or Arg
SITE                   47
                       note = misc_feature - Xaa can be any naturally occurring
                        amino acid except Lys or Arg
SITE                   209
                       note = misc_feature - Xaa can be any naturally occurring
                        amino acid except Lys or Arg
SITE                   354
                       note = misc_feature - Xaa can be any naturally occurring
                        amino acid except Lys or Arg
source                 1..496
                       mol_type = protein
                       organism = Vesicular stomatitis virus
SEQUENCE: 147
KFTIVFPXNQ KGNWKNVPAN YQYCPSSSDL NWHNGLIGTS LQVKMPXSHK AIQADGWMCH     60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNXF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEXELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 148         moltype = AA  length = 513
FEATURE                Location/Qualifiers
SITE                   25
                       note = misc_feature - Xaa can be any naturally occurring
                        amino acid except Lys or Arg
SITE                   64
                       note = misc_feature - Xaa can be any naturally occurring
                        amino acid except Lys or Arg
source                 1..513
                       mol_type = protein
                       organism = Vesicular stomatitis virus
SEQUENCE: 148
MLVLYLLLSL LALGAQCKFT IVFPXNQKGN WKNVPANYQY CPSSSDLNWH NGLIGTSLQV     60
KMPXSHKAIQ ADGWMCHAAK WVTTCDFRWY GPKYVTHSIK SMIPTVDQCK ESIAQTKQGT    120
WLNPGFPPQS CGYASVTDAE AVIVKATPHQ VLVDEYTGEW VDSQFPTGKC NKDICPTVHN    180
STTWHSDYKV TGLCDANLIS MDITFFSEDG KLTSLGKEGT GFRSNYFAYE NGDKACRMQY    240
CKHWGVRLPS GVWFEMADKD IYNDAKFPDC PEGSSIAAPS QTSVDVSLIQ DVERILDYSL    300
CQETWSKIRA HLPISPVDLS YLSPKNPGTG PAFTIINGTL KYFETRYIRV DIAGPIIPQM    360
RGVISGTTTE RELWTDWYPY EDVEIGPNGV LKTATGYKFP LYMIGHGMLD SDLHISSKAQ    420
VFEHPHIQDA ASQLPDDETL FFGDTGLSKN PIELVEGWFS GWKSTIASFF FIIGLVIGLY    480
LVLRIGIALC IKCRVQEKRP KIYTDVEMNR LDR                                 513

SEQ ID NO: 149         moltype = AA  length = 513
FEATURE                Location/Qualifiers
SITE                   25
                       note = misc_feature - Xaa can be any naturally occurring
                        amino acid except Lys or Arg
SITE                   371
                       note = misc_feature - Xaa can be any naturally occurring
                        amino acid except Lys or Arg
source                 1..513
                       mol_type = protein
                       organism = Vesicular stomatitis virus
SEQUENCE: 149
MLVLYLLLSL LALGAQCKFT IVFPXNQKGN WKNVPANYQY CPSSSDLNWH NGLIGTSLQV     60
KMPKSHKAIQ ADGWMCHAAK WVTTCDFRWY GPKYVTHSIK SMIPTVDQCK ESIAQTKQGT    120
WLNPGFPPQS CGYASVTDAE AVIVKATPHQ VLVDEYTGEW VDSQFPTGKC NKDICPTVHN    180
STTWHSDYKV TGLCDANLIS MDITFFSEDG KLTSLGKEGT GFRSNYFAYE NGDKACRMQY    240
CKHWGVRLPS GVWFEMADKD IYNDAKFPDC PEGSSIAAPS QTSVDVSLIQ DVERILDYSL    300
CQETWSKIRA HLPISPVDLS YLSPKNPGTG PAFTIINGTL KYFETRYIRV DIAGPIIPQM    360
RGVISGTTTE XELWTDWYPY EDVEIGPNGV LKTATGYKFP LYMIGHGMLD SDLHISSKAQ    420
VFEHPHIQDA ASQLPDDETL FFGDTGLSKN PIELVEGWFS GWKSTIASFF FIIGLVIGLY    480
LVLRIGIALC IKCRVQEKRP KIYTDVEMNR LDR                                 513

SEQ ID NO: 150         moltype = AA  length = 513
FEATURE                Location/Qualifiers
SITE                   25
                       note = misc_feature - Xaa can be any naturally occurring
                        amino acid except Lys or Arg
SITE                   64
```

-continued

```
                           note = misc_feature - Xaa can be any naturally occurring
                              amino acid except Lys or Arg
SITE                       371
                           note = misc_feature - Xaa can be any naturally occurring
                              amino acid except Lys or Arg
source                     1..513
                           mol_type = protein
                           organism = Vesicular stomatitis virus
SEQUENCE: 150
MLVLYLLLSL LALGAQCKFT IVFPXNQKGN WKNVPANYQY CPSSSDLNWH NGLIGTSLQV    60
KMPXSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNYFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE XELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 151             moltype = AA  length = 513
FEATURE                    Location/Qualifiers
SITE                       64
                           note = misc_feature - Xaa can be any naturally occurring
                              amino acid except Lys or Arg
SITE                       226
                           note = misc_feature - Xaa can be any naturally occurring
                              amino acid except Lys or Arg
source                     1..513
                           mol_type = protein
                           organism = Vesicular stomatitis virus
SEQUENCE: 151
MLVLYLLLSL LALGAQCKFT IVFPHNQKGN WKNVPANYQY CPSSSDLNWH NGLIGTSLQV    60
KMPXSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNXFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE RELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 152             moltype = AA  length = 513
FEATURE                    Location/Qualifiers
SITE                       226
                           note = misc_feature - Xaa can be any naturally occurring
                              amino acid except Lys or Arg
SITE                       371
                           note = misc_feature - Xaa can be any naturally occurring
                              amino acid except Lys or Arg
source                     1..513
                           mol_type = protein
                           organism = Vesicular stomatitis virus
SEQUENCE: 152
MLVLYLLLSL LALGAQCKFT IVFPHNQKGN WKNVPANYQY CPSSSDLNWH NGLIGTSLQV    60
KMPKSHKAIQ ADGWMCHAAK WVTTCDFRWY GPKYVTHSIK SMIPTVDQCK ESIAQTKQGT   120
WLNPGFPPQS CGYASVTDAE AVIVKATPHQ VLVDEYTGEW VDSQFPTGKC NKDICPTVHN   180
STTWHSDYKV TGLCDANLIS MDITFFSEDG KLTSLGKEGT GFRSNXFAYE NGDKACRMQY   240
CKHWGVRLPS GVWFEMADKD IYNDAKFPDC PEGSSIAAPS QTSVDVSLIQ DVERILDYSL   300
CQETWSKIRA HLPISPVDLS YLSPKNPGTG PAFTIINGTL KYFETRYIRV DIAGPIIPQM   360
RGVISGTTTE XELWTDWYPY EDVEIGPNGV LKTATGYKFP LYMIGHGMLD SDLHISSKAQ   420
VFEHPHIQDA ASQLPDDETL FFGDTGLSKN PIELVEGWFS GWKSTIASFF FIIGLVIGLY   480
LVLRIGIALC IKCRVQEKRP KIYTDVEMNR LDR                                513

SEQ ID NO: 153             moltype = AA  length = 513
FEATURE                    Location/Qualifiers
SITE                       64
                           note = misc_feature - Xaa can be any naturally occurring
                              amino acid except Lys or Arg
SITE                       226
                           note = misc_feature - Xaa can be any naturally occurring
                              amino acid except Lys or Arg
SITE                       371
                           note = misc_feature - Xaa can be any naturally occurring
                              amino acid except Lys or Arg
source                     1..513
                           mol_type = protein
                           organism = Vesicular stomatitis virus
SEQUENCE: 153
MLVLYLLLSL LALGAQCKFT IVFPHNQKGN WKNVPANYQY CPSSSDLNWH NGLIGTSLQV    60
```

```
KMPXSHKAIQ ADGWMCHAAK WVTTCDFRWY GPKYVTHSIK SMIPTVDQCK ESIAQTKQGT    120
WLNPGFPPQS CGYASVTDAE AVIVKATPHQ VLVDEYTGEW VDSQFPTGKC NKDICPTVHN    180
STTWHSDYKV TGLCDANLIS MDITFFSEDG KLTSLGKEGT GFRSNXFAYE NGDKACRMQY    240
CKHWGVRLPS GVWFEMADKD IYNDAKFPDC PEGSSIAAPS QTSVDVSLIQ DVERILDYSL    300
CQETWSKIRA HLPISPVDLS YLSPKNPGTG PAFTIINGTL KYFETRYIRV DIAGPIIPQM    360
RGVISGTTTE XELWTDWYPY EDVEIGPNGV LKTATGYKFP LYMIGHGMLD SDLHISSKAQ    420
VFEHPHIQDA ASQLPDDETL FFGDTGLSKN PIELVEGWFS GWKSTIASFF FIIGLVIGLY    480
LVLRIGIALC IKCRVQEKRP KIYTDVEMNR LDR                                 513

SEQ ID NO: 154          moltype = AA   length = 513
FEATURE                 Location/Qualifiers
SITE                    25
                        note = misc_feature - Xaa can be any naturally occurring
                         amino acid except Lys or Arg
SITE                    64
                        note = misc_feature - Xaa can be any naturally occurring
                         amino acid except Lys or Arg
SITE                    226
                        note = misc_feature - Xaa can be any naturally occurring
                         amino acid except Lys or Arg
SITE                    371
                        note = misc_feature - Xaa can be any naturally occurring
                         amino acid except Lys or Arg
source                  1..513
                        mol_type = protein
                        organism = Vesicular stomatitis virus
SEQUENCE: 154
MLVLYLLLSL LALGAQCKFT IVFPXNQKGN WKNVPANYQY CPSSSDLNWH NGLIGTSLQV     60
KMPXSHKAIQ ADGWMCHAAK WVTTCDFRWY GPKYVTHSIK SMIPTVDQCK ESIAQTKQGT    120
WLNPGFPPQS CGYASVTDAE AVIVKATPHQ VLVDEYTGEW VDSQFPTGKC NKDICPTVHN    180
STTWHSDYKV TGLCDANLIS MDITFFSEDG KLTSLGKEGT GFRSNXFAYE NGDKACRMQY    240
CKHWGVRLPS GVWFEMADKD IYNDAKFPDC PEGSSIAAPS QTSVDVSLIQ DVERILDYSL    300
CQETWSKIRA HLPISPVDLS YLSPKNPGTG PAFTIINGTL KYFETRYIRV DIAGPIIPQM    360
RGVISGTTTE XELWTDWYPY EDVEIGPNGV LKTATGYKFP LYMIGHGMLD SDLHISSKAQ    420
VFEHPHIQDA ASQLPDDETL FFGDTGLSKN PIELVEGWFS GWKSTIASFF FIIGLVIGLY    480
LVLRIGIALC IKCRVQEKRP KIYTDVEMNR LDR                                 513

SEQ ID NO: 155          moltype = AA   length = 495
FEATURE                 Location/Qualifiers
source                  1..495
                        mol_type = protein
                        organism = Vesicular stomatitis virus
SEQUENCE: 155
KFTIVFPHNQ KGNWKNVPSN YHYCPSSSDL NWHNDLIGTA IQVKMPASHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTERELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 156          moltype = AA   length = 495
FEATURE                 Location/Qualifiers
source                  1..495
                        mol_type = protein
                        organism = Vesicular stomatitis virus
SEQUENCE: 156
KFTIVFPHNQ KGNWKNVPSN YHYCPSSSDL NWHNDLIGTA IQVKMPGSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTERELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 157          moltype = AA   length = 495
FEATURE                 Location/Qualifiers
source                  1..495
                        mol_type = protein
                        organism = Vesicular stomatitis virus
SEQUENCE: 157
KFTIVFPHNQ KGNWKNVPSN YHYCPSSSDL NWHNDLIGTA IQVKMPFSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
```

```
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTERELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 158           moltype = AA   length = 495
FEATURE                  Location/Qualifiers
source                   1..495
                         mol_type = protein
                         organism = Vesicular stomatitis virus
SEQUENCE: 158
KFTIVFPHNQ KGNWKNVPSN YHYCPSSSDL NWHNDLIGTA IQVKMPQSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTERELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 159           moltype = AA   length = 495
FEATURE                  Location/Qualifiers
source                   1..495
                         mol_type = protein
                         organism = Vesicular stomatitis virus
SEQUENCE: 159
KFTIVFPHNQ KGNWKNVPSN YHYCPSSSDL NWHNDLIGTA IQVKMPKSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEAELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 160           moltype = AA   length = 495
FEATURE                  Location/Qualifiers
source                   1..495
                         mol_type = protein
                         organism = Vesicular stomatitis virus
SEQUENCE: 160
KFTIVFPHNQ KGNWKNVPSN YHYCPSSSDL NWHNDLIGTA IQVKMPKSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEGELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 161           moltype = AA   length = 495
FEATURE                  Location/Qualifiers
source                   1..495
                         mol_type = protein
                         organism = Vesicular stomatitis virus
SEQUENCE: 161
KFTIVFPHNQ KGNWKNVPSN YHYCPSSSDL NWHNDLIGTA IQVKMPKSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEFELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 162           moltype = AA   length = 495
FEATURE                  Location/Qualifiers
source                   1..495
                         mol_type = protein
                         organism = Vesicular stomatitis virus
SEQUENCE: 162
KFTIVFPHNQ KGNWKNVPSN YHYCPSSSDL NWHNDLIGTA IQVKMPKSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
```

```
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEQELWDDW    360
APYEDVEIGN NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 163         moltype = AA  length = 495
FEATURE                Location/Qualifiers
source                 1..495
                       mol_type = protein
                       organism = Vesicular stomatitis virus
SEQUENCE: 163
KFTIVFPHNQ KGNWKNVPSN YHYCPSSSDL NWHNDLIGTA IQVKMPASHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEAELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 164         moltype = AA  length = 495
FEATURE                Location/Qualifiers
source                 1..495
                       mol_type = protein
                       organism = Vesicular stomatitis virus
SEQUENCE: 164
KFTIVFPHNQ KGNWKNVPSN YHYCPSSSDL NWHNDLIGTA IQVKMPASHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEGELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 165         moltype = AA  length = 495
FEATURE                Location/Qualifiers
source                 1..495
                       mol_type = protein
                       organism = Vesicular stomatitis virus
SEQUENCE: 165
KFTIVFPHNQ KGNWKNVPSN YHYCPSSSDL NWHNDLIGTA IQVKMPASHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEFELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 166         moltype = AA  length = 495
FEATURE                Location/Qualifiers
source                 1..495
                       mol_type = protein
                       organism = Vesicular stomatitis virus
SEQUENCE: 166
KFTIVFPHNQ KGNWKNVPSN YHYCPSSSDL NWHNDLIGTA IQVKMPASHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEQELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 167         moltype = AA  length = 495
FEATURE                Location/Qualifiers
source                 1..495
                       mol_type = protein
                       organism = Vesicular stomatitis virus
SEQUENCE: 167
KFTIVFPHNQ KGNWKNVPSN YHYCPSSSDL NWHNDLIGTA IQVKMPGSHK AIQADGWMCH     60
ASKWVTTCDF RWYGPKYITQ SIRSFTPSVE QCKESIEQTK QGTWLNPGFP PQSCGYATVT    120
```

```
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEAELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 168           moltype = AA  length = 495
FEATURE                  Location/Qualifiers
source                   1..495
                         mol_type = protein
                         organism = Vesicular stomatitis virus
SEQUENCE: 168
KFTIVFPHNQ KGNWKNVPSN YHYCPSSSDL NWHNDLIGTA IQVKMPGSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEGELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 169           moltype = AA  length = 495
FEATURE                  Location/Qualifiers
source                   1..495
                         mol_type = protein
                         organism = Vesicular stomatitis virus
SEQUENCE: 169
KFTIVFPHNQ KGNWKNVPSN YHYCPSSSDL NWHNDLIGTA IQVKMPGSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEFELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 170           moltype = AA  length = 495
FEATURE                  Location/Qualifiers
source                   1..495
                         mol_type = protein
                         organism = Vesicular stomatitis virus
SEQUENCE: 170
KFTIVFPHNQ KGNWKNVPSN YHYCPSSSDL NWHNDLIGTA IQVKMPGSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEQELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 171           moltype = AA  length = 495
FEATURE                  Location/Qualifiers
source                   1..495
                         mol_type = protein
                         organism = Vesicular stomatitis virus
SEQUENCE: 171
KFTIVFPHNQ KGNWKNVPSN YHYCPSSSDL NWHNDLIGTA IQVKMPFSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEAELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 172           moltype = AA  length = 495
FEATURE                  Location/Qualifiers
source                   1..495
                         mol_type = protein
                         organism = Vesicular stomatitis virus
SEQUENCE: 172
KFTIVFPHNQ KGNWKNVPSN YHYCPSSSDL NWHNDLIGTA IQVKMPFSHK AIQADGWMCH     60
```

```
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEGELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 173           moltype = AA   length = 495
FEATURE                  Location/Qualifiers
source                   1..495
                         mol_type = protein
                         organism = Vesicular stomatitis virus
SEQUENCE: 173
KFTIVFPHNQ KGNWKNVPSN YHYCPSSSDL NWHNDLIGTA IQVKMPFSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEFELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 174           moltype = AA   length = 495
FEATURE                  Location/Qualifiers
source                   1..495
                         mol_type = protein
                         organism = Vesicular stomatitis virus
SEQUENCE: 174
KFTIVFPHNQ KGNWKNVPSN YHYCPSSSDL NWHNDLIGTA IQVKMPFSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEQELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 175           moltype = AA   length = 495
FEATURE                  Location/Qualifiers
source                   1..495
                         mol_type = protein
                         organism = Vesicular stomatitis virus
SEQUENCE: 175
KFTIVFPHNQ KGNWKNVPSN YHYCPSSSDL NWHNDLIGTA IQVKMPQSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEAELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 176           moltype = AA   length = 495
FEATURE                  Location/Qualifiers
source                   1..495
                         mol_type = protein
                         organism = Vesicular stomatitis virus
SEQUENCE: 176
KFTIVFPHNQ KGNWKNVPSN YHYCPSSSDL NWHNDLIGTA IQVKMPQSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEGELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                    495

SEQ ID NO: 177           moltype = AA   length = 495
FEATURE                  Location/Qualifiers
source                   1..495
                         mol_type = protein
                         organism = Vesicular stomatitis virus
SEQUENCE: 177
```

```
KFTIVFPHNQ KGNWKNVPSN YHYCPSSSDL NWHNDLIGTA IQVKMPQSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEFELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 178          moltype = AA   length = 495
FEATURE                 Location/Qualifiers
source                  1..495
                        mol_type = protein
                        organism = Vesicular stomatitis virus
SEQUENCE: 178
KFTIVFPHNQ KGNWKNVPSN YHYCPSSSDL NWHNDLIGTA IQVKMPQSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTEQELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 179          moltype = AA   length = 496
FEATURE                 Location/Qualifiers
source                  1..496
                        mol_type = protein
                        organism = Vesicular stomatitis virus
SEQUENCE: 179
KFTIVFPHHQ KGNWKNVPST YHYCPSSSDQ NWHNDLTGVS LHVKIPASHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 180          moltype = AA   length = 496
FEATURE                 Location/Qualifiers
source                  1..496
                        mol_type = protein
                        organism = Vesicular stomatitis virus
SEQUENCE: 180
KFTIVFPHHQ KGNWKNVPST YHYCPSSSDQ NWHNDLTGVS LHVKIPGSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 181          moltype = AA   length = 496
FEATURE                 Location/Qualifiers
source                  1..496
                        mol_type = protein
                        organism = Vesicular stomatitis virus
SEQUENCE: 181
KFTIVFPHHQ KGNWKNVPST YHYCPSSSDQ NWHNDLTGVS LHVKIPFSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 182          moltype = AA   length = 496
FEATURE                 Location/Qualifiers
source                  1..496
                        mol_type = protein
                        organism = Vesicular stomatitis virus
```

```
SEQUENCE: 182
KFTIVFPHHQ KGNWKNVPST YHYCPSSSDQ NWHNDLTGVS LHVKIPQSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTERELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 183         moltype = AA  length = 496
FEATURE                Location/Qualifiers
source                 1..496
                       mol_type = protein
                       organism = Vesicular stomatitis virus
SEQUENCE: 183
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEAELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 184         moltype = AA  length = 496
FEATURE                Location/Qualifiers
source                 1..496
                       mol_type = protein
                       organism = Vesicular stomatitis virus
SEQUENCE: 184
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEGELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 185         moltype = AA  length = 496
FEATURE                Location/Qualifiers
source                 1..496
                       mol_type = protein
                       organism = Vesicular stomatitis virus
SEQUENCE: 185
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEFELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 186         moltype = AA  length = 496
FEATURE                Location/Qualifiers
source                 1..496
                       mol_type = protein
                       organism = Vesicular stomatitis virus
SEQUENCE: 186
KFTIVFPHHQ KGNWKNVPST YHYCPSSSDQ NWHNDLTGVS LHVKIPKSHK AIQADGWMCH    60
AAKWVTTCDF RWYGPKYITH SIHSMSPTLE QCKTSIEQTK QGVWINPGFP PQSCGYATVT   120
DAEVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEQELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 187         moltype = AA  length = 496
FEATURE                Location/Qualifiers
source                 1..496
                       mol_type = protein
```

```
                        organism = Vesicular stomatitis virus
SEQUENCE: 187
KFTIVFPHHQ KGNWKNVPST YHYCPSSSDQ NWHNDLTGVS LHVKIPASHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEAELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 188         moltype = AA length = 496
FEATURE                Location/Qualifiers
source                 1..496
                       mol_type = protein
                       organism = Vesicular stomatitis virus
SEQUENCE: 188
KFTIVFPHHQ KGNWKNVPST YHYCPSSSDQ NWHNDLTGVS LHVKIPASHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEGELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 189         moltype = AA length = 496
FEATURE                Location/Qualifiers
source                 1..496
                       mol_type = protein
                       organism = Vesicular stomatitis virus
SEQUENCE: 189
KFTIVFPHHQ KGNWKNVPST YHYCPSSSDQ NWHNDLTGVS LHVKIPASHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEFELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 190         moltype = AA length = 496
FEATURE                Location/Qualifiers
source                 1..496
                       mol_type = protein
                       organism = Vesicular stomatitis virus
SEQUENCE: 190
KFTIVFPHHQ KGNWKNVPST YHYCPSSSDQ NWHNDLTGVS LHVKIPASHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEQELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 191         moltype = AA length = 496
FEATURE                Location/Qualifiers
source                 1..496
                       mol_type = protein
                       organism = Vesicular stomatitis virus
SEQUENCE: 191
KFTIVFPHHQ KGNWKNVPST YHYCPSSSDQ NWHNDLTGVS LHVKIPGSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEAELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                  496

SEQ ID NO: 192         moltype = AA length = 496
FEATURE                Location/Qualifiers
source                 1..496
```

```
                        mol_type = protein
                        organism = Vesicular stomatitis virus
SEQUENCE: 192
KFTIVFPHHQ KGNWKNVPST YHYCPSSSDQ NWHNDLTGVS LHVKIPGSHK AIQADGWMCH      60
AAKWVTTCDF RWYGPKYITH SIHSMSPTLE QCKTSIEQTK QGVWINPGFP PQSCGYATVT     120
DAEVVVVQAT PHHVLVDEYT GEWIDSQLVG GKCSKEVCQT VHNSTVWHAD YKITGLCESN     180
LASVDITFFS EDGQKTSLGK PNTGFRSNHF AYESGEKACR MQYCTQWGIR LPSGVWFELV     240
DKDLFQAAKL PECPRGSSIS APSQTSVDVS LIQDVERILD YSLCQETWSK IRAKLPVSPV     300
DLSYLAPKNP GSGPAFTIIN GTLKYFETRY IRVDISNPII PHMVGTMSGT TTEGELWNDW     360
YPYEDVEIGP NGVLKTPTGF KFPLYMIGHG MLDSDLHKSS QAQVFEHPHA KDAASQLPDD     420
ETLFFGDTGL SKNPVELVEG WFSSWKSTLA SFFLIIGLGV ALIFIIRIIV AIRYKYKGRK     480
TQKIYNDVEM SRLGNK                                                     496

SEQ ID NO: 193          moltype = AA  length = 496
FEATURE                 Location/Qualifiers
source                  1..496
                        mol_type = protein
                        organism = Vesicular stomatitis virus
SEQUENCE: 193
KFTIVFPHHQ KGNWKNVPST YHYCPSSSDQ NWHNDLTGVS LHVKIPGSHK AIQADGWMCH      60
AAKWVTTCDF RWYGPKYITH SIHSMSPTLE QCKTSIEQTK QGVWINPGFP PQSCGYATVT     120
DAEVVVVQAT PHHVLVDEYT GEWIDSQLVG GKCSKEVCQT VHNSTVWHAD YKITGLCESN     180
LASVDITFFS EDGQKTSLGK PNTGFRSNHF AYESGEKACR MQYCTQWGIR LPSGVWFELV     240
DKDLFQAAKL PECPRGSSIS APSQTSVDVS LIQDVERILD YSLCQETWSK IRAKLPVSPV     300
DLSYLAPKNP GSGPAFTIIN GTLKYFETRY IRVDISNPII PHMVGTMSGT TTEFELWNDW     360
YPYEDVEIGP NGVLKTPTGF KFPLYMIGHG MLDSDLHKSS QAQVFEHPHA KDAASQLPDD     420
ETLFFGDTGL SKNPVELVEG WFSSWKSTLA SFFLIIGLGV ALIFIIRIIV AIRYKYKGRK     480
TQKIYNDVEM SRLGNK                                                     496

SEQ ID NO: 194          moltype = AA  length = 496
FEATURE                 Location/Qualifiers
source                  1..496
                        mol_type = protein
                        organism = Vesicular stomatitis virus
SEQUENCE: 194
KFTIVFPHHQ KGNWKNVPST YHYCPSSSDQ NWHNDLTGVS LHVKIPGSHK AIQADGWMCH      60
AAKWVTTCDF RWYGPKYITH SIHSMSPTLE QCKTSIEQTK QGVWINPGFP PQSCGYATVT     120
DAEVVVVQAT PHHVLVDEYT GEWIDSQLVG GKCSKEVCQT VHNSTVWHAD YKITGLCESN     180
LASVDITFFS EDGQKTSLGK PNTGFRSNHF AYESGEKACR MQYCTQWGIR LPSGVWFELV     240
DKDLFQAAKL PECPRGSSIS APSQTSVDVS LIQDVERILD YSLCQETWSK IRAKLPVSPV     300
DLSYLAPKNP GSGPAFTIIN GTLKYFETRY IRVDISNPII PHMVGTMSGT TTEQELWNDW     360
YPYEDVEIGP NGVLKTPTGF KFPLYMIGHG MLDSDLHKSS QAQVFEHPHA KDAASQLPDD     420
ETLFFGDTGL SKNPVELVEG WFSSWKSTLA SFFLIIGLGV ALIFIIRIIV AIRYKYKGRK     480
TQKIYNDVEM SRLGNK                                                     496

SEQ ID NO: 195          moltype = AA  length = 496
FEATURE                 Location/Qualifiers
source                  1..496
                        mol_type = protein
                        organism = Vesicular stomatitis virus
SEQUENCE: 195
KFTIVFPHHQ KGNWKNVPST YHYCPSSSDQ NWHNDLTGVS LHVKIPFSHK AIQADGWMCH      60
AAKWVTTCDF RWYGPKYITH SIHSMSPTLE QCKTSIEQTK QGVWINPGFP PQSCGYATVT     120
DAEVVVVQAT PHHVLVDEYT GEWIDSQLVG GKCSKEVCQT VHNSTVWHAD YKITGLCESN     180
LASVDITFFS EDGQKTSLGK PNTGFRSNHF AYESGEKACR MQYCTQWGIR LPSGVWFELV     240
DKDLFQAAKL PECPRGSSIS APSQTSVDVS LIQDVERILD YSLCQETWSK IRAKLPVSPV     300
DLSYLAPKNP GSGPAFTIIN GTLKYFETRY IRVDISNPII PHMVGTMSGT TTEAELWNDW     360
YPYEDVEIGP NGVLKTPTGF KFPLYMIGHG MLDSDLHKSS QAQVFEHPHA KDAASQLPDD     420
ETLFFGDTGL SKNPVELVEG WFSSWKSTLA SFFLIIGLGV ALIFIIRIIV AIRYKYKGRK     480
TQKIYNDVEM SRLGNK                                                     496

SEQ ID NO: 196          moltype = AA  length = 496
FEATURE                 Location/Qualifiers
source                  1..496
                        mol_type = protein
                        organism = Vesicular stomatitis virus
SEQUENCE: 196
KFTIVFPHHQ KGNWKNVPST YHYCPSSSDQ NWHNDLTGVS LHVKIPFSHK AIQADGWMCH      60
AAKWVTTCDF RWYGPKYITH SIHSMSPTLE QCKTSIEQTK QGVWINPGFP PQSCGYATVT     120
DAEVVVVQAT PHHVLVDEYT GEWIDSQLVG GKCSKEVCQT VHNSTVWHAD YKITGLCESN     180
LASVDITFFS EDGQKTSLGK PNTGFRSNHF AYESGEKACR MQYCTQWGIR LPSGVWFELV     240
DKDLFQAAKL PECPRGSSIS APSQTSVDVS LIQDVERILD YSLCQETWSK IRAKLPVSPV     300
DLSYLAPKNP GSGPAFTIIN GTLKYFETRY IRVDISNPII PHMVGTMSGT TTEGELWNDW     360
YPYEDVEIGP NGVLKTPTGF KFPLYMIGHG MLDSDLHKSS QAQVFEHPHA KDAASQLPDD     420
ETLFFGDTGL SKNPVELVEG WFSSWKSTLA SFFLIIGLGV ALIFIIRIIV AIRYKYKGRK     480
TQKIYNDVEM SRLGNK                                                     496

SEQ ID NO: 197          moltype = AA  length = 496
FEATURE                 Location/Qualifiers
```

```
source                    1..496
                          mol_type = protein
                          organism = Vesicular stomatitis virus
SEQUENCE: 197
KFTIVFPHHQ KGNWKNVPST YHYCPSSSDQ NWHNDLTGVS LHVKIPFSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEFELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 198           moltype = AA  length = 496
FEATURE                  Location/Qualifiers
source                   1..496
                         mol_type = protein
                         organism = Vesicular stomatitis virus
SEQUENCE: 198
KFTIVFPHHQ KGNWKNVPST YHYCPSSSDQ NWHNDLTGVS LHVKIPFSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEQELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 199           moltype = AA  length = 496
FEATURE                  Location/Qualifiers
source                   1..496
                         mol_type = protein
                         organism = Vesicular stomatitis virus
SEQUENCE: 199
KFTIVFPHHQ KGNWKNVPST YHYCPSSSDQ NWHNDLTGVS LHVKIPQSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEAELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 200           moltype = AA  length = 496
FEATURE                  Location/Qualifiers
source                   1..496
                         mol_type = protein
                         organism = Vesicular stomatitis virus
SEQUENCE: 200
KFTIVFPHHQ KGNWKNVPST YHYCPSSSDQ NWHNDLTGVS LHVKIPQSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEGELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 201           moltype = AA  length = 496
FEATURE                  Location/Qualifiers
source                   1..496
                         mol_type = protein
                         organism = Vesicular stomatitis virus
SEQUENCE: 201
KFTIVFPHHQ KGNWKNVPST YHYCPSSSDQ NWHNDLTGVS LHVKIPQSHK AIQADGWMCH    60
AAKWVTTCDF RWYGPKYITH SIHSMSPTLE QCKTSIEQTK QGVWINPGFP PQSCGYATVT   120
DAEVVVVQAT PHHVLVDEYT GEWIDSQLVG GKCSKEVCQT VHNSTVWHAD YKITGLCESN   180
LASVDITFFS EDGQKTSLGK PNTGFRSNHF AYESGEKACR MQYCTQWGIR LPSGVWFELV   240
DKDLFQAAKL PECPRGSSIS APSQTSVDVS LIQDVERILD YSLCQETWSK IRAKLPVSPV   300
DLSYLAPKNP GSGPAFTIIN GTLKYFETRY IRVDISNPII PHMVGTMSGT TTEFELWNDW   360
YPYEDVEIGP NGVLKTPTGF KFPLYMIGHG MLDSDLHKSS QAQVFEHPHA KDAASQLPDD   420
ETLFFGDTGL SKNPVELVEG WFSSWKSTLA SFFLIIGLGV ALIFIIRIIV AIRYKYKGRK   480
TQKIYNDVEM SRLGNK                                                   496

SEQ ID NO: 202           moltype = AA  length = 496
```

| FEATURE | Location/Qualifiers |
|---|---|
| source | 1..496 |
| | mol_type = protein |
| | organism = Vesicular stomatitis virus |

SEQUENCE: 202

```
KFTIVFPHHQ KGNWKNVPST YHYCPSSSDQ NWHNDLTGVS LHVKIPQSHK AIQADGWMCH   60
AAKWVTTCDF RWYGPKYITH SIHSMSPTLE QCKTSIEQTK QGVWINPGFP PQSCGYATVT  120
DAEVVVVQAT PHHVLVDEYT GEWIDSQLVG GKCSKEVCQT VHNSTVWHAD YKITGLCESN  180
LASVDITFFS EDGQKTSLGK PNTGFRSNHF AYESGEKACR MQYCTQWGIR LPSGVWFELV  240
DKDLFQAAKL PECPRGSSIS APSQTSVDVS LIQDVERILD YSLCQETWSK IRAKLPVSPV  300
DLSYLAPKNP GSGPAFTIIN GTLKYFETRY IRVDISNPII PHMVGTMSGT TTEQELWNDW  360
YPYEDVEIGP NGVLKTPTGF KFPLYMIGHG MLDSDLHKSS QAQVFEHPHA KDAASQLPDD  420
ETLFFGDTGL SKNPVELVEG WFSSWKSTLA SFFLIIGLGV ALIFIIRIIV AIRYKYKGRK  480
TQKIYNDVEM SRLGNK                                                 496
```

| SEQ ID NO: 203 | moltype = AA length = 501 |
|---|---|
| FEATURE | Location/Qualifiers |
| source | 1..501 |
| | mol_type = protein |
| | organism = Vesicular stomatitis virus |

SEQUENCE: 203

```
KIEIVFPQHT TGDWKRVPHE YNYCPTSADK NSHGTQTGIP VELTMPAGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVRQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501
```

| SEQ ID NO: 204 | moltype = AA length = 501 |
|---|---|
| FEATURE | Location/Qualifiers |
| source | 1..501 |
| | mol_type = protein |
| | organism = Vesicular stomatitis virus |

SEQUENCE: 204

```
KIEIVFPQHT TGDWKRVPHE YNYCPTSADK NSHGTQTGIP VELTMPFGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVRQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501
```

| SEQ ID NO: 205 | moltype = AA length = 501 |
|---|---|
| FEATURE | Location/Qualifiers |
| source | 1..501 |
| | mol_type = protein |
| | organism = Vesicular stomatitis virus |

SEQUENCE: 205

```
KIEIVFPQHT TGDWKRVPHE YNYCPTSADK NSHGTQTGIP VELTMPGGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVRQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501
```

| SEQ ID NO: 206 | moltype = AA length = 501 |
|---|---|
| FEATURE | Location/Qualifiers |
| source | 1..501 |
| | mol_type = protein |
| | organism = Vesicular stomatitis virus |

SEQUENCE: 206

```
KIEIVFPQHT TGDWKRVPHE YNYCPTSADK NSHGTQTGIP VELTMPQGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVRQL  360
WDQWFPPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501
```

```
SEQ ID NO: 207          moltype = AA   length = 501
FEATURE                 Location/Qualifiers
source                  1..501
                        mol_type = protein
                        organism = Vesicular stomatitis virus
SEQUENCE: 207
KIEIVFPQHT TGDWKRVPHE YNYCPTSADK NSHGTQTGIP VELTMPKGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVAQL  360
WDQWFPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501

SEQ ID NO: 208          moltype = AA   length = 501
FEATURE                 Location/Qualifiers
source                  1..501
                        mol_type = protein
                        organism = Vesicular stomatitis virus
SEQUENCE: 208
KIEIVFPQHT TGDWKRVPHE YNYCPTSADK NSHGTQTGIP VELTMPKGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVFQL  360
WDQWFPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501

SEQ ID NO: 209          moltype = AA   length = 501
FEATURE                 Location/Qualifiers
source                  1..501
                        mol_type = protein
                        organism = Vesicular stomatitis virus
SEQUENCE: 209
KIEIVFPQHT TGDWKRVPHE YNYCPTSADK NSHGTQTGIP VELTMPKGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVGQL  360
WDQWFPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501

SEQ ID NO: 210          moltype = AA   length = 501
FEATURE                 Location/Qualifiers
source                  1..501
                        mol_type = protein
                        organism = Vesicular stomatitis virus
SEQUENCE: 210
KIEIVFPQHT TGDWKRVPHE YNYCPTSADK NSHGTQTGIP VELTMPKGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVQQL  360
WDQWFPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501

SEQ ID NO: 211          moltype = AA   length = 501
FEATURE                 Location/Qualifiers
source                  1..501
                        mol_type = protein
                        organism = Vesicular stomatitis virus
SEQUENCE: 211
KIEIVFPQHT TGDWKRVPHE YNYCPTSADK NSHGTQTGIP VELTMPAGLT THQVDGFMCH   60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVAQL  360
WDQWFPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501
```

```
SEQ ID NO: 212            moltype = AA  length = 501
FEATURE                   Location/Qualifiers
source                    1..501
                          mol_type = protein
                          organism = Vesicular stomatitis virus
SEQUENCE: 212
KIEIVFPQHT TGDWKRVPHE YNYCPTSADK NSHGTQTGIP VELTMPAGLT THQVDGFMCH   60
SALWMTTCDF RWYGPKYITH SIHNEEPTDY QCLEAIKAYK DGVSFNPGFP PQSCYGTVT   120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVGQL  360
WDQWFPPFGEV EIGPNGVLKT KQGYKFPLHI IGTGEVDNDI KMERIVKHWE HPHIEAAQTF 420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 213            moltype = AA  length = 501
FEATURE                   Location/Qualifiers
source                    1..501
                          mol_type = protein
                          organism = Vesicular stomatitis virus
SEQUENCE: 213
KIEIVFPQHT TGDWKRVPHE YNYCPTSADK NSHGTQTGIP VELTMPAGLT THQVDGFMCH   60
SALWMTTCDF RWYGPKYITH SIHNEEPTDY QCLEAIKAYK DGVSFNPGFP PQSCYGTVT   120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVGQL  360
WDQWFPPFGEV EIGPNGVLKT KQGYKFPLHI IGTGEVDNDI KMERIVKHWE HPHIEAAQTF 420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 214            moltype = AA  length = 501
FEATURE                   Location/Qualifiers
source                    1..501
                          mol_type = protein
                          organism = Vesicular stomatitis virus
SEQUENCE: 214
KIEIVFPQHT TGDWKRVPHE YNYCPTSADK NSHGTQTGIP VELTMPAGLT THQVDGFMCH   60
SALWMTTCDF RWYGPKYITH SIHNEEPTDY QCLEAIKAYK DGVSFNPGFP PQSCYGTVT   120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVQQL  360
WDQWFPPFGEV EIGPNGVLKT KQGYKFPLHI IGTGEVDNDI KMERIVKHWE HPHIEAAQTF 420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 215            moltype = AA  length = 501
FEATURE                   Location/Qualifiers
source                    1..501
                          mol_type = protein
                          organism = Vesicular stomatitis virus
SEQUENCE: 215
KIEIVFPQHT TGDWKRVPHE YNYCPTSADK NSHGTQTGIP VELTMPFGLT THQVDGFMCH   60
SALWMTTCDF RWYGPKYITH SIHNEEPTDY QCLEAIKAYK DGVSFNPGFP PQSCYGTVT   120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVAQL  360
WDQWFPPFGEV EIGPNGVLKT KQGYKFPLHI IGTGEVDNDI KMERIVKHWE HPHIEAAQTF 420
LKKDDTEEVL YYGDTGVSKN PVELVEGWFS GWRSSIMGVL AVIIGFVILI FLIRLIGVLS  480
SLFRQKRRPI YKSDVEMAHF R                                            501

SEQ ID NO: 216            moltype = AA  length = 501
FEATURE                   Location/Qualifiers
source                    1..501
                          mol_type = protein
                          organism = Vesicular stomatitis virus
SEQUENCE: 216
KIEIVFPQHT TGDWKRVPHE YNYCPTSADK NSHGTQTGIP VELTMPFGLT THQVDGFMCH   60
SALWMTTCDF RWYGPKYITH SIHNEEPTDY QCLEAIKAYK DGVSFNPGFP PQSCYGTVT   120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVGQL  360
WDQWFPPFGEV EIGPNGVLKT KQGYKFPLHI IGTGEVDNDI KMERIVKHWE HPHIEAAQTF 420
LKKDDTEEVL YYGDTGVSKN PVELVEGWFS GWRSSIMGVL AVIIGFVILI FLIRLIGVLS  480
```

```
SLFRQKRRPI YKSDVEMAHF R                                                      501

SEQ ID NO: 217           moltype = AA  length = 501
FEATURE                  Location/Qualifiers
source                   1..501
                         mol_type = protein
                         organism = Vesicular stomatitis virus
SEQUENCE: 217
KIEIVFPQHT TGDWKRVPHE YNYCPTSADK NSHGTQTGIP VELTMPFGLT THQVDGFMCH             60
SALWMTTCDF RWYGPKYITH SIHNEEPTDY QCLEAIKAYK DGVSFNPGFP PQSCGYGTVT            120
DAEAHIVTVT PHSVKVDEYT GEWIDPHFIG GRCKGQICET VHNSTKWFTS SDGESVCSQL            180
FTLVGGTFFS DSEEITSMGL PETGIRSNYF PYVSTEGICK MPFCRKPGYK LKNDLWFQIT            240
DPDLDKTVRD LPHIKDCDLS SSIVTPGEHA TDISLISDVE RILDYALCQN TWSKIEAGEP            300
ITPVDLSYLG PKNPGAGPVF TIINGSLHYF MSKYLRVELE SPVIPRMEGK VAGTRIVGQL            360
WDQWFPFGEV EIGPNGVLKT KQGYKFPLHI IGTGEVDNDI KMERIVKHWE HPHIEAAQTF            420
LKKDDTEEVL YYGDTGVSKN PVELVEGWFS GWRSSIMGVL AVIIGFVILI FLIRLIGVLS            480
SLFRQKRRPI YKSDVEMAHF R                                                      501

SEQ ID NO: 218           moltype = AA  length = 501
FEATURE                  Location/Qualifiers
source                   1..501
                         mol_type = protein
                         organism = Vesicular stomatitis virus
SEQUENCE: 218
KIEIVFPQHT TGDWKRVPHE YNYCPTSADK NSHGTQTGIP VELTMPFGLT THQVDGFMCH             60
SALWMTTCDF RWYGPKYITH SIHNEEPTDY QCLEAIKAYK DGVSFNPGFP PQSCGYGTVT            120
DAEAHIVTVT PHSVKVDEYT GEWIDPHFIG GRCKGQICET VHNSTKWFTS SDGESVCSQL            180
FTLVGGTFFS DSEEITSMGL PETGIRSNYF PYVSTEGICK MPFCRKPGYK LKNDLWFQIT            240
DPDLDKTVRD LPHIKDCDLS SSIVTPGEHA TDISLISDVE RILDYALCQN TWSKIEAGEP            300
ITPVDLSYLG PKNPGAGPVF TIINGSLHYF MSKYLRVELE SPVIPRMEGK VAGTRIVGQL            360
WDQWFPFGEV EIGPNGVLKT KQGYKFPLHI IGTGEVDNDI KMERIVKHWE HPHIEAAQTF            420
LKKDDTEEVL YYGDTGVSKN PVELVEGWFS GWRSSIMGVL AVIIGFVILI FLIRLIGVLS            480
SLFRQKRRPI YKSDVEMAHF R                                                      501

SEQ ID NO: 219           moltype = AA  length = 501
FEATURE                  Location/Qualifiers
source                   1..501
                         mol_type = protein
                         organism = Vesicular stomatitis virus
SEQUENCE: 219
KIEIVFPQHT TGDWKRVPHE YNYCPTSADK NSHGTQTGIP VELTMPGGLT THQVDGFMCH             60
SALWMTTCDF RWYGPKYITH SIHNEEPTDY QCLEAIKAYK DGVSFNPGFP PQSCGYGTVT            120
DAEAHIVTVT PHSVKVDEYT GEWIDPHFIG GRCKGQICET VHNSTKWFTS SDGESVCSQL            180
FTLVGGTFFS DSEEITSMGL PETGIRSNYF PYVSTEGICK MPFCRKPGYK LKNDLWFQIT            240
DPDLDKTVRD LPHIKDCDLS SSIVTPGEHA TDISLISDVE RILDYALCQN TWSKIEAGEP            300
ITPVDLSYLG PKNPGAGPVF TIINGSLHYF MSKYLRVELE SPVIPRMEGK VAGTRIVAQL            360
WDQWFPFGEV EIGPNGVLKT KQGYKFPLHI IGTGEVDNDI KMERIVKHWE HPHIEAAQTF            420
LKKDDTEEVL YYGDTGVSKN PVELVEGWFS GWRSSIMGVL AVIIGFVILI FLIRLIGVLS            480
SLFRQKRRPI YKSDVEMAHF R                                                      501

SEQ ID NO: 220           moltype = AA  length = 501
FEATURE                  Location/Qualifiers
source                   1..501
                         mol_type = protein
                         organism = Vesicular stomatitis virus
SEQUENCE: 220
KIEIVFPQHT TGDWKRVPHE YNYCPTSADK NSHGTQTGIP VELTMPGGLT THQVDGFMCH             60
SALWMTTCDF RWYGPKYITH SIHNEEPTDY QCLEAIKAYK DGVSFNPGFP PQSCGYGTVT            120
DAEAHIVTVT PHSVKVDEYT GEWIDPHFIG GRCKGQICET VHNSTKWFTS SDGESVCSQL            180
FTLVGGTFFS DSEEITSMGL PETGIRSNYF PYVSTEGICK MPFCRKPGYK LKNDLWFQIT            240
DPDLDKTVRD LPHIKDCDLS SSIVTPGEHA TDISLISDVE RILDYALCQN TWSKIEAGEP            300
ITPVDLSYLG PKNPGAGPVF TIINGSLHYF MSKYLRVELE SPVIPRMEGK VAGTRIVFQL            360
WDQWFPFGEV EIGPNGVLKT KQGYKFPLHI IGTGEVDNDI KMERIVKHWE HPHIEAAQTF            420
LKKDDTEEVL YYGDTGVSKN PVELVEGWFS GWRSSIMGVL AVIIGFVILI FLIRLIGVLS            480
SLFRQKRRPI YKSDVEMAHF R                                                      501

SEQ ID NO: 221           moltype = AA  length = 501
FEATURE                  Location/Qualifiers
source                   1..501
                         mol_type = protein
                         organism = Vesicular stomatitis virus
SEQUENCE: 221
KIEIVFPQHT TGDWKRVPHE YNYCPTSADK NSHGTQTGIP VELTMPGGLT THQVDGFMCH             60
SALWMTTCDF RWYGPKYITH SIHNEEPTDY QCLEAIKAYK DGVSFNPGFP PQSCGYGTVT            120
DAEAHIVTVT PHSVKVDEYT GEWIDPHFIG GRCKGQICET VHNSTKWFTS SDGESVCSQL            180
FTLVGGTFFS DSEEITSMGL PETGIRSNYF PYVSTEGICK MPFCRKPGYK LKNDLWFQIT            240
DPDLDKTVRD LPHIKDCDLS SSIVTPGEHA TDISLISDVE RILDYALCQN TWSKIEAGEP            300
ITPVDLSYLG PKNPGAGPVF TIINGSLHYF MSKYLRVELE SPVIPRMEGK VAGTRIVGQL            360
WDQWFPFGEV EIGPNGVLKT KQGYKFPLHI IGTGEVDNDI KMERIVKHWE HPHIEAAQTF            420
```

```
LKKDDTEEVL YYGDTGVSKN PVELVEGWFS GWRSSIMGVL AVIIGFVILI FLIRLIGVLS    480
SLFRQKRRPI YKSDVEMAHF R                                              501

SEQ ID NO: 222          moltype = AA  length = 501
FEATURE                 Location/Qualifiers
source                  1..501
                        mol_type = protein
                        organism = Vesicular stomatitis virus
SEQUENCE: 222
KIEIVFPQHT TGDWKRVPHE YNYCPTSADK NSHGTQTGIP VELTMPGGLT THQVDGFMCH     60
SALWMTTCDF RWYGPKYITH SIHNEEPTDY QCLEAIKAYK DGVSFNPGFP PQSCGYGTVT    120
DAEAHIVTVT PHSVKVDEYT GEWIDPHFIG GRCKGQICET VHNSTKWFTS SDGESVCSQL    180
FTLVGGTFFS DSEEITSMGL PETGIRSNYF PYVSTEGICK MPFCRKPGYK LKNDLWFQIT    240
DPDLDKTVRD LPHIKDCDLS SSIVTPGEHA TDISLISDVE RILDYALCQN TWSKIEAGEP    300
ITPVDLSYLG PKNPGAGPVF TIINGSLHYF MSKYLRVELE SPVIPRMEGK VAGTRIVQQL    360
WDQWFPFGEV EIGPNGVLKT KQGYKFPLHI IGTGEVDNDI KMERIVKHWE HPHIEAAQTF    420
LKKDDTEEVL YYGDTGVSKN PVELVEGWFS GWRSSIMGVL AVIIGFVILI FLIRLIGVLS    480
SLFRQKRRPI YKSDVEMAHF R                                              501

SEQ ID NO: 223          moltype = AA  length = 501
FEATURE                 Location/Qualifiers
source                  1..501
                        mol_type = protein
                        organism = Vesicular stomatitis virus
SEQUENCE: 223
KIEIVFPQHT TGDWKRVPHE YNYCPTSADK NSHGTQTGIP VELTMPGGLT THQVDGFMCH     60
SALWMTTCDF RWYGPKYITH SIHNEEPTDY QCLEAIKAYK DGVSFNPGFP PQSCGYGTVT    120
DAEAHIVTVT PHSVKVDEYT GEWIDPHFIG GRCKGQICET VHNSTKWFTS SDGESVCSQL    180
FTLVGGTFFS DSEEITSMGL PETGIRSNYF PYVSTEGICK MPFCRKPGYK LKNDLWFQIT    240
DPDLDKTVRD LPHIKDCDLS SSIVTPGEHA TDISLISDVE RILDYALCQN TWSKIEAGEP    300
ITPVDLSYLG PKNPGAGPVF TIINGSLHYF MSKYLRVELE SPVIPRMEGK VAGTRIVAQL    360
WDQWFPFGEV EIGPNGVLKT KQGYKFPLHI IGTGEVDNDI KMERIVKHWE HPHIEAAQTF    420
LKKDDTEEVL YYGDTGVSKN PVELVEGWFS GWRSSIMGVL AVIIGFVILI FLIRLIGVLS    480
SLFRQKRRPI YKSDVEMAHF R                                              501

SEQ ID NO: 224          moltype = AA  length = 501
FEATURE                 Location/Qualifiers
source                  1..501
                        mol_type = protein
                        organism = Vesicular stomatitis virus
SEQUENCE: 224
KIEIVFPQHT TGDWKRVPHE YNYCPTSADK NSHGTQTGIP VELTMPGGLT THQVDGFMCH     60
SALWMTTCDF RWYGPKYITH SIHNEEPTDY QCLEAIKAYK DGVSFNPGFP PQSCGYGTVT    120
DAEAHIVTVT PHSVKVDEYT GEWIDPHFIG GRCKGQICET VHNSTKWFTS SDGESVCSQL    180
FTLVGGTFFS DSEEITSMGL PETGIRSNYF PYVSTEGICK MPFCRKPGYK LKNDLWFQIT    240
DPDLDKTVRD LPHIKDCDLS SSIVTPGEHA TDISLISDVE RILDYALCQN TWSKIEAGEP    300
ITPVDLSYLG PKNPGAGPVF TIINGSLHYF MSKYLRVELE SPVIPRMEGK VAGTRIVFQL    360
WDQWFPFGEV EIGPNGVLKT KQGYKFPLHI IGTGEVDNDI KMERIVKHWE HPHIEAAQTF    420
LKKDDTEEVL YYGDTGVSKN PVELVEGWFS GWRSSIMGVL AVIIGFVILI FLIRLIGVLS    480
SLFRQKRRPI YKSDVEMAHF R                                              501

SEQ ID NO: 225          moltype = AA  length = 501
FEATURE                 Location/Qualifiers
source                  1..501
                        mol_type = protein
                        organism = Vesicular stomatitis virus
SEQUENCE: 225
KIEIVFPQHT TGDWKRVPHE YNYCPTSADK NSHGTQTGIP VELTMPGGLT THQVDGFMCH     60
SALWMTTCDF RWYGPKYITH SIHNEEPTDY QCLEAIKAYK DGVSFNPGFP PQSCGYGTVT    120
DAEAHIVTVT PHSVKVDEYT GEWIDPHFIG GRCKGQICET VHNSTKWFTS SDGESVCSQL    180
FTLVGGTFFS DSEEITSMGL PETGIRSNYF PYVSTEGICK MPFCRKPGYK LKNDLWFQIT    240
DPDLDKTVRD LPHIKDCDLS SSIVTPGEHA TDISLISDVE RILDYALCQN TWSKIEAGEP    300
ITPVDLSYLG PKNPGAGPVF TIINGSLHYF MSKYLRVELE SPVIPRMEGK VAGTRIVSQL    360
WDQWFPFGEV EIGPNGVLKT KQGYKFPLHI IGTGEVDNDI KMERIVKHWE HPHIEAAQTF    420
LKKDDTEEVL YYGDTGVSKN PVELVEGWFS GWRSSIMGVL AVIIGFVILI FLIRLIGVLS    480
SLFRQKRRPI YKSDVEMAHF R                                              501

SEQ ID NO: 226          moltype = AA  length = 501
FEATURE                 Location/Qualifiers
source                  1..501
                        mol_type = protein
                        organism = Vesicular stomatitis virus
SEQUENCE: 226
KIEIVFPQHT TGDWKRVPHE YNYCPTSADK NSHGTQTGIP VELTMPGGLT THQVDGFMCH     60
SALWMTTCDF RWYGPKYITH SIHNEEPTDY QCLEAIKAYK DGVSFNPGFP PQSCGYGTVT    120
DAEAHIVTVT PHSVKVDEYT GEWIDPHFIG GRCKGQICET VHNSTKWFTS SDGESVCSQL    180
FTLVGGTFFS DSEEITSMGL PETGIRSNYF PYVSTEGICK MPFCRKPGYK LKNDLWFQIT    240
DPDLDKTVRD LPHIKDCDLS SSIVTPGEHA TDISLISDVE RILDYALCQN TWSKIEAGEP    300
ITPVDLSYLG PKNPGAGPVF TIINGSLHYF MSKYLRVELE SPVIPRMEGK VAGTRIVQQL    360
```

```
WDQWFPPFGEV EIGPNGVLKT KQGYKFPLHI IGTGEVDNDI KMERIVKHWE HPHIEAAQTF    420
LKKDDTEEVL YYGDTGVSKN PVELVEGWFS GWRSSIMGVL AVIIGFVILI FLIRLIGVLS    480
SLFRQKRRPI YKSDVEMAHF R                                              501

SEQ ID NO: 227            moltype = AA  length = 502
FEATURE                   Location/Qualifiers
source                    1..502
                          mol_type = protein
                          organism = Vesicular stomatitis virus
SEQUENCE: 227
KITISFPQSL KGDWRPVPKG YNYCPTSADK NLHGDLIDIG LRLRAPASFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSRVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 228            moltype = AA  length = 502
FEATURE                   Location/Qualifiers
source                    1..502
                          mol_type = protein
                          organism = Vesicular stomatitis virus
SEQUENCE: 228
KITISFPQSL KGDWRPVPKG YNYCPTSADK NLHGDLIDIG LRLRAPFSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSRVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 229            moltype = AA  length = 502
FEATURE                   Location/Qualifiers
source                    1..502
                          mol_type = protein
                          organism = Vesicular stomatitis virus
SEQUENCE: 229
KITISFPQSL KGDWRPVPKG YNYCPTSADK NLHGDLIDIG LRLRAPGSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSRVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 230            moltype = AA  length = 502
FEATURE                   Location/Qualifiers
source                    1..502
                          mol_type = protein
                          organism = Vesicular stomatitis virus
SEQUENCE: 230
KITISFPQSL KGDWRPVPKG YNYCPTSADK NLHGDLIDIG LRLRAPQSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSRVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 231            moltype = AA  length = 502
FEATURE                   Location/Qualifiers
source                    1..502
                          mol_type = protein
                          organism = Vesicular stomatitis virus
SEQUENCE: 231
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
```

```
LTPIDISYLG PKNPGPGPAF TIINGTLHYF NTRYIRVDIA GPVTKEITGF VSGTSTSAVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 232          moltype = AA   length = 502
FEATURE                 Location/Qualifiers
source                  1..502
                        mol_type = protein
                        organism = Vesicular stomatitis virus
SEQUENCE: 232
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSFVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 233          moltype = AA   length = 502
FEATURE                 Location/Qualifiers
source                  1..502
                        mol_type = protein
                        organism = Vesicular stomatitis virus
SEQUENCE: 233
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSGVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 234          moltype = AA   length = 502
FEATURE                 Location/Qualifiers
source                  1..502
                        mol_type = protein
                        organism = Vesicular stomatitis virus
SEQUENCE: 234
KITISFPQSL KGDWRPVPKG YNYCPTSADK NLHGDLIDIG LRLRAPKSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSQVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 235          moltype = AA   length = 502
FEATURE                 Location/Qualifiers
source                  1..502
                        mol_type = protein
                        organism = Vesicular stomatitis virus
SEQUENCE: 235
KITISFPQSL KGDWRPVPKG YNYCPTSADK NLHGDLIDIG LRLRAPASFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSAVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 236          moltype = AA   length = 502
FEATURE                 Location/Qualifiers
source                  1..502
                        mol_type = protein
                        organism = Vesicular stomatitis virus
SEQUENCE: 236
KITISFPQSL KGDWRPVPKG YNYCPTSADK NLHGDLIDIG LRLRAPASFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
```

```
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSFVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 237          moltype = AA  length = 502
FEATURE                 Location/Qualifiers
source                  1..502
                        mol_type = protein
                        organism = Vesicular stomatitis virus
SEQUENCE: 237
KITISFPQSL KGDWRPVPKG YNYCPTSADK NLHGDLIDIG LRLRAPASFK GISADGWMCH     60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSFVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 238          moltype = AA  length = 502
FEATURE                 Location/Qualifiers
source                  1..502
                        mol_type = protein
                        organism = Vesicular stomatitis virus
SEQUENCE: 238
KITISFPQSL KGDWRPVPKG YNYCPTSADK NLHGDLIDIG LRLRAPASFK GISADGWMCH     60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSQVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 239          moltype = AA  length = 502
FEATURE                 Location/Qualifiers
source                  1..502
                        mol_type = protein
                        organism = Vesicular stomatitis virus
SEQUENCE: 239
KITISFPQSL KGDWRPVPKG YNYCPTSADK NLHGDLIDIG LRLRAPFSFK GISADGWMCH     60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSAVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 240          moltype = AA  length = 502
FEATURE                 Location/Qualifiers
source                  1..502
                        mol_type = protein
                        organism = Vesicular stomatitis virus
SEQUENCE: 240
KITISFPQSL KGDWRPVPKG YNYCPTSADK NLHGDLIDIG LRLRAPFSFK GISADGWMCH     60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSFVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 241          moltype = AA  length = 502
FEATURE                 Location/Qualifiers
source                  1..502
                        mol_type = protein
                        organism = Vesicular stomatitis virus
SEQUENCE: 241
KITISFPQSL KGDWRPVPKG YNYCPTSADK NLHGDLIDIG LRLRAPFSFK GISADGWMCH     60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
```

```
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSGVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 242          moltype = AA  length = 502
FEATURE                 Location/Qualifiers
source                  1..502
                        mol_type = protein
                        organism = Vesicular stomatitis virus
SEQUENCE: 242
KITISFPQSL KGDWRPVPKG YNYCPTSADK NLHGDLIDIG LRLRAPFSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSQVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 243          moltype = AA  length = 502
FEATURE                 Location/Qualifiers
source                  1..502
                        mol_type = protein
                        organism = Vesicular stomatitis virus
SEQUENCE: 243
KITISFPQSL KGDWRPVPKG YNYCPTSADK NLHGDLIDIG LRLRAPGSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSAVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 244          moltype = AA  length = 502
FEATURE                 Location/Qualifiers
source                  1..502
                        mol_type = protein
                        organism = Vesicular stomatitis virus
SEQUENCE: 244
KITISFPQSL KGDWRPVPKG YNYCPTSADK NLHGDLIDIG LRLRAPGSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSVL     360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 245          moltype = AA  length = 502
FEATURE                 Location/Qualifiers
source                  1..502
                        mol_type = protein
                        organism = Vesicular stomatitis virus
SEQUENCE: 245
KITISFPQSL KGDWRPVPKG YNYCPTSADK NLHGDLIDIG LRLRAPGSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHKAQV ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSGVL    360
WDQWFPYGEN SIGPNGLLKT ASGYKYPLFM VGTGVLDADI HKLGEATVIE HPAKEAQKV     420
VDDSEVIFFG DTGVSKNPVE VVEGWFSGWR SSLMSIFGII LLIVCLVLIV RILIALKYCC    480
VRHKKRTIYK EDLEMGRIPR RA                                             502

SEQ ID NO: 246          moltype = AA  length = 502
FEATURE                 Location/Qualifiers
source                  1..502
                        mol_type = protein
                        organism = Vesicular stomatitis virus
SEQUENCE: 246
KITISFPQSL KGDWRPVPKG YNYCPTSADK NLHGDLIDIG LRLRAPGSFK GISADGWMCH    60
AARWITTCDF RWYGPKYITH SIHSFRPSND QCKEAIRLTN EGNWINPGFP PQSCGYASVT    120
```

```
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSQVL    360
WDQWFPYGEN SIGPNGLLKT ASGYKYPLFM VGTGVLDADI HKLGEATVIE HPHAKEQKVC    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 247          moltype = AA  length = 502
FEATURE                 Location/Qualifiers
source                  1..502
                        mol_type = protein
                        organism = Vesicular stomatitis virus
SEQUENCE: 247
KITISFPQSL KGDWRPVPKG YNYCPTSADK NLHGDLIDIG LRLRAPQSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSAVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 248          moltype = AA  length = 502
FEATURE                 Location/Qualifiers
source                  1..502
                        mol_type = protein
                        organism = Vesicular stomatitis virus
SEQUENCE: 248
KITISFPQSL KGDWRPVPKG YNYCPTSADK NLHGDLIDIG LRLRAPQSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSFVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 249          moltype = AA  length = 502
FEATURE                 Location/Qualifiers
source                  1..502
                        mol_type = protein
                        organism = Vesicular stomatitis virus
SEQUENCE: 249
KITISFPQSL KGDWRPVPKG YNYCPTSADK NLHGDLIDIG LRLRAPQSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSGVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 250          moltype = AA  length = 502
FEATURE                 Location/Qualifiers
source                  1..502
                        mol_type = protein
                        organism = Vesicular stomatitis virus
SEQUENCE: 250
KITISFPQSL KGDWRPVPKG YNYCPTSADK NLHGDLIDIG LRLRAPQSFK GISADGWMCH    60
AARWITTCDF RWYGPKYITH SIHSFRPSND QCKEAIRLTN EGNWINPGFP PQSCGYASVT    120
DSESVVVTVT KHQVLVDEYS GSWIDSQFPG GSCTSPICDT VHNSTLWHAD HTLDSICDQE    180
FVAMDAVLFT ESGKFEEFGK PNSGIRSNYF PYESLKDVCQ MDFCKRKGFK LPSGVWFEIE    240
DAEKSHAQV  ELKIKRCPHG AVISAPNQNA ADINLIMDVE RILDYSLCQA TWSKIQNKEA    300
LTPIDISYLG PKNPGPGPAF TIINGTLHYF NTRYIRVDIA GPVTKEITGF VSGTSTSQVL    360
WDQWFPYGEN SIGPNGLLKT ASGYKYPLFM VGTGVLDADI HKLGEATVIE HPHAKEAQKV    420
VDDSEVIFFG DTGVSKNPVE VVEGWFSGWR SSLMSIFGII LLIVCLVLIV RILIALKYCC    480
VRHKKRTIYK EDLEMGRIPR RA                                            502

SEQ ID NO: 251          moltype = AA  length = 494
FEATURE                 Location/Qualifiers
source                  1..494
                        mol_type = protein
                        organism = Vesicular stomatitis virus
SEQUENCE: 251
KFTIVFPQSQ KGDWKDVPPN YRYCPSSADQ NWHGDLLGVN IRAKMPAVHK AIKADGWMCH    60
```

```
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 252          moltype = AA   length = 494
FEATURE                 Location/Qualifiers
source                  1..494
                        mol_type = protein
                        organism = Vesicular stomatitis virus
SEQUENCE: 252
KFTIVFPQSQ KGDWKDVPPN YRYCPSSADQ NWHGDLLGVN IRAKMPFVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 253          moltype = AA   length = 494
FEATURE                 Location/Qualifiers
source                  1..494
                        mol_type = protein
                        organism = Vesicular stomatitis virus
SEQUENCE: 253
KFTIVFPQSQ KGDWKDVPPN YRYCPSSADQ NWHGDLLGVN IRAKMPGVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 254          moltype = AA   length = 494
FEATURE                 Location/Qualifiers
source                  1..494
                        mol_type = protein
                        organism = Vesicular stomatitis virus
SEQUENCE: 254
KFTIVFPQSQ KGDWKDVPPN YRYCPSSADQ NWHGDLLGVN IRAKMPQVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKRELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 255          moltype = AA   length = 494
FEATURE                 Location/Qualifiers
source                  1..494
                        mol_type = protein
                        organism = Vesicular stomatitis virus
SEQUENCE: 255
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKAELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 256          moltype = AA   length = 494
FEATURE                 Location/Qualifiers
source                  1..494
                        mol_type = protein
                        organism = Vesicular stomatitis virus
SEQUENCE: 256
```

```
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKFELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 257           moltype = AA  length = 494
FEATURE                  Location/Qualifiers
source                   1..494
                         mol_type = protein
                         organism = Vesicular stomatitis virus
SEQUENCE: 257
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKQELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 258           moltype = AA  length = 494
FEATURE                  Location/Qualifiers
source                   1..494
                         mol_type = protein
                         organism = Vesicular stomatitis virus
SEQUENCE: 258
KFTIVFPQSQ KGDWKDVPPN YRYCPSSADQ NWHGDLLGVN IRAKMPKVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKQELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 259           moltype = AA  length = 494
FEATURE                  Location/Qualifiers
source                   1..494
                         mol_type = protein
                         organism = Vesicular stomatitis virus
SEQUENCE: 259
KFTIVFPQSQ KGDWKDVPPN YRYCPSSADQ NWHGDLLGVN IRAKMPAVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKAELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 260           moltype = AA  length = 494
FEATURE                  Location/Qualifiers
source                   1..494
                         mol_type = protein
                         organism = Vesicular stomatitis virus
SEQUENCE: 260
KFTIVFPQSQ KGDWKDVPPN YRYCPSSADQ NWHGDLLGVN IRAKMPAVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKFELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 261           moltype = AA  length = 494
FEATURE                  Location/Qualifiers
source                   1..494
                         mol_type = protein
                         organism = Vesicular stomatitis virus
```

```
SEQUENCE: 261
KFTIVFPQSQ KGDWKDVPPN YRYCPSSADQ NWHGDLLGVN IRAKMPAVHK AIKADGWMCH      60
AAKWVTTCDY RWYGPQYITH SIHSFIPTKA QCEESIKQTK EGVWINPGFP PKNCGYASVS     120
DAESIIVQAT AHSVMIDEYS GDWLDSQFPT GRCTGSTCET IHNSTLWYAD YQVTGLCDSA     180
LVSTEVTFYS EDGLMTSIGR QNTGYRSNYF PYEKGAAACR MKYCTHEGIR LPSGVWFEMV     240
DKELLESVQM PECPAGLTIS APTQTSVDVS LILDVERMLD YSLCQETWSK VHSGLPISPV     300
DLGYIAPKNP GAGPAFTIVN GTLKYFDTRY LRIDIEGPVL KKMTGKVSGT PTKGELWTEW     360
FPYDDVEIGP NGVLKTPEGY KFPLYMIGHG LLDSDLQKTS QAEVFHHPQI AEAVQKLPDD     420
ETLFFGDTGI SKNPVEVIEG WFSNWRSSVM AIVFAILLLV ITVLMVRLCV AFRHFCCQKR     480
HKIYNDLEMN QLRR                                                      494

SEQ ID NO: 262          moltype = AA  length = 494
FEATURE                 Location/Qualifiers
source                  1..494
                        mol_type = protein
                        organism = Vesicular stomatitis virus
SEQUENCE: 262
KFTIVFPQSQ KGDWKDVPPN YRYCPSSADQ NWHGDLLGVN IRAKMPAVHK AIKADGWMCH      60
AAKWVTTCDY RWYGPQYITH SIHSFIPTKA QCEESIKQTK EGVWINPGFP PKNCGYASVS     120
DAESIIVQAT AHSVMIDEYS GDWLDSQFPT GRCTGSTCET IHNSTLWYAD YQVTGLCDSA     180
LVSTEVTFYS EDGLMTSIGR QNTGYRSNYF PYEKGAAACR MKYCTHEGIR LPSGVWFEMV     240
DKELLESVQM PECPAGLTIS APTQTSVDVS LILDVERMLD YSLCQETWSK VHSGLPISPV     300
DLGYIAPKNP GAGPAFTIVN GTLKYFDTRY LRIDIEGPVL KKMTGKVSGT PTKQELWTEW     360
FPYDDVEIGP NGVLKTPEGY KFPLYMIGHG LLDSDLQKTS QAEVFHHPQI AEAVQKLPDD     420
ETLFFGDTGI SKNPVEVIEG WFSNWRSSVM AIVFAILLLV ITVLMVRLCV AFRHFCCQKR     480
HKIYNDLEMN QLRR                                                      494

SEQ ID NO: 263          moltype = AA  length = 494
FEATURE                 Location/Qualifiers
source                  1..494
                        mol_type = protein
                        organism = Vesicular stomatitis virus
SEQUENCE: 263
KFTIVFPQSQ KGDWKDVPPN YRYCPSSADQ NWHGDLLGVN IRAKMPFVHK AIKADGWMCH      60
AAKWVTTCDY RWYGPQYITH SIHSFIPTKA QCEESIKQTK EGVWINPGFP PKNCGYASVS     120
DAESIIVQAT AHSVMIDEYS GDWLDSQFPT GRCTGSTCET IHNSTLWYAD YQVTGLCDSA     180
LVSTEVTFYS EDGLMTSIGR QNTGYRSNYF PYEKGAAACR MKYCTHEGIR LPSGVWFEMV     240
DKELLESVQM PECPAGLTIS APTQTSVDVS LILDVERMLD YSLCQETWSK VHSGLPISPV     300
DLGYIAPKNP GAGPAFTIVN GTLKYFDTRY LRIDIEGPVL KKMTGKVSGT PTKAELWTEW     360
FPYDDVEIGP NGVLKTPEGY KFPLYMIGHG LLDSDLQKTS QAEVFHHPQI AEAVQKLPDD     420
ETLFFGDTGI SKNPVEVIEG WFSNWRSSVM AIVFAILLLV ITVLMVRLCV AFRHFCCQKR     480
HKIYNDLEMN QLRR                                                      494

SEQ ID NO: 264          moltype = AA  length = 494
FEATURE                 Location/Qualifiers
source                  1..494
                        mol_type = protein
                        organism = Vesicular stomatitis virus
SEQUENCE: 264
KFTIVFPQSQ KGDWKDVPPN YRYCPSSADQ NWHGDLLGVN IRAKMPFVHK AIKADGWMCH      60
AAKWVTTCDY RWYGPQYITH SIHSFIPTKA QCEESIKQTK EGVWINPGFP PKNCGYASVS     120
DAESIIVQAT AHSVMIDEYS GDWLDSQFPT GRCTGSTCET IHNSTLWYAD YQVTGLCDSA     180
LVSTEVTFYS EDGLMTSIGR QNTGYRSNYF PYEKGAAACR MKYCTHEGIR LPSGVWFEMV     240
DKELLESVQM PECPAGLTIS APTQTSVDVS LILDVERMLD YSLCQETWSK VHSGLPISPV     300
DLGYIAPKNP GAGPAFTIVN GTLKYFDTRY LRIDIEGPVL KKMTGKVSGT PTKFELWTEW     360
FPYDDVEIGP NGVLKTPEGY KFPLYMIGHG LLDSDLQKTS QAEVFHHPQI AEAVQKLPDD     420
ETLFFGDTGI SKNPVEVIEG WFSNWRSSVM AIVFAILLLV ITVLMVRLCV AFRHFCCQKR     480
HKIYNDLEMN QLRR                                                      494

SEQ ID NO: 265          moltype = AA  length = 494
FEATURE                 Location/Qualifiers
source                  1..494
                        mol_type = protein
                        organism = Vesicular stomatitis virus
SEQUENCE: 265
KFTIVFPQSQ KGDWKDVPPN YRYCPSSADQ NWHGDLLGVN IRAKMPFVHK AIKADGWMCH      60
AAKWVTTCDY RWYGPQYITH SIHSFIPTKA QCEESIKQTK EGVWINPGFP PKNCGYASVS     120
DAESIIVQAT AHSVMIDEYS GDWLDSQFPT GRCTGSTCET IHNSTLWYAD YQVTGLCDSA     180
LVSTEVTFYS EDGLMTSIGR QNTGYRSNYF PYEKGAAACR MKYCTHEGIR LPSGVWFEMV     240
DKELLESVQM PECPAGLTIS APTQTSVDVS LILDVERMLD YSLCQETWSK VHSGLPISPV     300
DLGYIAPKNP GAGPAFTIVN GTLKYFDTRY LRIDIEGPVL KKMTGKVSGT PTKGELWTEW     360
FPYDDVEIGP NGVLKTPEGY KFPLYMIGHG LLDSDLQKTS QAEVFHHPQI AEAVQKLPDD     420
ETLFFGDTGI SKNPVEVIEG WFSNWRSSVM AIVFAILLLV ITVLMVRLCV AFRHFCCQKR     480
HKIYNDLEMN QLRR                                                      494

SEQ ID NO: 266          moltype = AA  length = 494
FEATURE                 Location/Qualifiers
source                  1..494
                        mol_type = protein
```

```
                        organism = Vesicular stomatitis virus
SEQUENCE: 266
KFTIVFPQSQ KGDWKDVPPN YRYCPSSADQ NWHGDLLGVN IRAKMPFVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKQELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 267          moltype = AA  length = 494
FEATURE                 Location/Qualifiers
source                  1..494
                        mol_type = protein
                        organism = Vesicular stomatitis virus
SEQUENCE: 267
KFTIVFPQSQ KGDWKDVPPN YRYCPSSADQ NWHGDLLGVN IRAKMPGVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKAELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 268          moltype = AA  length = 494
FEATURE                 Location/Qualifiers
source                  1..494
                        mol_type = protein
                        organism = Vesicular stomatitis virus
SEQUENCE: 268
KFTIVFPQSQ KGDWKDVPPN YRYCPSSADQ NWHGDLLGVN IRAKMPGVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKFELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 269          moltype = AA  length = 494
FEATURE                 Location/Qualifiers
source                  1..494
                        mol_type = protein
                        organism = Vesicular stomatitis virus
SEQUENCE: 269
KFTIVFPQSQ KGDWKDVPPN YRYCPSSADQ NWHGDLLGVN IRAKMPGVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKGELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 270          moltype = AA  length = 494
FEATURE                 Location/Qualifiers
source                  1..494
                        mol_type = protein
                        organism = Vesicular stomatitis virus
SEQUENCE: 270
KFTIVFPQSQ KGDWKDVPPN YRYCPSSADQ NWHGDLLGVN IRAKMPGVHK AIKADGWMCH    60
AAKWVTTCDY RWYGPQYITH SIHSFIPTKA QCEESIKQTK EGVWINPGFP PKNCGYASVS   120
DAESIIVQAT AHSVMIDEYS GDWLDSQFPT GRCTGSTCET IHNSTLWYAD YQVTGLCDSA   180
LVSTEVTFYS EDGLMTSIGR QNTGYRSNYF PYEKGAAACR MKYCTHEGIR LPSGVWFEMV   240
DKELLESVQM PECPAGLTIS APTQTSVDVS LILDVERMLD YSLCQETWSK VHSGLPISPV   300
DLGYIAPKNP GAGPAFTIVN GTLKYFDTRY LRIDIEGPVL KKMTGKVSGT PTKQELWTEW   360
FPYDDVEIGP NGVLKTPEGY KFPLYMIGHG LLDSDLQKTS QAEVFHHPQI AEAVQKLPDD   420
ETLFFGDTGI SKNPVEVIEG WFSNWRSSVM AIVFAILLLV ITVLMVRLCV AFRHFCCQKR   480
HKIYNDLEMN QLRR                                                    494

SEQ ID NO: 271          moltype = AA  length = 494
FEATURE                 Location/Qualifiers
source                  1..494
```

```
                         mol_type = protein
                         organism = Vesicular stomatitis virus
SEQUENCE: 271
KFTIVFPQSQ KGDWKDVPPN YRYCPSSADQ NWHGDLLGVN IRAKMPQVHK AIKADGWMCH   60
AAKWVTTCDY RWYGPQYITH SIHSFIPTKA QCEESIKQTK EGVWINPGFP PKNCGYASVS  120
DAESIIVQAT AHSVMIDEYS GDWLDSQFPT GRCTGSTCET IHNSTLWYAD YQVTGLCDSA  180
LVSTEVTFYS EDGLMTSIGR QNTGYRSNYF PYEKGAAACR MKYCTHEGIR LPSGVWFEMV  240
DKELLESVQM PECPAGLTIS APTQTSVDVS LILDVERMLD YSLCQETWSK VHSGLPISPV  300
DLGYIAPKNP GAGPAFTIVN GTLKYFDTRY LRIDIEGPVL KKMTGKVSGT PTKAELWTEW  360
FPYDDVEIGP NGVLKTPEGY KFPLYMIGHG LLDSDLQKTS QAEVFHHPQI AEAVQKLPDD  420
ETLFFGDTGI SKNPVEVIEG WFSNWRSSVM AIVFAILLLV ITVLMVRLCV AFRHFCCQKR  480
HKIYNDLEMN QLRR                                                   494

SEQ ID NO: 272         moltype = AA  length = 494
FEATURE                Location/Qualifiers
source                 1..494
                       mol_type = protein
                       organism = Vesicular stomatitis virus
SEQUENCE: 272
KFTIVFPQSQ KGDWKDVPPN YRYCPSSADQ NWHGDLLGVN IRAKMPQVHK AIKADGWMCH   60
AAKWVTTCDY RWYGPQYITH SIHSFIPTKA QCEESIKQTK EGVWINPGFP PKNCGYASVS  120
DAESIIVQAT AHSVMIDEYS GDWLDSQFPT GRCTGSTCET IHNSTLWYAD YQVTGLCDSA  180
LVSTEVTFYS EDGLMTSIGR QNTGYRSNYF PYEKGAAACR MKYCTHEGIR LPSGVWFEMV  240
DKELLESVQM PECPAGLTIS APTQTSVDVS LILDVERMLD YSLCQETWSK VHSGLPISPV  300
DLGYIAPKNP GAGPAFTIVN GTLKYFDTRY LRIDIEGPVL KKMTGKVSGT PTKFELWTEW  360
FPYDDVEIGP NGVLKTPEGY KFPLYMIGHG LLDSDLQKTS QAEVFHHPQI AEAVQKLPDD  420
ETLFFGDTGI SKNPVEVIEG WFSNWRSSVM AIVFAILLLV ITVLMVRLCV AFRHFCCQKR  480
HKIYNDLEMN QLRR                                                   494

SEQ ID NO: 273         moltype = AA  length = 494
FEATURE                Location/Qualifiers
source                 1..494
                       mol_type = protein
                       organism = Vesicular stomatitis virus
SEQUENCE: 273
KFTIVFPQSQ KGDWKDVPPN YRYCPSSADQ NWHGDLLGVN IRAKMPQVHK AIKADGWMCH   60
AAKWVTTCDY RWYGPQYITH SIHSFIPTKA QCEESIKQTK EGVWINPGFP PKNCGYASVS  120
DAESIIVQAT AHSVMIDEYS GDWLDSQFPT GRCTGSTCET IHNSTLWYAD YQVTGLCDSA  180
LVSTEVTFYS EDGLMTSIGR QNTGYRSNYF PYEKGAAACR MKYCTHEGIR LPSGVWFEMV  240
DKELLESVQM PECPAGLTIS APTQTSVDVS LILDVERMLD YSLCQETWSK VHSGLPISPV  300
DLGYIAPKNP GAGPAFTIVN GTLKYFDTRY LRIDIEGPVL KKMTGKVSGT PTKGELWTEW  360
FPYDDVEIGP NGVLKTPEGY KFPLYMIGHG LLDSDLQKTS QAEVFHHPQI AEAVQKLPDD  420
ETLFFGDTGI SKNPVEVIEG WFSNWRSSVM AIVFAILLLV ITVLMVRLCV AFRHFCCQKR  480
HKIYNDLEMN QLRR                                                   494

SEQ ID NO: 274         moltype = AA  length = 494
FEATURE                Location/Qualifiers
source                 1..494
                       mol_type = protein
                       organism = Vesicular stomatitis virus
SEQUENCE: 274
KFTIVFPQSQ KGDWKDVPPN YRYCPSSADQ NWHGDLLGVN IRAKMPQVHK AIKADGWMCH   60
AAKWVTTCDY RWYGPQYITH SIHSFIPTKA QCEESIKQTK EGVWINPGFP PKNCGYASVS  120
DAESIIVQAT AHSVMIDEYS GDWLDSQFPT GRCTGSTCET IHNSTLWYAD YQVTGLCDSA  180
LVSTEVTFYS EDGLMTSIGR QNTGYRSNYF PYEKGAAACR MKYCTHEGIR LPSGVWFEMV  240
DKELLESVQM PECPAGLTIS APTQTSVDVS LILDVERMLD YSLCQETWSK VHSGLPISPV  300
DLGYIAPKNP GAGPAFTIVN GTLKYFDTRY LRIDIEGPVL KKMTGKVSGT PTKQELWTEW  360
FPYDDVEIGP NGVLKTPEGY KFPLYMIGHG LLDSDLQKTS QAEVFHHPQI AEAVQKLPDD  420
ETLFFGDTGI SKNPVEVIEG WFSNWRSSVM AIVFAILLLV ITVLMVRLCV AFRHFCCQKR  480
HKIYNDLEMN QLRR                                                   494

SEQ ID NO: 275         moltype = AA  length = 495
FEATURE                Location/Qualifiers
source                 1..495
                       mol_type = protein
                       organism = Vesicular stomatitis virus
SEQUENCE: 275
KFSIVFPQSQ KGNWKNVPSS YHYCPSSSDQ NWHNDLLGIT MKVKMPATHK AIQADGWMCH   60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTERELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 276         moltype = AA  length = 495
FEATURE                Location/Qualifiers
```

```
source                         1..495
                               mol_type = protein
                               organism = Vesicular stomatitis virus
SEQUENCE: 276
KFSIVFPQSQ KGNWKNVPSS YHYCPSSSDQ NWHNDLLGIT MKVKMPFTHK AIQADGWMCH   60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTERELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 277                 moltype = AA  length = 495
FEATURE                        Location/Qualifiers
source                         1..495
                               mol_type = protein
                               organism = Vesicular stomatitis virus
SEQUENCE: 277
KFSIVFPQSQ KGNWKNVPSS YHYCPSSSDQ NWHNDLLGIT MKVKMPGTHK AIQADGWMCH   60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTERELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 278                 moltype = AA  length = 495
FEATURE                        Location/Qualifiers
source                         1..495
                               mol_type = protein
                               organism = Vesicular stomatitis virus
SEQUENCE: 278
KFSIVFPQSQ KGNWKNVPSS YHYCPSSSDQ NWHNDLLGIT MKVKMPQTHK AIQADGWMCH   60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTERELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 279                 moltype = AA  length = 495
FEATURE                        Location/Qualifiers
source                         1..495
                               mol_type = protein
                               organism = Vesicular stomatitis virus
SEQUENCE: 279
KFSIVFPQSQ KGNWKNVPSS YHYCPSSSDQ NWHNDLLGIT MKVKMPKTHK AIQADGWMCH   60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTEAELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 280                 moltype = AA  length = 495
FEATURE                        Location/Qualifiers
source                         1..495
                               mol_type = protein
                               organism = Vesicular stomatitis virus
SEQUENCE: 280
KFSIVFPQSQ KGNWKNVPSS YHYCPSSSDQ NWHNDLLGIT MKVKMPKTHK AIQADGWMCH   60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTEFELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                  495

SEQ ID NO: 281                 moltype = AA  length = 495
```

```
FEATURE                 Location/Qualifiers
source                  1..495
                        mol_type = protein
                        organism = Vesicular stomatitis virus
SEQUENCE: 281
KFSIVFPQSQ KGNWKNVPSS YHYCPSSSDQ NWHNDLLGIT MKVKMPKTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEGELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 282          moltype = AA  length = 495
    FEATURE                 Location/Qualifiers
    source                  1..495
                            mol_type = protein
                            organism = Vesicular stomatitis virus
SEQUENCE: 282
KFSIVFPQSQ KGNWKNVPSS YHYCPSSSDQ NWHNDLLGIT MKVKMPKTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEQELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 283          moltype = AA  length = 495
    FEATURE                 Location/Qualifiers
    source                  1..495
                            mol_type = protein
                            organism = Vesicular stomatitis virus
SEQUENCE: 283
KFSIVFPQSQ KGNWKNVPSS YHYCPSSSDQ NWHNDLLGIT MKVKMPATHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEAELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 284          moltype = AA  length = 495
    FEATURE                 Location/Qualifiers
    source                  1..495
                            mol_type = protein
                            organism = Vesicular stomatitis virus
SEQUENCE: 284
KFSIVFPQSQ KGNWKNVPSS YHYCPSSSDQ NWHNDLLGIT MKVKMPATHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEFELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 285          moltype = AA  length = 495
    FEATURE                 Location/Qualifiers
    source                  1..495
                            mol_type = protein
                            organism = Vesicular stomatitis virus
SEQUENCE: 285
KFSIVFPQSQ KGNWKNVPSS YHYCPSSSDQ NWHNDLLGIT MKVKMPATHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEGELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495
```

```
SEQ ID NO: 286          moltype = AA   length = 495
FEATURE                 Location/Qualifiers
source                  1..495
                        mol_type = protein
                        organism = Vesicular stomatitis virus
SEQUENCE: 286
KFSIVFPQSQ KGNWKNVPSS YHYCPSSSDQ NWHNDLLGIT MKVKMPATHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEQELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 287          moltype = AA   length = 495
FEATURE                 Location/Qualifiers
source                  1..495
                        mol_type = protein
                        organism = Vesicular stomatitis virus
SEQUENCE: 287
KFSIVFPQSQ KGNWKNVPSS YHYCPSSSDQ NWHNDLLGIT MKVKMPFTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEAELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 288          moltype = AA   length = 495
FEATURE                 Location/Qualifiers
source                  1..495
                        mol_type = protein
                        organism = Vesicular stomatitis virus
SEQUENCE: 288
KFSIVFPQSQ KGNWKNVPSS YHYCPSSSDQ NWHNDLLGIT MKVKMPFTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEFELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 289          moltype = AA   length = 495
FEATURE                 Location/Qualifiers
source                  1..495
                        mol_type = protein
                        organism = Vesicular stomatitis virus
SEQUENCE: 289
KFSIVFPQSQ KGNWKNVPSS YHYCPSSSDQ NWHNDLLGIT MKVKMPFTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEGELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495

SEQ ID NO: 290          moltype = AA   length = 495
FEATURE                 Location/Qualifiers
source                  1..495
                        mol_type = protein
                        organism = Vesicular stomatitis virus
SEQUENCE: 290
KFSIVFPQSQ KGNWKNVPSS YHYCPSSSDQ NWHNDLLGIT MKVKMPFTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEQELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                   495
```

```
SEQ ID NO: 291          moltype = AA   length = 495
FEATURE                 Location/Qualifiers
source                  1..495
                        mol_type = protein
                        organism = Vesicular stomatitis virus
SEQUENCE: 291
KFSIVFPQSQ KGNWKNVPSS YHYCPSSSDQ NWHNDLLGIT MKVKMPGTHK AIQADGWMCH      60
AAKWITTCDF RWYGPKYITH SIHSIQPTSE QCKESIKQTK QGTWMSPGFP PQNCGYATVT     120
DSVAVVVQAT PHHVLVDEYT GEWIDSQFPN GKCETEECET VHNSTVWYSD YKVTGLCDAT     180
LVDTEITFFS EDGKKESIGK PNTGYRSNYF AYEKGDKVCK MNYCKHAGVR LPSGVWFEFV     240
DQDVYAAAKL PECPVGATIS APTQTSVDVS LILDVERILD YSLCQETWSK IRSKQPVSPV     300
DLSYLAPKNP GTGPAFTIIN GTLKYFETRY IRIDIDNPII SKMVGKISGS QTEAELWTEW     360
FPYEGVEIGP NGILKTPTGY KFPLFMIGHG MLDSDLHKTS QAEVFEHPHL AEAPKQLPEE     420
ETLFFGDTGI SKNPVELIEG WFSSWKSTVV TFFFAIGVFI LLYVVARIVI AVRYRYQGSN     480
NKRIYNDIEM SRFRK                                                     495

SEQ ID NO: 292          moltype = AA   length = 495
FEATURE                 Location/Qualifiers
source                  1..495
                        mol_type = protein
                        organism = Vesicular stomatitis virus
SEQUENCE: 292
KFSIVFPQSQ KGNWKNVPSS YHYCPSSSDQ NWHNDLLGIT MKVKMPGTHK AIQADGWMCH      60
AAKWITTCDF RWYGPKYITH SIHSIQPTSE QCKESIKQTK QGTWMSPGFP PQNCGYATVT     120
DSVAVVVQAT PHHVLVDEYT GEWIDSQFPN GKCETEECET VHNSTVWYSD YKVTGLCDAT     180
LVDTEITFFS EDGKKESIGK PNTGYRSNYF AYEKGDKVCK MNYCKHAGVR LPSGVWFEFV     240
DQDVYAAAKL PECPVGATIS APTQTSVDVS LILDVERILD YSLCQETWSK IRSKQPVSPV     300
DLSYLAPKNP GTGPAFTIIN GTLKYFETRY IRIDIDNPII SKMVGKISGS QTEFELWTEW     360
FPYEGVEIGP NGILKTPTGY KFPLFMIGHG MLDSDLHKTS QAEVFEHPHL AEAPKQLPEE     420
ETLFFGDTGI SKNPVELIEG WFSSWKSTVV TFFFAIGVFI LLYVVARIVI AVRYRYQGSN     480
NKRIYNDIEM SRFRK                                                     495

SEQ ID NO: 293          moltype = AA   length = 495
FEATURE                 Location/Qualifiers
source                  1..495
                        mol_type = protein
                        organism = Vesicular stomatitis virus
SEQUENCE: 293
KFSIVFPQSQ KGNWKNVPSS YHYCPSSSDQ NWHNDLLGIT MKVKMPGTHK AIQADGWMCH      60
AAKWITTCDF RWYGPKYITH SIHSIQPTSE QCKESIKQTK QGTWMSPGFP PQNCGYATVT     120
DSVAVVVQAT PHHVLVDEYT GEWIDSQFPN GKCETEECET VHNSTVWYSD YKVTGLCDAT     180
LVDTEITFFS EDGKKESIGK PNTGYRSNYF AYEKGDKVCK MNYCKHAGVR LPSGVWFEFV     240
DQDVYAAAKL PECPVGATIS APTQTSVDVS LILDVERILD YSLCQETWSK IRSKQPVSPV     300
DLSYLAPKNP GTGPAFTIIN GTLKYFETRY IRIDIDNPII SKMVGKISGS QTEGELWTEW     360
FPYEGVEIGP NGILKTPTGY KFPLFMIGHG MLDSDLHKTS QAEVFEHPHL AEAPKQLPEE     420
ETLFFGDTGI SKNPVELIEG WFSSWKSTVV TFFFAIGVFI LLYVVARIVI AVRYRYQGSN     480
NKRIYNDIEM SRFRK                                                     495

SEQ ID NO: 294          moltype = AA   length = 495
FEATURE                 Location/Qualifiers
source                  1..495
                        mol_type = protein
                        organism = Vesicular stomatitis virus
SEQUENCE: 294
KFSIVFPQSQ KGNWKNVPSS YHYCPSSSDQ NWHNDLLGIT MKVKMPGTHK AIQADGWMCH      60
AAKWITTCDF RWYGPKYITH SIHSIQPTSE QCKESIKQTK QGTWMSPGFP PQNCGYATVT     120
DSVAVVVQAT PHHVLVDEYT GEWIDSQFPN GKCETEECET VHNSTVWYSD YKVTGLCDAT     180
LVDTEITFFS EDGKKESIGK PNTGYRSNYF AYEKGDKVCK MNYCKHAGVR LPSGVWFEFV     240
DQDVYAAAKL PECPVGATIS APTQTSVDVS LILDVERILD YSLCQETWSK IRSKQPVSPV     300
DLSYLAPKNP GTGPAFTIIN GTLKYFETRY IRIDIDNPII SKMVGKISGS QTEQELWTEW     360
FPYEGVEIGP NGILKTPTGY KFPLFMIGHG MLDSDLHKTS QAEVFEHPHL AEAPKQLPEE     420
ETLFFGDTGI SKNPVELIEG WFSSWKSTVV TFFFAIGVFI LLYVVARIVI AVRYRYQGSN     480
NKRIYNDIEM SRFRK                                                     495

SEQ ID NO: 295          moltype = AA   length = 495
FEATURE                 Location/Qualifiers
source                  1..495
                        mol_type = protein
                        organism = Vesicular stomatitis virus
SEQUENCE: 295
KFSIVFPQSQ KGNWKNVPSS YHYCPSSSDQ NWHNDLLGIT MKVKMPQTHK AIQADGWMCH      60
AAKWITTCDF RWYGPKYITH SIHSIQPTSE QCKESIKQTK QGTWMSPGFP PQNCGYATVT     120
DSVAVVVQAT PHHVLVDEYT GEWIDSQFPN GKCETEECET VHNSTVWYSD YKVTGLCDAT     180
LVDTEITFFS EDGKKESIGK PNTGYRSNYF AYEKGDKVCK MNYCKHAGVR LPSGVWFEFV     240
DQDVYAAAKL PECPVGATIS APTQTSVDVS LILDVERILD YSLCQETWSK IRSKQPVSPV     300
DLSYLAPKNP GTGPAFTIIN GTLKYFETRY IRIDIDNPII SKMVGKISGS QTEAELWTEW     360
FPYEGVEIGP NGILKTPTGY KFPLFMIGHG MLDSDLHKTS QAEVFEHPHL AEAPKQLPEE     420
ETLFFGDTGI SKNPVELIEG WFSSWKSTVV TFFFAIGVFI LLYVVARIVI AVRYRYQGSN     480
```

```
NKRIYNDIEM SRFRK                                                             495

SEQ ID NO: 296          moltype = AA  length = 495
FEATURE                 Location/Qualifiers
source                  1..495
                        mol_type = protein
                        organism = Vesicular stomatitis virus
SEQUENCE: 296
KFSIVFPQSQ KGNWKNVPSS YHYCPSSSDQ NWHNDLLGIT MKVKMPQTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEFELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                    495

SEQ ID NO: 297          moltype = AA  length = 495
FEATURE                 Location/Qualifiers
source                  1..495
                        mol_type = protein
                        organism = Vesicular stomatitis virus
SEQUENCE: 297
KFSIVFPQSQ KGNWKNVPSS YHYCPSSSDQ NWHNDLLGIT MKVKMPQTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEGELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                    495

SEQ ID NO: 298          moltype = AA  length = 495
FEATURE                 Location/Qualifiers
source                  1..495
                        mol_type = protein
                        organism = Vesicular stomatitis virus
SEQUENCE: 298
KFSIVFPQSQ KGNWKNVPSS YHYCPSSSDQ NWHNDLLGIT MKVKMPQTHK AIQADGWMCH    60
AAKWITTCDF RWYGPKYITH SIHSIQPTSE QCKESIKQTK QGTWMSPGFP PQNCGYATVT   120
DSVAVVVQAT PHHVLVDEYT GEWIDSQFPN GKCETEECET VHNSTVWYSD YKVTGLCDAT   180
LVDTEITFFS EDGKKESIGK PNTGYRSNYF AYEKGDKVCK MNYCKHAGVR LPSGVWFEFV   240
DQDVYAAAKL PECPVGATIS APTQTSVDVS LILDVERILD YSLCQETWSK IRSKQPVSPV   300
DLSYLAPKNP GTGPAFTIIN GTLKYFETRY IRIDIDNPII SKMVGKISGS QTEQELWTEW   360
FPYEGVEIGP NGILKTPTGY KFPLFMIGHG MLDSDLHKTS QAEVFEHPHL AEAPKQLPEE   420
ETLFFGDTGI SKNPVELIEG WFSSWKSTVV TFFFAIGVFI LLYVVARIVI AVRYRYQGSN   480
NKRIYNDIEM SRFRK                                                    495

SEQ ID NO: 299          moltype = AA  length = 496
FEATURE                 Location/Qualifiers
source                  1..496
                        mol_type = protein
                        organism = Vesicular stomatitis virus
SEQUENCE: 299
KFTIVFPHNQ KGNWKNVPAN YQYCPSSSDL NWHNGLIGTS LQVKMPASHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                   496

SEQ ID NO: 300          moltype = AA  length = 496
FEATURE                 Location/Qualifiers
source                  1..496
                        mol_type = protein
                        organism = Vesicular stomatitis virus
SEQUENCE: 300
KFTIVFPHNQ KGNWKNVPAN YQYCPSSSDL NWHNGLIGTS LQVKMPFSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
```

```
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 301           moltype = AA  length = 496
FEATURE                  Location/Qualifiers
source                   1..496
                         mol_type = protein
                         organism = Vesicular stomatitis virus
SEQUENCE: 301
KFTIVFPHNQ KGNWKNVPAN YQYCPSSSDL NWHNGLIGTS LQVKMPGSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 302           moltype = AA  length = 496
FEATURE                  Location/Qualifiers
source                   1..496
                         mol_type = protein
                         organism = Vesicular stomatitis virus
SEQUENCE: 302
KFTIVFPHNQ KGNWKNVPAN YQYCPSSSDL NWHNGLIGTS LQVKMPQSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTERELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 303           moltype = AA  length = 496
FEATURE                  Location/Qualifiers
source                   1..496
                         mol_type = protein
                         organism = Vesicular stomatitis virus
SEQUENCE: 303
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEAELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 304           moltype = AA  length = 496
FEATURE                  Location/Qualifiers
source                   1..496
                         mol_type = protein
                         organism = Vesicular stomatitis virus
SEQUENCE: 304
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEFELWTDW   360
YPYEDVEIGP NGVLKTATGY KFPLYMIGHG MLDSDLHISS KAQVFEHPHI QDAASQLPDD   420
ETLFFGDTGL SKNPIELVEG WFSGWKSTIA SFFFIIGLVI GLYLVLRIGI ALCIKCRVQE   480
KRPKIYTDVE MNRLDR                                                  496

SEQ ID NO: 305           moltype = AA  length = 496
FEATURE                  Location/Qualifiers
source                   1..496
                         mol_type = protein
                         organism = Vesicular stomatitis virus
SEQUENCE: 305
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT   120
DAEAVIVKAT PHQVLVDEYT GEWVDSQFPT GKCNKDICPT VHNSTTWHSD YKVTGLCDAN   180
LISMDITFFS EDGKLTSLGK EGTGFRSNYF AYENGDKACR MQYCKHWGVR LPSGVWFEMA   240
DKDIYNDAKF PDCPEGSSIA APSQTSVDVS LIQDVERILD YSLCQETWSK IRAHLPISPV   300
DLSYLSPKNP GTGPAFTIIN GTLKYFETRY IRVDIAGPII PQMRGVISGT TTEGELWTDW   360
```

```
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 306          moltype = AA  length = 496
FEATURE                 Location/Qualifiers
source                  1..496
                        mol_type = protein
                        organism = Vesicular stomatitis virus
SEQUENCE: 306
KFTIVFPHNQ KGNWKNVPAN YQYCPSSSDL NWHNGLIGTS LQVKMPKSHK AIQADGWMCH    60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEQELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 307          moltype = AA  length = 496
FEATURE                 Location/Qualifiers
source                  1..496
                        mol_type = protein
                        organism = Vesicular stomatitis virus
SEQUENCE: 307
KFTIVFPHNQ KGNWKNVPAN YQYCPSSSDL NWHNGLIGTS LQVKMPASHK AIQADGWMCH    60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEAELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 308          moltype = AA  length = 496
FEATURE                 Location/Qualifiers
source                  1..496
                        mol_type = protein
                        organism = Vesicular stomatitis virus
SEQUENCE: 308
KFTIVFPHNQ KGNWKNVPAN YQYCPSSSDL NWHNGLIGTS LQVKMPASHK AIQADGWMCH    60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEFELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 309          moltype = AA  length = 496
FEATURE                 Location/Qualifiers
source                  1..496
                        mol_type = protein
                        organism = Vesicular stomatitis virus
SEQUENCE: 309
KFTIVFPHNQ KGNWKNVPAN YQYCPSSSDL NWHNGLIGTS LQVKMPASHK AIQADGWMCH    60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEGELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 310          moltype = AA  length = 496
FEATURE                 Location/Qualifiers
source                  1..496
                        mol_type = protein
                        organism = Vesicular stomatitis virus
SEQUENCE: 310
KFTIVFPHNQ KGNWKNVPAN YQYCPSSSDL NWHNGLIGTS LQVKMPASHK AIQADGWMCH    60
AAKWVTTCDF RWYGPKYVTH SIKSMIPTVD QCKESIAQTK QGTWLNPGFP PQSCGYASVT    120
DAEAVIVKAT PHQVLVDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
```

```
DLSYLSPKNP GTGPAFTIIN GTLKYFETRY IRVDIAGPII PQMRGVISGT TTEQELWTDW  360
YPYEDVEIGP NGVLKTATGY KFPLYMIGHG MLDSDLHISS KAQVFEHPHI QDAASQLPDD  420
ETLFFGDTGL SKNPIELVEG WFSGWKSTIA SFFFIIGLVI GLYLVLRIGI ALCIKCRVQE  480
KRPKIYTDVE MNRLDR                                                 496

SEQ ID NO: 311          moltype = AA   length = 496
FEATURE                 Location/Qualifiers
source                  1..496
                        mol_type = protein
                        organism = Vesicular stomatitis virus
SEQUENCE: 311
KFTIVFPHNQ KGNWKNVPAN YQYCPSSSDL NWHNGLIGTS LQVKMPFSHK AIQADGWMCH  60
AAKWVTTCDF RWYGPKYVTH SIKSMIPTVD QCKESIAQTK QGTWLNPGFP PQSCGYASVT  120
DAEAVIVKAT PHQVLVDEYT GEWVDSQFPT GKCNKDICPT VHNSTTWHSD YKVTGLCDAN  180
LISMDITFFS EDGKLTSLGK EGTGFRSNYF AYENGDKACR MQYCKHWGVR LPSGVWFEMA  240
DKDIYNDAKF PDCPEGSSIA APSQTSVDVS LIQDVERILD YSLCQETWSK IRAHLPISPV  300
DLSYLSPKNP GTGPAFTIIN GTLKYFETRY IRVDIAGPII PQMRGVISGT TTEAELWTDW  360
YPYEDVEIGP NGVLKTATGY KFPLYMIGHG MLDSDLHISS KAQVFEHPHI QDAASQLPDD  420
ETLFFGDTGL SKNPIELVEG WFSGWKSTIA SFFFIIGLVI GLYLVLRIGI ALCIKCRVQE  480
KRPKIYTDVE MNRLDR                                                 496

SEQ ID NO: 312          moltype = AA   length = 496
FEATURE                 Location/Qualifiers
source                  1..496
                        mol_type = protein
                        organism = Vesicular stomatitis virus
SEQUENCE: 312
KFTIVFPHNQ KGNWKNVPAN YQYCPSSSDL NWHNGLIGTS LQVKMPFSHK AIQADGWMCH  60
AAKWVTTCDF RWYGPKYVTH SIKSMIPTVD QCKESIAQTK QGTWLNPGFP PQSCGYASVT  120
DAEAVIVKAT PHQVLVDEYT GEWVDSQFPT GKCNKDICPT VHNSTTWHSD YKVTGLCDAN  180
LISMDITFFS EDGKLTSLGK EGTGFRSNYF AYENGDKACR MQYCKHWGVR LPSGVWFEMA  240
DKDIYNDAKF PDCPEGSSIA APSQTSVDVS LIQDVERILD YSLCQETWSK IRAHLPISPV  300
DLSYLSPKNP GTGPAFTIIN GTLKYFETRY IRVDIAGPII PQMRGVISGT TTEFELWTDW  360
YPYEDVEIGP NGVLKTATGY KFPLYMIGHG MLDSDLHISS KAQVFEHPHI QDAASQLPDD  420
ETLFFGDTGL SKNPIELVEG WFSGWKSTIA SFFFIIGLVI GLYLVLRIGI ALCIKCRVQE  480
KRPKIYTDVE MNRLDR                                                 496

SEQ ID NO: 313          moltype = AA   length = 496
FEATURE                 Location/Qualifiers
source                  1..496
                        mol_type = protein
                        organism = Vesicular stomatitis virus
SEQUENCE: 313
KFTIVFPHNQ KGNWKNVPAN YQYCPSSSDL NWHNGLIGTS LQVKMPFSHK AIQADGWMCH  60
AAKWVTTCDF RWYGPKYVTH SIKSMIPTVD QCKESIAQTK QGTWLNPGFP PQSCGYASVT  120
DAEAVIVKAT PHQVLVDEYT GEWVDSQFPT GKCNKDICPT VHNSTTWHSD YKVTGLCDAN  180
LISMDITFFS EDGKLTSLGK EGTGFRSNYF AYENGDKACR MQYCKHWGVR LPSGVWFEMA  240
DKDIYNDAKF PDCPEGSSIA APSQTSVDVS LIQDVERILD YSLCQETWSK IRAHLPISPV  300
DLSYLSPKNP GTGPAFTIIN GTLKYFETRY IRVDIAGPII PQMRGVISGT TTEGELWTDW  360
YPYEDVEIGP NGVLKTATGY KFPLYMIGHG MLDSDLHISS KAQVFEHPHI QDAASQLPDD  420
ETLFFGDTGL SKNPIELVEG WFSGWKSTIA SFFFIIGLVI GLYLVLRIGI ALCIKCRVQE  480
KRPKIYTDVE MNRLDR                                                 496

SEQ ID NO: 314          moltype = AA   length = 496
FEATURE                 Location/Qualifiers
source                  1..496
                        mol_type = protein
                        organism = Vesicular stomatitis virus
SEQUENCE: 314
KFTIVFPHNQ KGNWKNVPAN YQYCPSSSDL NWHNGLIGTS LQVKMPFSHK AIQADGWMCH  60
AAKWVTTCDF RWYGPKYVTH SIKSMIPTVD QCKESIAQTK QGTWLNPGFP PQSCGYASVT  120
DAEAVIVKAT PHQVLVDEYT GEWVDSQFPT GKCNKDICPT VHNSTTWHSD YKVTGLCDAN  180
LISMDITFFS EDGKLTSLGK EGTGFRSNYF AYENGDKACR MQYCKHWGVR LPSGVWFEMA  240
DKDIYNDAKF PDCPEGSSIA APSQTSVDVS LIQDVERILD YSLCQETWSK IRAHLPISPV  300
DLSYLSPKNP GTGPAFTIIN GTLKYFETRY IRVDIAGPII PQMRGVISGT TTEQELWTDW  360
YPYEDVEIGP NGVLKTATGY KFPLYMIGHG MLDSDLHISS KAQVFEHPHI QDAASQLPDD  420
ETLFFGDTGL SKNPIELVEG WFSGWKSTIA SFFFIIGLVI GLYLVLRIGI ALCIKCRVQE  480
KRPKIYTDVE MNRLDR                                                 496

SEQ ID NO: 315          moltype = AA   length = 496
FEATURE                 Location/Qualifiers
source                  1..496
                        mol_type = protein
                        organism = Vesicular stomatitis virus
SEQUENCE: 315
KFTIVFPHNQ KGNWKNVPAN YQYCPSSSDL NWHNGLIGTS LQVKMPGSHK AIQADGWMCH  60
AAKWVTTCDF RWYGPKYVTH SIKSMIPTVD QCKESIAQTK QGTWLNPGFP PQSCGYASVT  120
DAEAVIVKAT PHQVLVDEYT GEWVDSQFPT GKCNKDICPT VHNSTTWHSD YKVTGLCDAN  180
LISMDITFFS EDGKLTSLGK EGTGFRSNYF AYENGDKACR MQYCKHWGVR LPSGVWFEMA  240
```

```
DKDIYNDAKF PDCPEGSSIA APSQTSVDVS LIQDVERILD YSLCQETWSK IRAHLPISPV     300
DLSYLSPKNP GTGPAFTIIN GTLKYFETRY IRVDIAGPII PQMRGVISGT TTEAELWTDW     360
YPYEDVEIGP NGVLKTATGY KFPLYMIGHG MLDSDLHISS KAQVFEHPHI QDAASQLPDD     420
ETLFFGDTGL SKNPIELVEG WFSGWKSTIA SFFFIIGLVI GLYLVLRIGI ALCIKCRVQE     480
KRPKIYTDVE MNRLDR                                                    496

SEQ ID NO: 316          moltype = AA  length = 496
FEATURE                 Location/Qualifiers
source                  1..496
                        mol_type = protein
                        organism = Vesicular stomatitis virus
SEQUENCE: 316
KFTIVFPHNQ KGNWKNVPAN YQYCPSSSDL NWHNGLIGTS LQVKMPGSHK AIQADGWMCH      60
AAKWVTTCDF RWYGPKYVTH SIKSMIPTVD QCKESIAQTK QGTWLNPGFP PQSCGYASVT     120
DAEAVIVKAT PHQVLVDEYT GEWVDSQFPT GKCNKDICPT VHNSTTWHSD YKVTGLCDAN     180
LISMDITFFS EDGKLTSLGK EGTGFRSNYF AYENGDKACR MQYCKHWGVR LPSGVWFEMA     240
DKDIYNDAKF PDCPEGSSIA APSQTSVDVS LIQDVERILD YSLCQETWSK IRAHLPISPV     300
DLSYLSPKNP GTGPAFTIIN GTLKYFETRY IRVDIAGPII PQMRGVISGT TTEFELWTDW     360
YPYEDVEIGP NGVLKTATGY KFPLYMIGHG MLDSDLHISS KAQVFEHPHI QDAASQLPDD     420
ETLFFGDTGL SKNPIELVEG WFSGWKSTIA SFFFIIGLVI GLYLVLRIGI ALCIKCRVQE     480
KRPKIYTDVE MNRLDR                                                    496

SEQ ID NO: 317          moltype = AA  length = 496
FEATURE                 Location/Qualifiers
source                  1..496
                        mol_type = protein
                        organism = Vesicular stomatitis virus
SEQUENCE: 317
KFTIVFPHNQ KGNWKNVPAN YQYCPSSSDL NWHNGLIGTS LQVKMPGSHK AIQADGWMCH      60
AAKWVTTCDF RWYGPKYVTH SIKSMIPTVD QCKESIAQTK QGTWLNPGFP PQSCGYASVT     120
DAEAVIVKAT PHQVLVDEYT GEWVDSQFPT GKCNKDICPT VHNSTTWHSD YKVTGLCDAN     180
LISMDITFFS EDGKLTSLGK EGTGFRSNYF AYENGDKACR MQYCKHWGVR LPSGVWFEMA     240
DKDIYNDAKF PDCPEGSSIA APSQTSVDVS LIQDVERILD YSLCQETWSK IRAHLPISPV     300
DLSYLSPKNP GTGPAFTIIN GTLKYFETRY IRVDIAGPII PQMRGVISGT TTEGELWTDW     360
YPYEDVEIGP NGVLKTATGY KFPLYMIGHG MLDSDLHISS KAQVFEHPHI QDAASQLPDD     420
ETLFFGDTGL SKNPIELVEG WFSGWKSTIA SFFFIIGLVI GLYLVLRIGI ALCIKCRVQE     480
KRPKIYTDVE MNRLDR                                                    496

SEQ ID NO: 318          moltype = AA  length = 496
FEATURE                 Location/Qualifiers
source                  1..496
                        mol_type = protein
                        organism = Vesicular stomatitis virus
SEQUENCE: 318
KFTIVFPHNQ KGNWKNVPAN YQYCPSSSDL NWHNGLIGTS LQVKMPGSHK AIQADGWMCH      60
AAKWVTTCDF RWYGPKYVTH SIKSMIPTVD QCKESIAQTK QGTWLNPGFP PQSCGYASVT     120
DAEAVIVKAT PHQVLVDEYT GEWVDSQFPT GKCNKDICPT VHNSTTWHSD YKVTGLCDAN     180
LISMDITFFS EDGKLTSLGK EGTGFRSNYF AYENGDKACR MQYCKHWGVR LPSGVWFEMA     240
DKDIYNDAKF PDCPEGSSIA APSQTSVDVS LIQDVERILD YSLCQETWSK IRAHLPISPV     300
DLSYLSPKNP GTGPAFTIIN GTLKYFETRY IRVDIAGPII PQMRGVISGT TTEQELWTDW     360
YPYEDVEIGP NGVLKTATGY KFPLYMIGHG MLDSDLHISS KAQVFEHPHI QDAASQLPDD     420
ETLFFGDTGL SKNPIELVEG WFSGWKSTIA SFFFIIGLVI GLYLVLRIGI ALCIKCRVQE     480
KRPKIYTDVE MNRLDR                                                    496

SEQ ID NO: 319          moltype = AA  length = 496
FEATURE                 Location/Qualifiers
source                  1..496
                        mol_type = protein
                        organism = Vesicular stomatitis virus
SEQUENCE: 319
KFTIVFPHNQ KGNWKNVPAN YQYCPSSSDL NWHNGLIGTS LQVKMPQSHK AIQADGWMCH      60
AAKWVTTCDF RWYGPKYVTH SIKSMIPTVD QCKESIAQTK QGTWLNPGFP PQSCGYASVT     120
DAEAVIVKAT PHQVLVDEYT GEWVDSQFPT GKCNKDICPT VHNSTTWHSD YKVTGLCDAN     180
LISMDITFFS EDGKLTSLGK EGTGFRSNYF AYENGDKACR MQYCKHWGVR LPSGVWFEMA     240
DKDIYNDAKF PDCPEGSSIA APSQTSVDVS LIQDVERILD YSLCQETWSK IRAHLPISPV     300
DLSYLSPKNP GTGPAFTIIN GTLKYFETRY IRVDIAGPII PQMRGVISGT TTEAELWTDW     360
YPYEDVEIGP NGVLKTATGY KFPLYMIGHG MLDSDLHISS KAQVFEHPHI QDAASQLPDD     420
ETLFFGDTGL SKNPIELVEG WFSGWKSTIA SFFFIIGLVI GLYLVLRIGI ALCIKCRVQE     480
KRPKIYTDVE MNRLDR                                                    496

SEQ ID NO: 320          moltype = AA  length = 496
FEATURE                 Location/Qualifiers
source                  1..496
                        mol_type = protein
                        organism = Vesicular stomatitis virus
SEQUENCE: 320
KFTIVFPHNQ KGNWKNVPAN YQYCPSSSDL NWHNGLIGTS LQVKMPQSHK AIQADGWMCH      60
AAKWVTTCDF RWYGPKYVTH SIKSMIPTVD QCKESIAQTK QGTWLNPGFP PQSCGYASVT     120
DAEAVIVKAT PHQVLVDEYT GEWVDSQFPT GKCNKDICPT VHNSTTWHSD YKVTGLCDAN     180
```

```
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEFELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 321          moltype = AA   length = 496
FEATURE                 Location/Qualifiers
source                  1..496
                        mol_type = protein
                        organism = Vesicular stomatitis virus
SEQUENCE: 321
KFTIVFPHNQ KGNWKNVPAN YQYCPSSSDL NWHNGLIGTS LQVKMPQSHK AIQADGWMCH     60
AAKWVTTCDF RWYGPKYVTH SIKSMIPTVD QCKESIAQTK QGTWLNPGFP PQSCGYASVT    120
DAEAVIVKAT PHQVLDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEGELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 322          moltype = AA   length = 496
FEATURE                 Location/Qualifiers
source                  1..496
                        mol_type = protein
                        organism = Vesicular stomatitis virus
SEQUENCE: 322
KFTIVFPHNQ KGNWKNVPAN YQYCPSSSDL NWHNGLIGTS LQVKMPQSHK AIQADGWMCH     60
AAKWVTTCDF RWYGPKYVTH SIKSMIPTVD QCKESIAQTK QGTWLNPGFP PQSCGYASVT    120
DAEAVIVKAT PHQVLDEYT GEWVDSQFPT GKCNKDICPT VHNSTTWHSD YKVTGLCDAN    180
LISMDITFFS EDGKLTSLGK EGTGFRSNYF AYENGDKACR MQYCKHWGVR LPSGVWFEMA    240
DKDIYNDAKF PDCPEGSSIA APSQTSVDVS LIQDVERILD YSLCQETWSK IRAHLPISPV    300
DLSYLSPKNP GTGPAFTIIN GTLKYFETRY IRVDIAGPII PQMRGVISGT TTEQELWTDW    360
YPYEDVEIGP NGVLKTATGY KFPLYMIGHG MLDSDLHISS KAQVFEHPHI QDAASQLPDD    420
ETLFFGDTGL SKNPIELVEG WFSGWKSTIA SFFFIIGLVI GLYLVLRIGI ALCIKCRVQE    480
KRPKIYTDVE MNRLDR                                                   496

SEQ ID NO: 323          moltype = DNA  length = 32
FEATURE                 Location/Qualifiers
misc_feature            1..32
                        note = CR2 of human LDL-R
misc_feature            15
                        note = n is a, c, g, or t
misc_feature            27
                        note = n is a, c, g, or t
source                  1..32
                        mol_type = other DNA
                        organism = synthetic construct
SEQUENCE: 323
svtcksgdsc ggrvnrcwrc dgvdcdngsd gc                                  32

SEQ ID NO: 324          moltype = AA   length = 39
FEATURE                 Location/Qualifiers
REGION                  1..39
                        note = CR3 of human LDL-R
source                  1..39
                        mol_type = protein
                        organism = synthetic construct
SEQUENCE: 324
PKTCSQDEFR CHDGKCISRQ FVCDSDRDCL DGSDEASCP                           39

SEQ ID NO: 325          moltype = AA   length = 42
FEATURE                 Location/Qualifiers
REGION                  1..42
                        note = CR1 of human LDL-R
source                  1..42
                        mol_type = protein
                        organism = synthetic construct
SEQUENCE: 325
VGDRCERNEF QCQDGKCISY KWVCDGSAEC QDGSDESQET CL                       42

SEQ ID NO: 326          moltype = AA   length = 41
FEATURE                 Location/Qualifiers
REGION                  1..41
                        note = CR2 of human LDL-R
source                  1..41
                        mol_type = protein
```

```
                        organism = synthetic construct
SEQUENCE: 326
SVTCKSGDFS CGGRVNRCIP QFWRCDGQVD CDNGSDEQGC P                  41

SEQ ID NO: 327          moltype = AA  length = 39
FEATURE                 Location/Qualifiers
REGION                  1..39
                        note = CR3 of human LDL-R
source                  1..39
                        mol_type = protein
                        organism = synthetic construct
SEQUENCE: 327
PKTCSQDEFR CHDGKCISRQ FVCDSDRDCL DGSDEASCP                     39

SEQ ID NO: 328          moltype = AA  length = 41
FEATURE                 Location/Qualifiers
REGION                  1..41
                        note = CR4 of human LDL-R
source                  1..41
                        mol_type = protein
                        organism = synthetic construct
SEQUENCE: 328
VLTCGPASFQ CNSSTCIPKL WACDNDPDCE DGSDEWPQRC R                  41

SEQ ID NO: 329          moltype = AA  length = 40
FEATURE                 Location/Qualifiers
REGION                  1..40
                        note = CR5 of human LDL-R
source                  1..40
                        mol_type = protein
                        organism = synthetic construct
SEQUENCE: 329
DSSPCSAFEF HCLSGECIHS SWRCDGGPDC KDKSDEENCA                    40

SEQ ID NO: 330          moltype = AA  length = 39
FEATURE                 Location/Qualifiers
REGION                  1..39
                        note = CR6 of human LDL-R
source                  1..39
                        mol_type = protein
                        organism = synthetic construct
SEQUENCE: 330
VATCRPDEFQ CSDGNCIHGS RQCDREYDCK DMSDEVGCV                     39

SEQ ID NO: 331          moltype = AA  length = 41
FEATURE                 Location/Qualifiers
REGION                  1..41
                        note = CR7 of human LDL-R
source                  1..41
                        mol_type = protein
                        organism = synthetic construct
SEQUENCE: 331
VTLCEGPNKF KCHSGECITL DKVCNMARDC RDWSDEPIKE C                  41

SEQ ID NO: 332          moltype = DNA  length = 41
FEATURE                 Location/Qualifiers
misc_feature            1..41
                        note = primer sense
source                  1..41
                        mol_type = other DNA
                        organism = synthetic construct
SEQUENCE: 332
tctcatcatt ttggcaaaga tgaagtgcct tttgtactta g                  41

SEQ ID NO: 333          moltype = DNA  length = 36
FEATURE                 Location/Qualifiers
misc_feature            1..36
                        note = primer antisense1
source                  1..36
                        mol_type = other DNA
                        organism = synthetic construct
SEQUENCE: 333
ttgctcacca tgcaattcac cccaatgaat aaaaag                        36

SEQ ID NO: 334          moltype = DNA  length = 31
FEATURE                 Location/Qualifiers
misc_feature            1..31
                        note = primer antisense351
source                  1..31
```

```
                              mol_type = other DNA
                              organism = synthetic construct
SEQUENCE: 334
gctcaccata gttccactga tcattccgac c                              31

SEQ ID NO: 335                moltype = DNA   length = 31
FEATURE                       Location/Qualifiers
misc_feature                  1..31
                              note = primer sense
source                        1..31
                              mol_type = other DNA
                              organism = synthetic construct
SEQUENCE: 335
cattggggtg aattgcatgg tgagcaaggg c                              31

SEQ ID NO: 336                moltype = DNA   length = 31
FEATURE                       Location/Qualifiers
misc_feature                  1..31
                              note = primer sense
source                        1..31
                              mol_type = other DNA
                              organism = synthetic construct
SEQUENCE: 336
aatgatcagt ggaactatgg tgagcaaggg c                              31

SEQ ID NO: 337                moltype = DNA   length = 31
FEATURE                       Location/Qualifiers
misc_feature                  1..31
                              note = primer antisense1
source                        1..31
                              mol_type = other DNA
                              organism = synthetic construct
SEQUENCE: 337
cattggggtg aattgcatgg tgagcaaggg c                              31

SEQ ID NO: 338                moltype = DNA   length = 32
FEATURE                       Location/Qualifiers
misc_feature                  1..32
                              note = primer antisense351
source                        1..32
                              mol_type = other DNA
                              organism = synthetic construct
SEQUENCE: 338
gttcccttc tgtggtcttg tacagctcgt cc                              32

SEQ ID NO: 339                moltype = DNA   length = 37
FEATURE                       Location/Qualifiers
misc_feature                  1..37
                              note = primer sense1
source                        1..37
                              mol_type = other DNA
                              organism = synthetic construct
SEQUENCE: 339
gagctgtaca agaagttcac catagttttt ccacaca                        37

SEQ ID NO: 340                moltype = DNA   length = 28
FEATURE                       Location/Qualifiers
misc_feature                  1..28
                              note = primer sense351
source                        1..28
                              mol_type = other DNA
                              organism = synthetic construct
SEQUENCE: 340
ctgtacaaga ccacagaaag ggaactgt                                  28

SEQ ID NO: 341                moltype = DNA   length = 34
FEATURE                       Location/Qualifiers
misc_feature                  1..34
                              note = primer antisense
source                        1..34
                              mol_type = other DNA
                              organism = synthetic construct
SEQUENCE: 341
ccgcccggga gctcgttact ttccaagtcg gttc                           34
```